US006274718B1

(12) United States Patent
Travis et al.

(10) Patent No.: US 6,274,718 B1
(45) Date of Patent: *Aug. 14, 2001

(54) PORPHYROMONAS GINGIVALIS ARGININE-SPECIFIC PROTEINASE CODING SEQUENCES

(75) Inventors: James Travis; Jan Stanislaw Potempa, both of Athens, GA (US); Philip J. Barr, Berkeley; Nadine Pavloff, Novato, both of CA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/490,931

(22) Filed: Jan. 25, 2000

Related U.S. Application Data

(63) Continuation of application No. 08/336,308, filed on Nov. 8, 1994, now Pat. No. 6,017,523, which is a continuation-in-part of application No. PCT/US94/10283, filed on Sep. 9, 1994, which is a continuation of application No. 08/265,441, filed on Jun. 24, 1994, now abandoned, which is a continuation-in-part of application No. 08/119,361, filed on Sep. 10, 1993, now Pat. No. 5,523,390.

(51) Int. Cl.[7] .............................. C07H 21/04; C12N 9/52
(52) U.S. Cl. .......................................... 536/23.2; 435/220
(58) Field of Search ............................ 536/23.2; 435/220

(56) References Cited

U.S. PATENT DOCUMENTS

| 5,475,097 | 12/1995 | Travis et al. | 536/23.2 |
| 5,523,390 | 6/1996 | Travis et al. | 536/23.2 |
| 5,824,791 | 10/1998 | Progulske-Fox et al. | 536/237 |
| 5,830,710 | 11/1998 | Progulske-Fox et al. | 435/911 |
| 6,017,532 | 1/2000 | Travis et al. | 424/94.65 |

OTHER PUBLICATIONS

Imamura et al. (1994) "Pathogenesis of Peridontitis: A Major Arginine–Specific Cysteine Proteinase from *Porphyromonas gingivalis* Induces Vascular Permeability Enhancement through Activation of the Kallikrein/Kinin Pathway" *J. Clin. Invest.* 94:361–367.

Birkedal–Hansen et al. (1988) "Characterization of Collagenolytic Activity from Strains of *Bacteroides gingivalis*" *J. Periodontal Res.* 23:258–264.

Chen et al. (1992) "Purification and Characterization of a 50–kDa Cysteine Proteinase (Gingipain) from *Porphyromonas gingivalis*" *J. Biol. Chem.* 267:18896–18901.

Chen et al. (1991) "Stimulation of Proteinase and Amidase Activities in *Porphyromonas* (*Bacteroides*) *gingivalis* by Amino Acids and Dipeptides" *Infect. Immun.* 59:2846–2850.

Fugimura et al. (1987) "Isolation and Characterization of a Protease from *Bacteroides gingivalis*" *Infect. Immun.* 3(vol. 55):716–720.

Grenier et al. (1989) "Characterization of Sodium Dodecyl Sulfate–Stable *Bacteroides gingivalis* Proteases by Polyacrylamide Gel Electrophoresis" *Infect. Immun.* 57:95–99.

Hugli et al. (1991) "A Role for Complement in Gingivitis: Activation by a Cysteine Protease from *Porphyromonas gingivalis*" Abstract. *Clin. Exp. Immunol.* 86 (Suppl. 1), p. 20.

Lee et al. (1988) "Teach a Method of Cloning a Gene by Protein Sequencing the N–Terminal End and Making Degenerate Oligonucleotide Probes and Screening a Library with the Oligonucleotide Probes" *Science* 239:1288–1291.

Nishikata et al. (1991) "Characterization of *Porphyromonas* (*Bacteroides*) *gingivalis* Hemagglutinin as Protease" *Biochem. & Biophys. Res. Comm.* 1(178):336–342.

Ono et al. (1987) "Purification and Characterization of a Thiol–Protease from *Bacteroides gingivalis* Strain 381" *Oral Micr. Immuno.* 2:77–81.

Otogoto et al. (1993) "Isolation and Characterization of the *Porphyromonas gingivalis* prT Gene, Coding for Protease Activity" *Infect. & Immun.* 1(61):117–123.

(List continued on next page.)

*Primary Examiner*—Elizabeth Slobodyansky
(74) *Attorney, Agent, or Firm*—Greenlee Winner and Sullivan PC

(57) ABSTRACT

Provided herein is a nucleotide sequence encoding an Arg-specific gingipain, said Arg-gingipain characterized as having an apparent molecular mass of 50 kDa as estimated by sodium dodecyl sulfate polyacrylamide gel electrophoresis and an apparent molecular mass of 44 kDa as estimated by gel filtration chromatography, said gingipain-1 having amidolytic and proteolytic activity for cleavage after arginine residues and having no amidolytic and/or proteolytic activity for cleavage after lysine residues, wherein the amidolytic and/or proteolytic activity is inhibited by cysteine protease group-specific inhibitors including iodoacetamide, iodoacetic acid, N-ethylmaleimide, leupeptin, antipain, trans-epoxysuccinyl-L-leucylamido-(4-guanidino)butane, TLCK, TPCK, p-aminobenzamidine, N-chlorosuccinamide, and chelating agents including EDTA and EGTA, wherein the amidolytic and/or proteolytic activity of said gingipain-1 is not sensitive to inhibition by human cystatin C, $\alpha$2-macroglobulin, $\alpha$1-proteinase inhibitor, antithrombin III, $\alpha$2-antiplasmin, serine protease group-specific inhibitors including diisopropylfluorophosphate, phenylmethyl sulfonylfluoride and proteolytic activities of ginigipan-1 are stabilized by $Ca^{2+}$ and 3,4-diisochlorocoumarin, and wherein the amidolytic and/or wherein the amidolytic and/or proteolytic activities of said gingipain-1 are stimulated by glycine-containing peptides and glycine analogues, and methods for preparation. As specifically exemplified, high and low molecular weight forms of Arg-gingipains and sequences encoding them are prepared from *Porphyromonas gingivalis*. Said high molecular weight Arg-gingipain comprises a proteolytic component as described hereinabove and at least one hemagglutinin component.

4 Claims, 5 Drawing Sheets

OTHER PUBLICATIONS

Otsuka et al. (1987) "Isolation and Characterization of Protease from Culture Supernatant of *Bacteroides gingivalis*" *J. Periodont Res.* 22:491–498.

Park et al. (1992) "Cloning of a *Porphyromonas* (*Bacteriodes*) *gingivalis* Protease Gene and Characterization of its Product" *FEMS Microb. Lett.* 92:273–278.

Potempa et al. (1991) "Purification and Characterization of a 50 kD Cysteine Proteinase of *Porphyromonas gingivalis*" Abstract. *FASEB J.* 5(4):A829.

Roberts et al. (1990) "Purification of the Secreted Thiol–Activated Protease of *Porphyromonas* (*Bacteroides*) *gingivalis* and the Cloning and Expression of the Gene in *Escherichia coli*" *Clinical & Molecular Aspects of Anaerobes* (ed., S.P. Borriello) pp. 227–233.

Schenkein, H.A. (1988) "The Effect of Periodontal Proteolytic Bacteroides Species on Proteins of the Human Complement System" *J. Periodontal Res.* 23:187–192.

Shah et al. (1992) "Evidence for Independent Molecular Identity and Functional Interaction of the Haemagglutinin and Cystine Proteinase (gingivain) of *Porphyromonas gingivalis*" *J. Med. Microbiol.* 36:239–244.

Sorsa et al. (1987) A Trypsin–Like Protease for *Bacteroides gingivalis:* Partial Purification and Characterization: *J. Periodont. Res.* 22:375–380.

Suido et al. (1987) "Characterization of N–CBz–glycyl–g-lycyl–arginyl Peptidase and glycyl–prolyl Peptidase of *Bacteroides gingivalis*" *J. Periodont. Res.* 22:412–418.

Travis et al. (1991) "Bacterial Proteinases in Periodontal Disease" Abstract *J. Cell Biochem.* Suppl. O (15 Part G) p. 117).

Tsutsui et al. (1987) "Purification and characterization of a Protease from *Bacteroides gingivalis* 381" *Infect. Immun.* 55:420–427.

Uitto, V.J. (1987) "Human Gingival Proteases. 1: Extraction and Preliminary Characterization of Trypsin–Like and Elastase–Like Enzymes" *J. Periodontal Res.* 22:58–63.

Wingrove et al. (1992) "Activation of Complement Components C3 and C5 by a Cysteine Proteinase (Gingipain–1) from *Porphyromonas* (*Bacteroides*) *gingivalis*" *J. Biol. Chem.* 287:18902–18907.

Yoshimura et al. (1994) "Characterization of a Trypsin–Like Protease from the Bacterium *Bacteroides gingivalis* Isolated from Human Dental Plaque" *Archs Oral Biol.* 29:559–564.

```
                           SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
          (A) LENGTH: 43 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
          (A) ORGANISM: Porphyromonas gingivalis
          (B) STRAIN: H66

(xi) SEQUENCE DESCRIPTION: SEQ ID NO:1:

Tyr Thr Pro Val Glu Glu Lys Gln Asn Gly Arg Met Ile Val Ile Val
1               5                  10                  15

Ala Lys Lys Tyr Glu Gly Asp Ile Lys Asp Phe Val Asp Trp Lys Asn
            20                  25                  30

Gln Arg Gly Leu Thr Lys Xaa Val Lys Xaa Ala
            35                  40

(2) INFORMATION FOR SEQ ID NO:2:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO:2:

Glu Leu Leu Arg
1

(2) INFORMATION FOR SEQ ID NO:3:

(i) SEQUENCE CHARACTERISTICS:
          (A) LENGTH: 3159 base pairs
          (B) TYPE: nucleic acid
          (C) STRANDEDNESS: double
          (D) TOPOLOGY: linear
```

-continued (ii) MOLECULE TYPE: DNA (genomic)

(iii) HYPOTHETICAL: NO (iv) ANTI-SENSE: NO (ix) FEATURE:
    (A) NAME/KEY: CDS
    (B) LOCATION: 949..3159

(ix) FEATURE:
    (A) NAME/KEY: mat_peptide
    (B) LOCATION: 1630..3105

(xi) SEQUENCE DESCRIPTION: SEQ ID NO:3:

```
CTGCAGAGGG CTGGTAAAGA CCGCCTCGGG ATCGAGGCCT TGAGACGGG CACAAGCCGC      60

CGCAGCCTCC TCTTCGAAGG TGTCTCGAAC GTCCACATCG GTGAATCCGT AGCAGTGCTC    120

ATTGCCATTG AGCAGCACCG AGGTGTGGCG CATCAGATAT ATTTTCATCA GTGGATTATT    180

AGGGTATCGG TCAGAAAAAG CCTTCCGAAT CCGACAAAGA TAGTAGAAAG AGAGTGCATC    240

TGAAAACAGA TCATTCGAGG ATTATCGATC AACTGAAAAG GCAGGAGTTG TTTTGCGTTT    300

TGGTTCGGAA AATTACCTGA TCAGCATTCG TAAAAACGTG GCGCGAGAAT TTTTTCGTTT    360

TGGCGCGAGA ATTAAAAATT TTTGGAACCA CAGCGAAAAA AATCTCGCGC CGTTTTCTCA    420

GGATTTACAG ACCACAATCC GAGCATTTTC GGTTCGTAAT TCATCGAAGA GACAGGTTTT    480

ACCGCATTGA AATCAGAGAG AGAATATCCG TAGTCCAACG GTTCATCCTT ATATCAGAGG    540

TTAAAAGATA TGGTACGCTC ATCGAGGAGC TGATTGGCTT AGTAGGTGAG ACTTTCTTAA    600

GAGACTATCG GCACCTACAG GAAGTTCATG GCACACAAGG CAAAGGAGGC AATCTTCGCA    660

GACCGGACTC ATATCAAAAG GATGAAACGA CTTTTCCATA CGACAACCAA ATAGCCGTCT    720

ACGGTAGACG AATGCAAACC CAATATGAGG CCATCAATCA ATCCGAATGA CAGCTTTTGG    780

GCAATATATT ATGCATATTT TGATTCGCGT TTAAAGGAAA AGTGCATATA TTTGCGATTG    840

TGGTATTTCT TTCGGTTTCT ATGTGAATTT TGTCTCCCAA GAAGACTTTA TAATGCATAA    900

ATACAGAAGG GGTACTACAC AGTAAAATCA TATTCTAATT TCATCAAA ATG AAA AAC    957
                                                   Met Lys Asn
                                                   -227     -225

TTG AAC AAG TTT GTT TCG ATT GCT CTT TGC TCT TCC TTA TTA GGA GGA    1005
Leu Asn Lys Phe Val Ser Ile Ala Leu Cys Ser Ser Leu Leu Gly Gly
         -220             -215             -210

ATG GCA TTT GCG CAG CAG ACA GAG TTG GGA CGC AAT CCG AAT GTC AGA    1053
Met Ala Phe Ala Gln Gln Thr Glu Leu Gly Arg Asn Pro Asn Val Arg
         -205             -200             -195

TTG CTC GAA TCC ACT CAG CAA TCG GTG ACA AAG GTT CAG TTC CGT ATG    1101
Leu Leu Glu Ser Thr Gln Gln Ser Val Thr Lys Val Gln Phe Arg Met
         -190             -185             -180

GAC AAC CTC AAG TTC ACC GAA GTT CAA ACC CCT AAG GGA ATC GGA CAA    1149
Asp Asn Leu Lys Phe Thr Glu Val Gln Thr Pro Lys Gly Ile Gly Gln
-175             -170                 -165

GTG CCG ACC TAT ACA GAA GGG GTT AAT CTT TCC GAA AAA GGG ATG CCT    1197
Val Pro Thr Tyr Thr Glu Gly Val Asn Leu Ser Glu Lys Gly Met Pro
-160             -155                 -150             -145

ACG CTT CCC ATT CTA TCA CGC TCT TTG GCG GTT TCA GAC ACT CGT GAG    1245
Thr Leu Pro Ile Leu Ser Arg Ser Leu Ala Val Ser Asp Thr Arg Glu
             -140             -135             -130

ATG AAG GTA GAG GTT GTT TCC TCA AAG TTC ATC GAA AAG AAA AAT GTC    1293
Met Lys Val Glu Val Val Ser Ser Lys Phe Ile Glu Lys Lys Asn Val
         -125             -120             -115
```

```
CTG ATT GCA CCC TCC AAG GGC ATG ATT ATG CGT AAC GAA GAT CCG AAA     1341
Leu Ile Ala Pro Ser Lys Gly Met Ile Met Arg Asn Glu Asp Pro Lys
        -110            -105            -100

AAG ATC CCT TAC GTT TAT GGA AAG AGC TAC TCG CAA AAC AAA TTC TTC     1389
Lys Ile Pro Tyr Val Tyr Gly Lys Ser Tyr Ser Gln Asn Lys Phe Phe
    -95             -90             -85

CCG GGA GAG ATC GCC ACG CTT GAT GAT CCT TTT ATC CTT CGT GAT GTG     1437
Pro Gly Glu Ile Ala Thr Leu Asp Asp Pro Phe Ile Leu Arg Asp Val
-80             -75             -70                         -65

CGT GGA CAG GTT GTA AAC TTT GCG CCT TTG CAG TAT AAC CCT GTG ACA     1485
Arg Gly Gln Val Val Asn Phe Ala Pro Leu Gln Tyr Asn Pro Val Thr
                -60             -55                     -50

AAG ACG TTG CGC ATC TAT ACG GAA ATC ACT GTG GCA GTG AGC GAA ACT     1533
Lys Thr Leu Arg Ile Tyr Thr Glu Ile Thr Val Ala Val Ser Glu Thr
            -45             -40                 -35

TCG GAA CAA GGC AAA AAT ATT CTG AAC AAG AAA GGT ACA TTT GCC GGC     1581
Ser Glu Gln Gly Lys Asn Ile Leu Asn Lys Lys Gly Thr Phe Ala Gly
        -30             -25             -20

TTT GAA GAC ACA TAC AAG CGC ATG TTC ATG AAC TAC GAG CCG GGG CGT     1629
Phe Glu Asp Thr Tyr Lys Arg Met Phe Met Asn Tyr Glu Pro Gly Arg
    -15             -10             -5

TAC ACA CCG GTA GAG GAA AAA CAA AAT GGT CGT ATG ATC GTC ATC GTA     1677
Tyr Thr Pro Val Glu Glu Lys Gln Asn Gly Arg Met Ile Val Ile Val
1               5               10              15

GCC AAA AAG TAT GAG GGA GAT ATT AAA GAT TTC GTT GAT TGG AAA AAC     1725
Ala Lys Lys Tyr Glu Gly Asp Ile Lys Asp Phe Val Asp Trp Lys Asn
        20              25              30

CAA CGC GGT CTC CGT ACC GAG GTG AAA GTG GCA GAA GAT ATT GCT TCT     1773
Gln Arg Gly Leu Arg Thr Glu Val Lys Val Ala Glu Asp Ile Ala Ser
        35              40              45

CCC GTT ACA GCT AAT GCT ATT CAG CAG TTC GTT AAG CAA GAA TAC GAG     1821
Pro Val Thr Ala Asn Ala Ile Gln Gln Phe Val Lys Gln Glu Tyr Glu
    50              55              60

AAA GAA GGT AAT GAT TTG ACC TAT GTT CTT TTG GTT GGC GAT CAC AAA     1869
Lys Glu Gly Asn Asp Leu Thr Tyr Val Leu Leu Val Gly Asp His Lys
65              70              75              80

GAT ATT CCT GCC AAA ATT ACT CCG GGG ATC AAA TCC GAC CAG GTA TAT     1917
Asp Ile Pro Ala Lys Ile Thr Pro Gly Ile Lys Ser Asp Gln Val Tyr
            85              90              95

GGA CAA ATA GTA GGT AAT GAC CAC TAC AAC GAA GTC TTC ATC GGT CGT     1965
Gly Gln Ile Val Gly Asn Asp His Tyr Asn Glu Val Phe Ile Gly Arg
        100             105             110

TTC TCA TGT GAG AGC AAA GAG GAT CTG AAG ACA CAA ATC GAT CGG ACT     2013
Phe Ser Cys Glu Ser Lys Glu Asp Leu Lys Thr Gln Ile Asp Arg Thr
        115             120             125

ATT CAC TAT GAG CGC AAT ATA ACC ACG GAA GAC AAA TGG CTC GGT CAG     2061
Ile His Tyr Glu Arg Asn Ile Thr Thr Glu Asp Lys Trp Leu Gly Gln
130             135             140

GCT CTT TGT ATT GCT TCG GCT GAA GGA GGC CCA TCC GCA GAC AAT GGT     2109
Ala Leu Cys Ile Ala Ser Ala Glu Gly Gly Pro Ser Ala Asp Asn Gly
145             150             155             160

GAA AGT GAT ATC CAG CAT GAG AAT GTA ATC GCC AAT CTG CTT ACC CAG     2157
Glu Ser Asp Ile Gln His Glu Asn Val Ile Ala Asn Leu Leu Thr Gln
            165             170             175

TAT GGC TAT ACC AAG ATT ATC AAA TGT TAT GAT CCG GGA GTA ACT CCT     2205
Tyr Gly Tyr Thr Lys Ile Ile Lys Cys Tyr Asp Pro Gly Val Thr Pro
                180             185             190

AAA AAC ATT ATT GAT GCT TTC AAC GGA GGA ATC TCG TTG GTC AAC TAT     2253
Lys Asn Ile Ile Asp Ala Phe Asn Gly Gly Ile Ser Leu Val Asn Tyr
```

-continued

```
               195                     200                     205
ACG GGC CAC GGT AGC GAA ACA GCT TGG GGT ACG TCT CAC TTC GGC ACC        2301
Thr Gly His Gly Ser Glu Thr Ala Trp Gly Thr Ser His Phe Gly Thr
        210                     215                     220

ACT CAT GTG AAG CAG CTT ACC AAC AGC AAC CAG CTA CCG TTT ATT TTC        2349
Thr His Val Lys Gln Leu Thr Asn Ser Asn Gln Leu Pro Phe Ile Phe
225                     230                     235                 240

GAC GTA GCT TGT GTG AAT GGC GAT TTC CTA TTC AGC ATG CCT TGC TTC        2397
Asp Val Ala Cys Val Asn Gly Asp Phe Leu Phe Ser Met Pro Cys Phe
                245                     250                     255

GCA GAA GCC CTG ATG CGT GCA CAA AAA GAT GGT AAG CCG ACA GGT ACT        2445
Ala Glu Ala Leu Met Arg Ala Gln Lys Asp Gly Lys Pro Thr Gly Thr
            260                     265                     270

GTT GCT ATC ATA GCG TCT ACG ATC AAC CAG TCT TGG GCT TCT CCT ATG        2493
Val Ala Ile Ile Ala Ser Thr Ile Asn Gln Ser Trp Ala Ser Pro Met
        275                     280                     285

CGC GGG CAG GAT GAG ATG AAC GAA ATT CTG TGC GAA AAA CAC CCG AAC        2541
Arg Gly Gln Asp Glu Met Asn Glu Ile Leu Cys Glu Lys His Pro Asn
    290                     295                     300

AAC ATC AAG CGT ACT TTC GGT GGT GTC ACC ATG AAC GGT ATG TTT GCT        2589
Asn Ile Lys Arg Thr Phe Gly Gly Val Thr Met Asn Gly Met Phe Ala
305                     310                     315                 320

ATG GTG GAA AAG TAT AAA AAG GAT GGT GAG AAG ATG CTC GAC ACA TGG        2637
Met Val Glu Lys Tyr Lys Lys Asp Gly Glu Lys Met Leu Asp Thr Trp
                325                     330                     335

ACT GTT TTC GGC GAC CCC TCG CTG CTC GTT CGT ACA CTT GTC CCG ACC        2685
Thr Val Phe Gly Asp Pro Ser Leu Leu Val Arg Thr Leu Val Pro Thr
            340                     345                     350

AAA ATG CAG GTT ACG GCT CCG GCT CAG ATT AAT TTG ACG GAT GCT TCA        2733
Lys Met Gln Val Thr Ala Pro Ala Gln Ile Asn Leu Thr Asp Ala Ser
        355                     360                     365

GTC AAC GTA TCT TGC GAT TAT AAT GGT GCT ATT GCT ACC ATT TCA GCC        2781
Val Asn Val Ser Cys Asp Tyr Asn Gly Ala Ile Ala Thr Ile Ser Ala
    370                     375                     380

AAT GGA AAG ATG TTC GGT TCT GCA GTT GTC GAA AAT GGA ACA GCT ACA        2829
Asn Gly Lys Met Phe Gly Ser Ala Val Val Glu Asn Gly Thr Ala Thr
385                     390                     395                 400

ATC AAT CTG ACA GGT CTG ACA AAT GAA AGC ACG CTT ACC CTT ACA GTA        2877
Ile Asn Leu Thr Gly Leu Thr Asn Glu Ser Thr Leu Thr Leu Thr Val
                405                     410                     415

GTT GGT TAC AAC AAA GAG ACG GTT ATT AAG ACC ATC AAC ACT AAT GGT        2925
Val Gly Tyr Asn Lys Glu Thr Val Ile Lys Thr Ile Asn Thr Asn Gly
            420                     425                     430

GAG CCT AAC CCC TAC CAG CCC GTT TCC AAC TTG ACA GCT ACA ACG CAG        2973
Glu Pro Asn Pro Tyr Gln Pro Val Ser Asn Leu Thr Ala Thr Thr Gln
        435                     440                     445

GGT CAG AAA GTA ACG CTC AAG TGG GAT GCA CCG AGC ACG AAA ACC AAT        3021
Gly Gln Lys Val Thr Leu Lys Trp Asp Ala Pro Ser Thr Lys Thr Asn
    450                     455                     460

GCA ACC ACT AAT ACC GCT CGC AGC GTG GAT GGC ATA CGA GAA TTG GTT        3069
Ala Thr Thr Asn Thr Ala Arg Ser Val Asp Gly Ile Arg Glu Leu Val
465                     470                     475                 480

CTT CTG TCA GTC AGC GAT GCC CCC GAA CTT CTT CGC AGC GGT CAG GCC        3117
Leu Leu Ser Val Ser Asp Ala Pro Glu Leu Leu Arg Ser Gly Gln Ala
                485                     490                     495

GAG ATT GTT CTT GAA GCT CAC GAT GTT TGG AAT GAT GGA TCC                3159
Glu Ile Val Leu Glu Ala His Asp Val Trp Asn Asp Gly Ser
            500                     505                     510
```

(2) INFORMATION FOR SEQ ID NO:4:

(i) SEQUENCE CHARACTERISTICS:
        (A) LENGTH: 737 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Asn Leu Asn Lys Phe Val Ser Ile Ala Leu Cys Ser Ser Leu
-227     -225             -220             -215

Leu Gly Gly Met Ala Phe Ala Gln Gln Thr Glu Leu Gly Arg Asn Pro
    -210         -205             -200

Asn Val Arg Leu Leu Glu Ser Thr Gln Gln Ser Val Thr Lys Val Gln
-195         -190             -185             -180

Phe Arg Met Asp Asn Leu Lys Phe Thr Glu Val Gln Thr Pro Lys Gly
        -175             -170             -165

Ile Gly Gln Val Pro Thr Tyr Thr Glu Gly Val Asn Leu Ser Glu Lys
        -160             -155             -150

Gly Met Pro Thr Leu Pro Ile Leu Ser Arg Ser Leu Ala Val Ser Asp
        -145             -140             -135

Thr Arg Glu Met Lys Val Glu Val Val Ser Ser Lys Phe Ile Glu Lys
        -130             -125             -120

Lys Asn Val Leu Ile Ala Pro Ser Lys Gly Met Ile Met Arg Asn Glu
-115             -110             -105             -100

Asp Pro Lys Lys Ile Pro Tyr Val Tyr Gly Lys Ser Tyr Ser Gln Asn
            -95             -90             -85

Lys Phe Phe Pro Gly Glu Ile Ala Thr Leu Asp Asp Pro Phe Ile Leu
            -80             -75             -70

Arg Asp Val Arg Gly Gln Val Val Asn Phe Ala Pro Leu Gln Tyr Asn
            -65             -60             -55

Pro Val Thr Lys Thr Leu Arg Ile Tyr Thr Glu Ile Thr Val Ala Val
            -50             -45             -40

Ser Glu Thr Ser Glu Gln Gly Lys Asn Ile Leu Asn Lys Lys Gly Thr
-35              -30             -25             -20

Phe Ala Gly Phe Glu Asp Thr Tyr Lys Arg Met Phe Met Asn Tyr Glu
                -15             -10             -5

Pro Gly Arg Tyr Thr Pro Val Glu Glu Lys Gln Asn Gly Arg Met Ile
             1              5               10

Val Ile Val Ala Lys Lys Tyr Glu Gly Asp Ile Lys Asp Phe Val Asp
     15              20              25

Trp Lys Asn Gln Arg Gly Leu Arg Thr Glu Val Lys Val Ala Glu Asp
 30              35              40              45

Ile Ala Ser Pro Val Thr Ala Asn Ala Ile Gln Gln Phe Val Lys Gln
             50              55              60

Glu Tyr Glu Lys Glu Gly Asn Asp Leu Thr Tyr Val Leu Leu Val Gly
             65              70              75

Asp His Lys Asp Ile Pro Ala Lys Ile Thr Pro Gly Ile Lys Ser Asp
         80              85              90

Gln Val Tyr Gly Gln Ile Val Gly Asn Asp His Tyr Asn Glu Val Phe
         95              100             105

Ile Gly Arg Phe Ser Cys Glu Ser Lys Glu Asp Leu Lys Thr Gln Ile
110             115             120             125

Asp Arg Thr Ile His Tyr Glu Arg Asn Ile Thr Thr Glu Asp Lys Trp
```

```
                  130                 135                 140
Leu Gly Gln Ala Leu Cys Ile Ala Ser Ala Glu Gly Gly Pro Ser Ala
            145                 150                 155

Asp Asn Gly Glu Ser Asp Ile Gln His Glu Asn Val Ile Ala Asn Leu
            160                 165                 170

Leu Thr Gln Tyr Gly Tyr Thr Lys Ile Ile Lys Cys Tyr Asp Pro Gly
175                 180                 185

Val Thr Pro Lys Asn Ile Ile Asp Ala Phe Asn Gly Gly Ile Ser Leu
190                 195                 200                 205

Val Asn Tyr Thr Gly His Gly Ser Glu Thr Ala Trp Gly Thr Ser His
            210                 215                 220

Phe Gly Thr Thr His Val Lys Gln Leu Thr Asn Ser Asn Gln Leu Pro
            225                 230                 235

Phe Ile Phe Asp Val Ala Cys Val Asn Gly Asp Phe Leu Phe Ser Met
            240                 245                 250

Pro Cys Phe Ala Glu Ala Leu Met Arg Ala Gln Lys Asp Gly Lys Pro
            255                 260                 265

Thr Gly Thr Val Ala Ile Ile Ala Ser Thr Ile Asn Gln Ser Trp Ala
270                 275                 280                 285

Ser Pro Met Arg Gly Gln Asp Glu Met Asn Glu Ile Leu Cys Glu Lys
            290                 295                 300

His Pro Asn Asn Ile Lys Arg Thr Phe Gly Gly Val Thr Met Asn Gly
            305                 310                 315

Met Phe Ala Met Val Glu Lys Tyr Lys Lys Asp Gly Glu Lys Met Leu
            320                 325                 330

Asp Thr Trp Thr Val Phe Gly Asp Pro Ser Leu Leu Val Arg Thr Leu
            335                 340                 345

Val Pro Thr Lys Met Gln Val Thr Ala Pro Ala Gln Ile Asn Leu Thr
350                 355                 360                 365

Asp Ala Ser Val Asn Val Ser Cys Asp Tyr Asn Gly Ala Ile Ala Thr
                370                 375                 380

Ile Ser Ala Asn Gly Lys Met Phe Gly Ser Ala Val Val Glu Asn Gly
            385                 390                 395

Thr Ala Thr Ile Asn Leu Thr Gly Leu Thr Asn Glu Ser Thr Leu Thr
            400                 405                 410

Leu Thr Val Val Gly Tyr Asn Lys Glu Thr Val Ile Lys Thr Ile Asn
415                 420                 425

Thr Asn Gly Glu Pro Asn Pro Tyr Gln Pro Val Ser Asn Leu Thr Ala
430                 435                 440                 445

Thr Thr Gln Gly Gln Lys Val Thr Leu Lys Trp Asp Ala Pro Ser Thr
            450                 455                 460

Lys Thr Asn Ala Thr Thr Asn Thr Ala Arg Ser Val Asp Gly Ile Arg
            465                 470                 475

Glu Leu Val Leu Leu Ser Val Ser Asp Ala Pro Glu Leu Leu Arg Ser
            480                 485                 490

Gly Gln Ala Glu Ile Val Leu Glu Ala His Asp Val Trp Asn Asp Gly
            495                 500                 505

Ser
510

(2) INFORMATION FOR SEQ ID NO:5:

(i) SEQUENCE CHARACTERISTICS:
        (A) LENGTH: 26 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:5:

GGCTTTACNC CNGTNGARGA RYTNGA                                    26

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:6:

GGCTTTRTTY TTCCARTCNA CRAARTCYTT                                30

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:7:

CCTGGAGAAT TCTCGTATGA TCGTCATCGT AGCCAAAAAG TATGAGGG            48

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:8:

ATCAACACTA ATGGTGAGCC                                           20

(2) INFORMATION FOR SEQ ID NO:9:

(i) SEQUENCE CHARACTERISTICS:
        (A) LENGTH: 7266 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO

-continued (ix) FEATURE:
    (A) NAME/KEY: CDS
    (B) LOCATION: 949..6063

(xi) SEQUENCE DESCRIPTION: SEQ ID NO:9:

```
CTGCAGAGGG CTGGTAAAGA CCGCCTCGGG ATCGAGGCCT TTGAGACGGG CACAAGCCGC      60

CGCAGCCTCC TCTTCGAAGG TGTCTCGAAC GTCCACATCG GTGAATCCGT AGCAGTGCTC     120

ATTGCCATTG AGCAGCACCG AGGTGTGGCG CATCAGATAT ATTTTCATCA GTGGATTATT     180

AGGGTATCGG TCAGAAAAAG CCTTCCGAAT CCGACAAAGA TAGTAGAAAG AGAGTGCATC     240

TGAAAACAGA TCATTCGAGG ATTATCGATC AACTGAAAAG GCAGGAGTTG TTTTGCGTTT     300

TGGTTCGGAA AATTACCTGA TCAGCATTCG TAAAAACGTG GCGCGAGAAT TTTTTCGTTT     360

TGGCGCGAGA ATTAAAAATT TTTGGAACCA CAGCGAAAAA AATCTCGCGC CGTTTTCTCA     420

GGATTTACAG ACCACAATCC GAGCATTTTC GGTTCGTAAT TCATCGAAGA DACAGGTTTT     480
```
(Note: line 8 reads `GGATTTACAG ACCACAATCC GAGCATTTTC GGTTCGTAAT TCATCGAAGA GACAGGTTTT     480`)

```
ACCGCATTGA ATCAGAGAG  AGAATATCCG TAGTCCAACG GTTCATCCTT ATATCAGAGG     540

TTAAAAGATA TGGTACGCTC ATCGAGGAGC TGATTGGCTT AGTAGGTGAG ACTTTCTTAA     600

GAGACTATCG GCACCTACAG GAAGTTCATG GCACACAAGG CAAAGGAGGC AATCTTCGCA     660

GACCGGACTC ATATCAAAAG GATGAAACGA CTTTTCCATA CGACAACCAA ATAGCCGTCT     720

ACGGTAGACG AATGCAAACC CAATATGAGG CCATCAATCA ATCCGAATGA CAGCTTTTGG     780

GCAATATATT ATGCATATTT TGATTCGCGT TTAAAGGAAA AGTGCATATA TTTGCGATTG     840

TGGTATTTCT TTCGGTTTCT ATGTGAATTT TGTCTCCCAA GAAGACTTTA TAATGCATAA     900

ATACAGAAGG GGTACTACAC AGTAAAATCA TATTCTAATT TCATCAAA ATG AAA AAC     957
                                                        Met Lys Asn
                                                          1
```

```
TTG AAC AAG TTT GTT TCG ATT GCT CTT TGC TCT TCC TTA TTA GGA GGA      1005
Leu Asn Lys Phe Val Ser Ile Ala Leu Cys Ser Ser Leu Leu Gly Gly
          5                  10                  15

ATG GCA TTT GCG CAG CAG ACA GAG TTG GGA CGC AAT CCG AAT GTC AGA      1053
Met Ala Phe Ala Gln Gln Thr Glu Leu Gly Arg Asn Pro Asn Val Arg
 20                  25                  30                  35

TTG CTC GAA TCC ACT CAG CAA TCG GTG ACA AAG GTT CAG TTC CGT ATG      1101
Leu Leu Glu Ser Thr Gln Gln Ser Val Thr Lys Val Gln Phe Arg Met
                 40                  45                  50

GAC AAC CTC AAG TTC ACC GAA GTT CAA ACC CCT AAG GGA ATC GGA CAA      1149
Asp Asn Leu Lys Phe Thr Glu Val Gln Thr Pro Lys Gly Ile Gly Gln
             55                  60                  65

GTG CCG ACC TAT ACA GAA GGG GTT AAT CTT TCC GAA AAA GGG ATG CCT      1197
Val Pro Thr Tyr Thr Glu Gly Val Asn Leu Ser Glu Lys Gly Met Pro
         70                  75                  80

ACG CTT CCC ATT CTA TCA CGC TCT TTG GCG GTT TCA GAC ACT CGT GAG      1245
Thr Leu Pro Ile Leu Ser Arg Ser Leu Ala Val Ser Asp Thr Arg Glu
     85                  90                  95

ATG AAG GTA GAG GTT GTT TCC TCA AAG TTC ATC GAA AAG AAA AAT GTC      1293
Met Lys Val Glu Val Val Ser Ser Lys Phe Ile Glu Lys Lys Asn Val
100                 105                 110                 115

CTG ATT GCA CCC TCC AAG GGC ATG ATT ATG CGT AAC GAA GAT CCG AAA      1341
Leu Ile Ala Pro Ser Lys Gly Met Ile Met Arg Asn Glu Asp Pro Lys
                120                 125                 130

AAG ATC CCT TAC GTT TAT GGA AAG AGC TAC TCG CAA AAC AAA TTC TTC      1389
Lys Ile Pro Tyr Val Tyr Gly Lys Ser Tyr Ser Gln Asn Lys Phe Phe
            135                 140                 145

CCG GGA GAG ATC GCC ACG CTT GAT GAT CCT TTT ATC CTT CGT GAT GTG      1437
```

-continued

```
        Pro Gly Glu Ile Ala Thr Leu Asp Asp Pro Phe Ile Leu Arg Asp Val
                    150                 155                 160

CGT GGA CAG GTT GTA AAC TTT GCG CCT TTG CAG TAT AAC CCT GTG ACA         1485
Arg Gly Gln Val Val Asn Phe Ala Pro Leu Gln Tyr Asn Pro Val Thr
165                 170                 175

AAG ACG TTG CGC ATC TAT ACG GAA ATC ACT GTG GCA GTG AGC GAA ACT         1533
Lys Thr Leu Arg Ile Tyr Thr Glu Ile Thr Val Ala Val Ser Glu Thr
180                 185                 190                 195

TCG GAA CAA GGC AAA AAT ATT CTG AAC AAG AAA GGT ACA TTT GCC GGC         1581
Ser Glu Gln Gly Lys Asn Ile Leu Asn Lys Lys Gly Thr Phe Ala Gly
                    200                 205                 210

TTT GAA GAC ACA TAC AAG CGC ATG TTC ATG AAC TAC GAG CCG GGG CGT         1629
Phe Glu Asp Thr Tyr Lys Arg Met Phe Met Asn Tyr Glu Pro Gly Arg
                215                 220                 225

TAC ACA CCG GTA GAG GAA AAA CAA AAT GGT CGT ATG ATC GTC ATC GTA         1677
Tyr Thr Pro Val Glu Glu Lys Gln Asn Gly Arg Met Ile Val Ile Val
            230                 235                 240

GCC AAA AAG TAT GAG GGA GAT ATT AAA GAT TTC GTT GAT TGG AAA AAC         1725
Ala Lys Lys Tyr Glu Gly Asp Ile Lys Asp Phe Val Asp Trp Lys Asn
        245                 250                 255

CAA CGC GGT CTC CGT ACC GAG GTG AAA GTG GCA GAA GAT ATT GCT TCT         1773
Gln Arg Gly Leu Arg Thr Glu Val Lys Val Ala Glu Asp Ile Ala Ser
260                 265                 270                 275

CCC GTT ACA GCT AAT GCT ATT CAG CAG TTC GTT AAG CAA GAA TAC GAG         1821
Pro Val Thr Ala Asn Ala Ile Gln Gln Phe Val Lys Gln Glu Tyr Glu
                280                 285                 290

AAA GAA GGT AAT GAT TTG ACC TAT GTT CTT TTG GTT GGC GAT CAC AAA         1869
Lys Glu Gly Asn Asp Leu Thr Tyr Val Leu Leu Val Gly Asp His Lys
                295                 300                 305

GAT ATT CCT GCC AAA ATT ACT CCG GGG ATC AAA TCC GAC CAG GTA TAT         1917
Asp Ile Pro Ala Lys Ile Thr Pro Gly Ile Lys Ser Asp Gln Val Tyr
            310                 315                 320

GGA CAA ATA GTA GGT AAT GAC CAC TAC AAC GAA GTC TTC ATC GGT CGT         1965
Gly Gln Ile Val Gly Asn Asp His Tyr Asn Glu Val Phe Ile Gly Arg
        325                 330                 335

TTC TCA TGT GAG AGC AAA GAG GAT CTG AAG ACA CAA ATC GAT CGG ACT         2013
Phe Ser Cys Glu Ser Lys Glu Asp Leu Lys Thr Gln Ile Asp Arg Thr
340                 345                 350                 355

ATT CAC TAT GAG CGC AAT ATA ACC ACG GAA GAC AAA TGG CTC GGT CAG         2061
Ile His Tyr Glu Arg Asn Ile Thr Thr Glu Asp Lys Trp Leu Gly Gln
                360                 365                 370

GCT CTT TGT ATT GCT TCG GCT GAA GGA GGC CCA TCC GCA GAC AAT GGT         2109
Ala Leu Cys Ile Ala Ser Ala Glu Gly Gly Pro Ser Ala Asp Asn Gly
                375                 380                 385

GAA AGT GAT ATC CAG CAT GAG AAT GTA ATC GCC AAT CTG CTT ACC CAG         2157
Glu Ser Asp Ile Gln His Glu Asn Val Ile Ala Asn Leu Leu Thr Gln
            390                 395                 400

TAT GGC TAT ACC AAG ATT ATC AAA TGT TAT GAT CCG GGA GTA ACT CCT         2205
Tyr Gly Tyr Thr Lys Ile Ile Lys Cys Tyr Asp Pro Gly Val Thr Pro
        405                 410                 415

AAA AAC ATT ATT GAT GCT TTC AAC GGA GGA ATC TCG TTG GTC AAC TAT         2253
Lys Asn Ile Ile Asp Ala Phe Asn Gly Gly Ile Ser Leu Val Asn Tyr
420                 425                 430                 435

ACG GGC CAC GGT AGC GAA ACA GCT TGG GGT ACG TCT CAC TTC GGC ACC         2301
Thr Gly His Gly Ser Glu Thr Ala Trp Gly Thr Ser His Phe Gly Thr
                440                 445                 450

ACT CAT GTG AAG CAG CTT ACC AAC AGC AAC CAG CTA CCG TTT ATT TTC         2349
Thr His Val Lys Gln Leu Thr Asn Ser Asn Gln Leu Pro Phe Ile Phe
            455                 460                 465
```

```
GAC GTA GCT TGT GTG AAT GGC GAT TTC CTA TTC AGC ATG CCT TGC TTC      2397
Asp Val Ala Cys Val Asn Gly Asp Phe Leu Phe Ser Met Pro Cys Phe
            470                 475                 480

GCA GAA GCC CTG ATG CGT GCA CAA AAA GAT GGT AAG CCG ACA GGT ACT      2445
Ala Glu Ala Leu Met Arg Ala Gln Lys Asp Gly Lys Pro Thr Gly Thr
        485                 490                 495

GTT GCT ATC ATA GCG TCT ACG ATC AAC CAG TCT TGG GCT TCT CCT ATG      2493
Val Ala Ile Ile Ala Ser Thr Ile Asn Gln Ser Trp Ala Ser Pro Met
500                 505                 510                 515

CGC GGG CAG GAT GAG ATG AAC GAA ATT CTG TGC GAA AAA CAC CCG AAC      2541
Arg Gly Gln Asp Glu Met Asn Glu Ile Leu Cys Glu Lys His Pro Asn
                520                 525                 530

AAC ATC AAG CGT ACT TTC GGT GGT GTC ACC ATG AAC GGT ATG TTT GCT      2589
Asn Ile Lys Arg Thr Phe Gly Gly Val Thr Met Asn Gly Met Phe Ala
            535                 540                 545

ATG GTG GAA AAG TAT AAA AAG GAT GGT GAG AAG ATG CTC GAC ACA TGG      2637
Met Val Glu Lys Tyr Lys Lys Asp Gly Glu Lys Met Leu Asp Thr Trp
        550                 555                 560

ACT GTT TTC GGC GAC CCC TCG CTC GTT CGT ACA CTT GTC CCG ACC          2685
Thr Val Phe Gly Asp Pro Ser Leu Leu Val Arg Thr Leu Val Pro Thr
565                 570                 575

AAA ATG CAG GTT ACG GCT CCG GCT CAG ATT AAT TTG ACG GAT GCT TCA      2733
Lys Met Gln Val Thr Ala Pro Ala Gln Ile Asn Leu Thr Asp Ala Ser
580                 585                 590                 595

GTC AAC GTA TCT TGC GAT TAT AAT GGT GCT ATT GCT ACC ATT TCA GCC      2781
Val Asn Val Ser Cys Asp Tyr Asn Gly Ala Ile Ala Thr Ile Ser Ala
                600                 605                 610

AAT GGA AAG ATG TTC GGT TCT GCA GTT GTC GAA AAT GGA ACA GCT ACA      2829
Asn Gly Lys Met Phe Gly Ser Ala Val Val Glu Asn Gly Thr Ala Thr
            615                 620                 625

ATC AAT CTG ACA GGT CTG ACA AAT GAA AGC ACG CTT ACC CTT ACA GTA      2877
Ile Asn Leu Thr Gly Leu Thr Asn Glu Ser Thr Leu Thr Leu Thr Val
        630                 635                 640

GTT GGT TAC AAC AAA GAG ACG GTT ATT AAG ACC ATC AAC ACT AAT GGT      2925
Val Gly Tyr Asn Lys Glu Thr Val Ile Lys Thr Ile Asn Thr Asn Gly
    645                 650                 655

GAG CCT AAC CCC TAC CAG CCC GTT TCC AAC TTG ACA GCT ACA ACG CAG      2973
Glu Pro Asn Pro Tyr Gln Pro Val Ser Asn Leu Thr Ala Thr Thr Gln
660                 665                 670                 675

GGT CAG AAA GTA ACG CTC AAG TGG GAT GCA CCG AGC ACG AAA ACC AAT      3021
Gly Gln Lys Val Thr Leu Lys Trp Asp Ala Pro Ser Thr Lys Thr Asn
                680                 685                 690

GCA ACC ACT AAT ACC GCT CGC AGC GTG GAT GGC ATA CGA GAA TTG GTT      3069
Ala Thr Thr Asn Thr Ala Arg Ser Val Asp Gly Ile Arg Glu Leu Val
            695                 700                 705

CTT CTG TCA GTC AGC GAT GCC CCC GAA CTT CTT CGC AGC GGT CAG GCC      3117
Leu Leu Ser Val Ser Asp Ala Pro Glu Leu Leu Arg Ser Gly Gln Ala
        710                 715                 720

GAG ATT GTT CTT GAA GCT CAC GAT GTT TGG AAT GAT GGA TCC GGT TAT      3165
Glu Ile Val Leu Glu Ala His Asp Val Trp Asn Asp Gly Ser Gly Tyr
    725                 730                 735

CAG ATT CTT TTG GAT GCA GAC CAT GAT CAA TAT GGA CAG GTT ATA CCC      3213
Gln Ile Leu Leu Asp Ala Asp His Asp Gln Tyr Gly Gln Val Ile Pro
740                 745                 750                 755

AGT GAT ACC CAT ACT CTT TGG CCG AAC TGT AGT GTC CCG GCC AAT CTG      3261
Ser Asp Thr His Thr Leu Trp Pro Asn Cys Ser Val Pro Ala Asn Leu
                760                 765                 770

TTC GCT CCG TTC GAA TAT ACT GTT CCG GAA AAT GCA GAT CCT TCT TGT      3309
Phe Ala Pro Phe Glu Tyr Thr Val Pro Glu Asn Ala Asp Pro Ser Cys
            775                 780                 785
```

```
TCC CCT ACC AAT ATG ATA ATG GAT GGT ACT GCA TCC GTT AAT ATA CCG        3357
Ser Pro Thr Asn Met Ile Met Asp Gly Thr Ala Ser Val Asn Ile Pro
        790                 795                 800

GCC GGA ACT TAT GAC TTT GCA ATT GCT GCT CCT CAA GCA AAT GCA AAG        3405
Ala Gly Thr Tyr Asp Phe Ala Ile Ala Ala Pro Gln Ala Asn Ala Lys
        805                 810                 815

ATT TGG ATT GCC GGA CAA GGA CCG ACG AAA GAA GAT GAT TAT GTA TTT        3453
Ile Trp Ile Ala Gly Gln Gly Pro Thr Lys Glu Asp Asp Tyr Val Phe
820                 825                 830                 835

GAA GCC GGT AAA AAA TAC CAT TTC CTT ATG AAG AAG ATG GGT AGC GGT        3501
Glu Ala Gly Lys Lys Tyr His Phe Leu Met Lys Lys Met Gly Ser Gly
                840                 845                 850

GAT GGA ACT GAA TTG ACT ATA AGC GAA GGT GGT GGA AGC GAT TAC ACC        3549
Asp Gly Thr Glu Leu Thr Ile Ser Glu Gly Gly Gly Ser Asp Tyr Thr
                855                 860                 865

TAT ACT GTC TAT CGT GAC GGC ACG AAG ATC AAG GAA GGT CTG ACG GCT        3597
Tyr Thr Val Tyr Arg Asp Gly Thr Lys Ile Lys Glu Gly Leu Thr Ala
                870                 875                 880

ACG ACA TTC GAA GAA GAC GGT GTA GCT ACG GGC AAT CAT GAG TAT TGC        3645
Thr Thr Phe Glu Glu Asp Gly Val Ala Thr Gly Asn His Glu Tyr Cys
        885                 890                 895

GTG GAA GTT AAG TAC ACA GCC GGC GTA TCT CCG AAG GTA TGT AAA GAC        3693
Val Glu Val Lys Tyr Thr Ala Gly Val Ser Pro Lys Val Cys Lys Asp
900                 905                 910                 915

GTT ACG GTA GAA GGA TCC AAT GAA TTT GCT CCT GTA CAG AAC CTG ACC        3741
Val Thr Val Glu Gly Ser Asn Glu Phe Ala Pro Val Gln Asn Leu Thr
                920                 925                 930

GGT AGT GCA GTC GGC CAG AAA GTA ACG CTC AAG TGG GAT GCA CCT AAT        3789
Gly Ser Ala Val Gly Gln Lys Val Thr Leu Lys Trp Asp Ala Pro Asn
                935                 940                 945

GGT ACC CCG AAT CCA AAT CCG AAT CCG AAT CCG AAT CCC GGA ACA ACA        3837
Gly Thr Pro Asn Pro Asn Pro Asn Pro Asn Pro Asn Pro Gly Thr Thr
                950                 955                 960

ACA CTT TCC GAA TCA TTC GAA AAT GGT ATT CCT GCC TCA TGG AAG ACG        3885
Thr Leu Ser Glu Ser Phe Glu Asn Gly Ile Pro Ala Ser Trp Lys Thr
        965                 970                 975

ATC GAT GCA GAC GGT GAC GGG CAT GGC TGG AAG CCT GGA AAT GCT CCC        3933
Ile Asp Ala Asp Gly Asp Gly His Gly Trp Lys Pro Gly Asn Ala Pro
980                 985                 990                 995

GGA ATC GCT GGC TAC AAT AGC AAT GGT TGT GTA TAT TCA GAG TCA TTC        3981
Gly Ile Ala Gly Tyr Asn Ser Asn Gly Cys Val Tyr Ser Glu Ser Phe
                1000                1005                1010

GGT CTT GGT GGT ATA GGA GTT CTT ACC CCT GAC AAC TAT CTG ATA ACA        4029
Gly Leu Gly Gly Ile Gly Val Leu Thr Pro Asp Asn Tyr Leu Ile Thr
                1015                1020                1025

CCG GCA TTG GAT TTG CCT AAC GGA GGT AAG TTG ACT TTC TGG GTA TGC        4077
Pro Ala Leu Asp Leu Pro Asn Gly Gly Lys Leu Thr Phe Trp Val Cys
                1030                1035                1040

GCA CAG GAT GCT AAT TAT GCA TCC GAG CAC TAT GCG GTG TAT GCA TCT        4125
Ala Gln Asp Ala Asn Tyr Ala Ser Glu His Tyr Ala Val Tyr Ala Ser
        1045                1050                1055

TCG ACC GGT AAC GAT GCA TCC AAC TTC ACG AAT GCT TTG TTG GAA GAG        4173
Ser Thr Gly Asn Asp Ala Ser Asn Phe Thr Asn Ala Leu Leu Glu Glu
1060                1065                1070                1075

ACG ATT ACG GCA AAA GGT GTT CGC TCG CCG GAA GCT ATT CGT GGT CGT        4221
Thr Ile Thr Ala Lys Gly Val Arg Ser Pro Glu Ala Ile Arg Gly Arg
                1080                1085                1090

ATA CAG GGT ACT TGG CGC CAG AAG ACG GTA GAC CTT CCC GCA GGT ACG        4269
Ile Gln Gly Thr Trp Arg Gln Lys Thr Val Asp Leu Pro Ala Gly Thr
```

-continued

```
                  1095                1100                1105
AAA TAT GTT GCT TTC CGT CAC TTC CAA AGC ACG GAT ATG TTC TAC ATC          4317
Lys Tyr Val Ala Phe Arg His Phe Gln Ser Thr Asp Met Phe Tyr Ile
        1110                1115                1120

GAC CTT GAT GAG GTT GAG ATC AAG GCC AAC GGC AAG CGC GCA GAC TTC          4365
Asp Leu Asp Glu Val Glu Ile Lys Ala Asn Gly Lys Arg Ala Asp Phe
    1125                1130                1135

ACG GAA ACG TTC GAG TCT TCT ACT CAT GGA GAG GCA CCG GCG GAA TGG          4413
Thr Glu Thr Phe Glu Ser Ser Thr His Gly Glu Ala Pro Ala Glu Trp
1140                1145                1150                1155

ACT ACT ATC GAT GCC GAT GGC GAT GGT CAG GGT TGG CTC TGT CTG TCT          4461
Thr Thr Ile Asp Ala Asp Gly Asp Gly Gln Gly Trp Leu Cys Leu Ser
                1160                1165                1170

TCC GGA CAA TTG GAC TGG CTG ACA GCT CAT GGC GGC ACC AAC GTA GTA          4509
Ser Gly Gln Leu Asp Trp Leu Thr Ala His Gly Gly Thr Asn Val Val
            1175                1180                1185

GCC TCT TTC TCA TGG AAT GGA ATG GCT TTG AAT CCT GAT AAC TAT CTC          4557
Ala Ser Phe Ser Trp Asn Gly Met Ala Leu Asn Pro Asp Asn Tyr Leu
        1190                1195                1200

ATC TCA AAG GAT GTT ACA GGC GCA ACG AAG GTA AAG TAC TAC TAT GCA          4605
Ile Ser Lys Asp Val Thr Gly Ala Thr Lys Val Lys Tyr Tyr Tyr Ala
    1205                1210                1215

GTC AAC GAC GGT TTT CCC GGG GAT CAC TAT GCG GTG ATG ATC TCC AAG          4653
Val Asn Asp Gly Phe Pro Gly Asp His Tyr Ala Val Met Ile Ser Lys
1220                1225                1230                1235

ACG GGC ACG AAC GCC GGA GAC TTC ACG GTT GTT TTC GAA GAA ACG CCT          4701
Thr Gly Thr Asn Ala Gly Asp Phe Thr Val Val Phe Glu Glu Thr Pro
                1240                1245                1250

AAC GGA ATA AAT AAG GGC GGA GCA AGA TTC GGT CTT TCC ACG GAA GCC          4749
Asn Gly Ile Asn Lys Gly Gly Ala Arg Phe Gly Leu Ser Thr Glu Ala
            1255                1260                1265

AAT GGC GCC AAA CCT CAA AGT GTA TGG ATC GAG CGT ACG GTA GAT TTG          4797
Asn Gly Ala Lys Pro Gln Ser Val Trp Ile Glu Arg Thr Val Asp Leu
        1270                1275                1280

CCT GCG GGC ACG AAG TAT GTT GCT TTC CGT CAC TAC AAT TGC TCG GAT          4845
Pro Ala Gly Thr Lys Tyr Val Ala Phe Arg His Tyr Asn Cys Ser Asp
    1285                1290                1295

TTG AAC TAC ATT CTT TTG GAT GAT ATT CAG TTC ACC ATG GGT GGC AGC          4893
Leu Asn Tyr Ile Leu Leu Asp Asp Ile Gln Phe Thr Met Gly Gly Ser
1300                1305                1310                1315

CCC ACC CCG ACC GAT TAT ACC TAC ACG GTG TAT CGT GAC GGT ACG AAG          4941
Pro Thr Pro Thr Asp Tyr Thr Tyr Thr Val Tyr Arg Asp Gly Thr Lys
                1320                1325                1330

ATC AAG GAA GGT CTG ACC GAA ACG ACC TTC GAA GAA GAC GGC GTA GCT          4989
Ile Lys Glu Gly Leu Thr Glu Thr Thr Phe Glu Glu Asp Gly Val Ala
            1335                1340                1345

ACA GGC AAT CAT GAG TAT TGC GTG GAA GTG AAG TAC ACA GCC GGC GTA          5037
Thr Gly Asn His Glu Tyr Cys Val Glu Val Lys Tyr Thr Ala Gly Val
        1350                1355                1360

TCT CCG AAA GAG TGC GTA AAC GTA ACT ATT AAT CCG ACT CAG TTC AAT          5085
Ser Pro Lys Glu Cys Val Asn Val Thr Ile Asn Pro Thr Gln Phe Asn
    1365                1370                1375

CCT GTA AAG AAC CTG AAG GCA CAA CCG GAT GGC GGC GAC GTG GTT CTC          5133
Pro Val Lys Asn Leu Lys Ala Gln Pro Asp Gly Gly Asp Val Val Leu
1380                1385                1390                1395

AAG TGG GAA GCC CCG AGC GCA AAA AAG ACA GAA GGT TCT CGT GAA GTA          5181
Lys Trp Glu Ala Pro Ser Ala Lys Lys Thr Glu Gly Ser Arg Glu Val
                1400                1405                1410

AAA CGG ATC GGA GAC GGT CTT TTC GTT ACG ATC GAA CCT GCA AAC GAT          5229
```

```
                                        -continued

Lys Arg Ile Gly Asp Gly Leu Phe Val Thr Ile Glu Pro Ala Asn Asp
        1415                1420                1425

GTA CGT GCC AAC GAA GCC AAG GTT GTG CTC GCA GCA GAC AAC GTA TGG    5277
Val Arg Ala Asn Glu Ala Lys Val Val Leu Ala Ala Asp Asn Val Trp
        1430                1435                1440

GGA GAC AAT ACG GGT TAC CAG TTC TTG TTG GAT GCC GAT CAC AAT ACA    5325
Gly Asp Asn Thr Gly Tyr Gln Phe Leu Leu Asp Ala Asp His Asn Thr
        1445                1450                1455

TTC GGA AGT GTC ATT CCG GCA ACC GGT CCT CTC TTT ACC GGA ACA GCT    5373
Phe Gly Ser Val Ile Pro Ala Thr Gly Pro Leu Phe Thr Gly Thr Ala
1460                1465                1470                1475

TCT TCC AAT CTT TAC AGT GCG AAC TTC GAG TAT TTG ATC CCG GCC AAT    5421
Ser Ser Asn Leu Tyr Ser Ala Asn Phe Glu Tyr Leu Ile Pro Ala Asn
                1480                1485                1490

GCC GAT CCT GTT GTT ACT ACA CAG AAT ATT ATC GTT ACA GGA CAG GGT    5469
Ala Asp Pro Val Val Thr Thr Gln Asn Ile Ile Val Thr Gly Gln Gly
                    1495                1500                1505

GAA GTT GTA ATC CCC GGT GGT GTT TAC GAC TAT TGC ATT ACG AAC CCG    5517
Glu Val Val Ile Pro Gly Gly Val Tyr Asp Tyr Cys Ile Thr Asn Pro
                        1510                1515                1520

GAA CCT GCA TCC GGA AAG ATG TGG ATC GCA GGA GAT GGA GGC AAC CAG    5565
Glu Pro Ala Ser Gly Lys Met Trp Ile Ala Gly Asp Gly Gly Asn Gln
                            1525                1530                1535

CCT GCA CGT TAT GAC GAT TTC ACA TTC GAA GCA GGC AAG AAG TAC ACC    5613
Pro Ala Arg Tyr Asp Asp Phe Thr Phe Glu Ala Gly Lys Lys Tyr Thr
1540                1545                1550                1555

TTC ACG ATG CGT CGC GCC GGA ATG GGA GAT GGA ACT GAT ATG GAA GTC    5661
Phe Thr Met Arg Arg Ala Gly Met Gly Asp Gly Thr Asp Met Glu Val
                1560                1565                1570

GAA GAC GAT TCA CCT GCA AGC TAT ACC TAT ACA GTC TAT CGT GAC GGC    5709
Glu Asp Asp Ser Pro Ala Ser Tyr Thr Tyr Thr Val Tyr Arg Asp Gly
                    1575                1580                1585

ACG AAG ATC AAG GAA GGT CTG ACC GAA ACG ACC TAC CGC GAT GCA GGA    5757
Thr Lys Ile Lys Glu Gly Leu Thr Glu Thr Thr Tyr Arg Asp Ala Gly
                        1590                1595                1600

ATG AGT GCA CAA TCT CAT GAG TAT TGC GTA GAG GTT AAG TAC GCA GCC    5805
Met Ser Ala Gln Ser His Glu Tyr Cys Val Glu Val Lys Tyr Ala Ala
                            1605                1610                1615

GGC GTA TCT CCG AAG GTT TGT GTG GAT TAT ATT CCT GAC GGA GTG GCA    5853
Gly Val Ser Pro Lys Val Cys Val Asp Tyr Ile Pro Asp Gly Val Ala
1620                1625                1630                1635

GAC GTA ACG GCT CAG AAG CCT TAC ACG CTG ACA GTT GTT GGA AAG ACG    5901
Asp Val Thr Ala Gln Lys Pro Tyr Thr Leu Thr Val Val Gly Lys Thr
                1640                1645                1650

ATC ACG GTA ACT TGC CAA GGC GAA GCT ATG ATC TAC GAC ATG AAC GGT    5949
Ile Thr Val Thr Cys Gln Gly Glu Ala Met Ile Tyr Asp Met Asn Gly
                    1655                1660                1665

CGT CGT CTG GCA GCC GGT CGC AAC ACA GTT GTT TAC ACG GCT CAG GGC    5997
Arg Arg Leu Ala Ala Gly Arg Asn Thr Val Val Tyr Thr Ala Gln Gly
                        1670                1675                1680

GGC TAC TAT GCA GTC ATG GTT GTC GTT GAC GGC AAG TCT TAC GTA GAG    6045
Gly Tyr Tyr Ala Val Met Val Val Val Asp Gly Lys Ser Tyr Val Glu
                            1685                1690                1695

AAA CTC GCT GTA AAG TAA TTCTGTCTTG GACTCGGAGA CTTTGTGCAG            6093
Lys Leu Ala Val Lys *
1700                1705

ACACTTTTAA TATAGGTCTG TAATTGTCTC AGAGTATGAA TCGATCGCCC GACCTCCTTT   6153

TAAGGAAGTC TGGGCGACTT CGTTTTTATG CCTATTATTC TAATATACTT CTGAAACAAT   6213
```

```
TTGTTCCAAA AAGTTGCATG AAAAGATTAT CTTACTATCT TTGCACTGCA AAAGGGGAGT    6273

TTCCTAAGGT TTTCCCCGGA GTAGTACGGT AATAACGGTG TGGTAGTTCA GCTGGTTAGA    6333

ATACCTGCCT GTCACGCAGG GGGTCGCGGG TTCGAGTCCC GTCCATACCG CTAAATAGCT    6393

GAAAGATAGG CTATAGGTCA TCTGAAGCAA TTTTAGAAAC GAATCCAAAA GCGTCTTAAT    6453

TCCAACGAAT TAAGGCGCTT TTTCTTTGTC GCCACCCCAC ACGTCGGATG AGGTTCGGAA    6513

TAGGCGTATA TTCCGTAAAT ATGCCTCCGG TGGTTCCATT TTGGTTACAA AAACAAAGG    6573

GGCTGAAAAT TGTAACCACA GACGACGTTA AGACGATGTT TAGACGATTG ACAAATTACT    6633

CTGTTTCAAA ATCATATGTC GAACTTTGTA GCCGTATGGT TACACTAATT TTGGAGCAAA    6693

ATGAAGAGTC AATTTCGTTC AGTTTTTTAC TTGCGCAGCA ATTACATCAA CAAAGAAGGT    6753

AAAACTCCTG TCCTTATTCG TATTTATCTG AATAAGGAAC GCCTGTCGTT GGGTTCGACA    6813

GGGCTGGCTG TTAATCCCAT ACAATGGGAT TCAGAAAAAG AGAAAGTCAA AGGACATAGT    6873

GCAGAAGCAC TTGAAGTCAA TCGAAAGATC GAAGAAATCA GGGCTGATAT TCTGACCATT    6933

TACAAACGTT TGGAAGTAAC AGTAGATGAT TTGACGCCGG AGAGGATCAA ATCGGAATAC    6993

TGCGGACAGA CGGATACATT AAACAGTATA GTGGAACTTT TCGATAAACA TAACGAGGAT    7053

GTCCGGGCCC AGGTGGGAAT CAATAAAACG GCTGCCACTT TACAAAAATA CGAAAACAGC    7113

AAACGGCATT TTACCCGATT CCTCAAAGCG AAGTACAACA GAACGGATCT CAAATTCTCA    7173

GAGCTTACCC CGTTGGTCAT TCATAACTTT GAGATATATC TGCTGACTGT AGCCCATTGT    7233

TGCCCGAATA CGGCAACCAA AATCTTGAAG CTT                                 7266
```

(2) INFORMATION FOR SEQ ID NO:10:

(i) SEQUENCE CHARACTERISTICS:
        (A) LENGTH: 1705 amino acids
        (B) TYPE: amino acid
        (D) TOPOLOGY: linear (ii) MOLECULE TYPE: protein (xi) SEQUENCE DESCRIPTION: SEQ ID NO:10:

```
Met Lys Asn Leu Asn Lys Phe Val Ser Ile Ala Leu Cys Ser Ser Leu
 1               5                  10                  15

Leu Gly Gly Met Ala Phe Ala Gln Gln Thr Glu Leu Gly Arg Asn Pro
                20                  25                  30

Asn Val Arg Leu Leu Glu Ser Thr Gln Ser Val Thr Lys Val Gln
         35                  40                  45

Phe Arg Met Asp Asn Leu Lys Phe Thr Glu Val Gln Thr Pro Lys Gly
     50                  55                  60

Ile Gly Gln Val Pro Thr Tyr Thr Glu Gly Val Asn Leu Ser Glu Lys
 65                  70                  75                  80

Gly Met Pro Thr Leu Pro Ile Leu Ser Arg Ser Leu Ala Val Ser Asp
                85                  90                  95

Thr Arg Glu Met Lys Val Glu Val Ser Ser Lys Phe Ile Glu Lys
             100                 105                 110

Lys Asn Val Leu Ile Ala Pro Ser Lys Gly Met Ile Met Arg Asn Glu
         115                 120                 125

Asp Pro Lys Lys Ile Pro Tyr Val Tyr Gly Lys Ser Tyr Ser Gln Asn
     130                 135                 140

Lys Phe Phe Pro Gly Glu Ile Ala Thr Leu Asp Asp Pro Phe Ile Leu
145                 150                 155                 160
```

```
Arg Asp Val Arg Gly Gln Val Val Asn Phe Ala Pro Leu Gln Tyr Asn
                165                 170                 175
Pro Val Thr Lys Thr Leu Arg Ile Tyr Thr Glu Ile Thr Val Ala Val
            180                 185                 190
Ser Glu Thr Ser Glu Gln Gly Lys Asn Ile Leu Asn Lys Lys Gly Thr
        195                 200                 205
Phe Ala Gly Phe Glu Asp Thr Tyr Lys Arg Met Phe Met Asn Tyr Glu
    210                 215                 220
Pro Gly Arg Tyr Thr Pro Val Glu Glu Lys Gln Asn Gly Arg Met Ile
225                 230                 235                 240
Val Ile Val Ala Lys Lys Tyr Glu Gly Asp Ile Lys Asp Phe Val Asp
                245                 250                 255
Trp Lys Asn Gln Arg Gly Leu Arg Thr Glu Val Lys Val Ala Glu Asp
                260                 265                 270
Ile Ala Ser Pro Val Thr Ala Asn Ala Ile Gln Gln Phe Val Lys Gln
            275                 280                 285
Glu Tyr Glu Lys Glu Gly Asn Asp Leu Thr Tyr Val Leu Leu Val Gly
        290                 295                 300
Asp His Lys Asp Ile Pro Ala Lys Ile Thr Pro Gly Ile Lys Ser Asp
305                 310                 315                 320
Gln Val Tyr Gly Gln Ile Val Gly Asn Asp His Tyr Asn Glu Val Phe
                325                 330                 335
Ile Gly Arg Phe Ser Cys Glu Ser Lys Glu Asp Leu Lys Thr Gln Ile
                340                 345                 350
Asp Arg Thr Ile His Tyr Glu Arg Asn Ile Thr Thr Glu Asp Lys Trp
            355                 360                 365
Leu Gly Gln Ala Leu Cys Ile Ala Ser Ala Glu Gly Pro Ser Ala
        370                 375                 380
Asp Asn Gly Glu Ser Asp Ile Gln His Glu Asn Val Ile Ala Asn Leu
385                 390                 395                 400
Leu Thr Gln Tyr Gly Tyr Thr Lys Ile Ile Lys Cys Tyr Asp Pro Gly
                405                 410                 415
Val Thr Pro Lys Asn Ile Ile Asp Ala Phe Asn Gly Gly Ile Ser Leu
                420                 425                 430
Val Asn Tyr Thr Gly His Gly Ser Glu Thr Ala Trp Gly Thr Ser His
            435                 440                 445
Phe Gly Thr Thr His Val Lys Gln Leu Thr Asn Ser Asn Gln Leu Pro
    450                 455                 460
Phe Ile Phe Asp Val Ala Cys Val Asn Gly Asp Phe Leu Phe Ser Met
465                 470                 475                 480
Pro Cys Phe Ala Glu Ala Leu Met Arg Ala Gln Lys Asp Gly Lys Pro
                485                 490                 495
Thr Gly Thr Val Ala Ile Ile Ala Ser Thr Ile Asn Gln Ser Trp Ala
            500                 505                 510
Ser Pro Met Arg Gly Gln Asp Glu Met Asn Glu Ile Leu Cys Glu Lys
        515                 520                 525
His Pro Asn Asn Ile Lys Arg Thr Phe Gly Gly Val Thr Met Asn Gly
    530                 535                 540
Met Phe Ala Met Val Glu Lys Tyr Lys Lys Asp Gly Glu Lys Met Leu
545                 550                 555                 560
Asp Thr Trp Thr Val Phe Gly Asp Pro Ser Leu Leu Val Arg Thr Leu
                565                 570                 575
Val Pro Thr Lys Met Gln Val Thr Ala Pro Ala Gln Ile Asn Leu Thr
```

-continued

```
            580                 585                 590
Asp Ala Ser Val Asn Val Ser Cys Asp Tyr Asn Gly Ala Ile Ala Thr
            595                 600                 605
Ile Ser Ala Asn Gly Lys Met Phe Gly Ser Ala Val Val Glu Asn Gly
            610                 615                 620
Thr Ala Thr Ile Asn Leu Thr Gly Leu Thr Asn Glu Ser Thr Leu Thr
625                 630                 635                 640
Leu Thr Val Val Gly Tyr Asn Lys Glu Thr Val Ile Lys Thr Ile Asn
                645                 650                 655
Thr Asn Gly Glu Pro Asn Pro Tyr Gln Pro Val Ser Asn Leu Thr Ala
                660                 665                 670
Thr Thr Gln Gly Gln Lys Val Thr Leu Lys Trp Asp Ala Pro Ser Thr
                675                 680                 685
Lys Thr Asn Ala Thr Thr Asn Thr Ala Arg Ser Val Asp Gly Ile Arg
                690                 695                 700
Glu Leu Val Leu Leu Ser Val Ser Asp Ala Pro Glu Leu Leu Arg Ser
705                 710                 715                 720
Gly Gln Ala Glu Ile Val Leu Glu Ala His Asp Val Trp Asn Asp Gly
                725                 730                 735
Ser Gly Tyr Gln Ile Leu Leu Asp Ala Asp His Asp Gln Tyr Gly Gln
                740                 745                 750
Val Ile Pro Ser Asp Thr His Thr Leu Trp Pro Asn Cys Ser Val Pro
                755                 760                 765
Ala Asn Leu Phe Ala Pro Phe Glu Tyr Thr Val Pro Glu Asn Ala Asp
                770                 775                 780
Pro Ser Cys Ser Pro Thr Asn Met Ile Met Asp Gly Thr Ala Ser Val
785                 790                 795                 800
Asn Ile Pro Ala Gly Thr Tyr Asp Phe Ala Ile Ala Ala Pro Gln Ala
                805                 810                 815
Asn Ala Lys Ile Trp Ile Ala Gly Gln Gly Pro Thr Lys Glu Asp Asp
                820                 825                 830
Tyr Val Phe Glu Ala Gly Lys Lys Tyr His Phe Leu Met Lys Lys Met
                835                 840                 845
Gly Ser Gly Asp Gly Thr Glu Leu Thr Ile Ser Glu Gly Gly Gly Ser
850                 855                 860
Asp Tyr Thr Tyr Thr Val Tyr Arg Asp Gly Thr Lys Ile Lys Glu Gly
865                 870                 875                 880
Leu Thr Ala Thr Thr Phe Glu Glu Asp Gly Val Ala Thr Gly Asn His
                885                 890                 895
Glu Tyr Cys Val Glu Val Lys Tyr Thr Ala Gly Val Ser Pro Lys Val
                900                 905                 910
Cys Lys Asp Val Thr Val Glu Gly Ser Asn Glu Phe Ala Pro Val Gln
                915                 920                 925
Asn Leu Thr Gly Ser Ala Val Gly Gln Lys Val Thr Leu Lys Trp Asp
                930                 935                 940
Ala Pro Asn Gly Thr Pro Asn Pro Asn Pro Asn Pro Asn Pro Asn Pro
945                 950                 955                 960
Gly Thr Thr Thr Leu Ser Glu Ser Phe Glu Asn Gly Ile Pro Ala Ser
                965                 970                 975
Trp Lys Thr Ile Asp Ala Asp Gly Asp Gly His Gly Trp Lys Pro Gly
                980                 985                 990
Asn Ala Pro Gly Ile Ala Gly Tyr Asn Ser Asn Gly Cys Val Tyr Ser
                995                 1000                1005
```

```
Glu Ser Phe Gly Leu Gly Gly Ile Gly Val Leu Thr Pro Asp Asn Tyr
    1010                1015                1020
Leu Ile Thr Pro Ala Leu Asp Leu Pro Asn Gly Gly Lys Leu Thr Phe
1025                1030                1035                1040
Trp Val Cys Ala Gln Asp Ala Asn Tyr Ala Ser Glu His Tyr Ala Val
                1045                1050                1055
Tyr Ala Ser Ser Thr Gly Asn Asp Ala Ser Asn Phe Thr Asn Ala Leu
                1060                1065                1070
Leu Glu Glu Thr Ile Thr Ala Lys Gly Val Arg Ser Pro Glu Ala Ile
            1075                1080                1085
Arg Gly Arg Ile Gln Gly Thr Trp Arg Gln Lys Thr Val Asp Leu Pro
    1090                1095                1100
Ala Gly Thr Lys Tyr Val Ala Phe Arg His Phe Gln Ser Thr Asp Met
1105                1110                1115                1120
Phe Tyr Ile Asp Leu Asp Glu Val Glu Ile Lys Ala Asn Gly Lys Arg
                1125                1130                1135
Ala Asp Phe Thr Glu Thr Phe Glu Ser Ser Thr His Gly Glu Ala Pro
                1140                1145                1150
Ala Glu Trp Thr Thr Ile Asp Ala Asp Gly Asp Gly Gln Gly Trp Leu
            1155                1160                1165
Cys Leu Ser Ser Gly Gln Leu Asp Trp Leu Thr Ala His Gly Gly Thr
    1170                1175                1180
Asn Val Val Ala Ser Phe Ser Trp Asn Gly Met Ala Leu Asn Pro Asp
1185                1190                1195                1200
Asn Tyr Leu Ile Ser Lys Asp Val Thr Gly Ala Thr Lys Val Lys Tyr
                1205                1210                1215
Tyr Tyr Ala Val Asn Asp Gly Phe Pro Gly Asp His Tyr Ala Val Met
                1220                1225                1230
Ile Ser Lys Thr Gly Thr Asn Ala Gly Asp Phe Thr Val Val Phe Glu
            1235                1240                1245
Glu Thr Pro Asn Gly Ile Asn Lys Gly Gly Ala Arg Phe Gly Leu Ser
    1250                1255                1260
Thr Glu Ala Asn Gly Ala Lys Pro Gln Ser Val Trp Ile Glu Arg Thr
1265                1270                1275                1280
Val Asp Leu Pro Ala Gly Thr Lys Tyr Val Ala Phe Arg His Tyr Asn
                1285                1290                1295
Cys Ser Asp Leu Asn Tyr Ile Leu Leu Asp Asp Ile Gln Phe Thr Met
                1300                1305                1310
Gly Gly Ser Pro Thr Pro Thr Asp Tyr Thr Tyr Thr Val Tyr Arg Asp
            1315                1320                1325
Gly Thr Lys Ile Lys Glu Gly Leu Thr Glu Thr Phe Glu Glu Asp
    1330                1335                1340
Gly Val Ala Thr Gly Asn His Glu Tyr Cys Val Glu Val Lys Tyr Thr
1345                1350                1355                1360
Ala Gly Val Ser Pro Lys Glu Cys Val Asn Val Thr Ile Asn Pro Thr
                1365                1370                1375
Gln Phe Asn Pro Val Lys Asn Leu Lys Ala Gln Pro Asp Gly Gly Asp
                1380                1385                1390
Val Val Leu Lys Trp Glu Ala Pro Ser Ala Lys Lys Thr Glu Gly Ser
            1395                1400                1405
Arg Glu Val Lys Arg Ile Gly Asp Gly Leu Phe Val Thr Ile Glu Pro
    1410                1415                1420
```

```
Ala Asn Asp Val Arg Ala Asn Glu Ala Lys Val Val Leu Ala Ala Asp
1425                1430                1435                1440

Asn Val Trp Gly Asp Asn Thr Gly Tyr Gln Phe Leu Leu Asp Ala Asp
                1445                1450                1455

His Asn Thr Phe Gly Ser Val Ile Pro Ala Thr Gly Pro Leu Phe Thr
            1460                1465                1470

Gly Thr Ala Ser Ser Asn Leu Tyr Ser Ala Asn Phe Glu Tyr Leu Ile
        1475                1480                1485

Pro Ala Asn Ala Asp Pro Val Val Thr Thr Gln Asn Ile Ile Val Thr
    1490                1495                1500

Gly Gln Gly Glu Val Val Ile Pro Gly Gly Val Tyr Asp Tyr Cys Ile
1505                1510                1515                1520

Thr Asn Pro Glu Pro Ala Ser Gly Lys Met Trp Ile Ala Gly Asp Gly
                1525                1530                1535

Gly Asn Gln Pro Ala Arg Tyr Asp Asp Phe Thr Phe Glu Ala Gly Lys
            1540                1545                1550

Lys Tyr Thr Phe Thr Met Arg Arg Ala Gly Met Gly Asp Gly Thr Asp
        1555                1560                1565

Met Glu Val Glu Asp Asp Ser Pro Ala Ser Tyr Thr Tyr Thr Val Tyr
    1570                1575                1580

Arg Asp Gly Thr Lys Ile Lys Glu Gly Leu Thr Glu Thr Thr Tyr Arg
1585                1590                1595                1600

Asp Ala Gly Met Ser Ala Gln Ser His Glu Tyr Cys Val Glu Val Lys
                1605                1610                1615

Tyr Ala Ala Gly Val Ser Pro Lys Val Cys Val Asp Tyr Ile Pro Asp
            1620                1625                1630

Gly Val Ala Asp Val Thr Ala Gln Lys Pro Tyr Thr Leu Thr Val Val
        1635                1640                1645

Gly Lys Thr Ile Thr Val Thr Cys Gln Gly Glu Ala Met Ile Tyr Asp
    1650                1655                1660

Met Asn Gly Arg Arg Leu Ala Ala Gly Arg Asn Thr Val Val Tyr Thr
1665                1670                1675                1680

Ala Gln Gly Gly Tyr Tyr Ala Val Met Val Val Val Asp Gly Lys Ser
                1685                1690                1695

Tyr Val Glu Lys Leu Ala Val Lys   *
            1700                1705

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:11:

Ser Cys Asp Tyr Asn Gly Ala Ile Ala Thr Ile Ser Ala
1               5                   10

(2) INFORMATION FOR SEQ ID NO:12:
```

```
    (i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:12:

Ser Cys Trp Ala Phe Ser Gly Val Ala Ala Thr Phe Ser Ala
1               5                  10

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:13:

Ser Cys Trp Ile Phe Ser Thr Ile Gly Ala Leu Phe Ser Ala
1               5                  10

(2) INFORMATION FOR SEQ ID NO:14:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:14:

Gly Cys Trp Ala Phe Ser Ala Ile Ala Thr Val Glu Gly Ile
1               5                  10

(2) INFORMATION FOR SEQ ID NO:15:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:15:

Ser Cys Trp Ala Phe Ser Ala Val Val Thr Ile Phe Gly Ile
1               5                  10

(2) INFORMATION FOR SEQ ID NO:16:
```

```
    (i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:16:

Ser Cys Trp Ala Phe Gly Ala Val Glu Ala Ile Ser Asp Arg
1               5                   10
```

PORPHYROMONAS GINGIVALIS ARGININE-SPECIFIC PROTEINASE CODING SEQUENCES

This application is a continuation of U.S. patent application Ser. No. 08/336,308 filed Nov. 8, 1994, now U.S. Pat. No. 6,017,523, which is a continuation-in-part of PCT/US94/10283 filed Sep. 9, 1994, which is a continuation of U.S. patent application Ser. No. 08/265,441 filed Jun. 24, 1994, now abandoned which is a Continuation-in-Part of U.S. patent application Ser. No. 08/119,361, filed Sep. 10, 1993 now U.S. Pat. No. 5,523,390.

This invention was made, at least in part, with funding from the National Institutes of Health (Grant Nos. DE 09761, HL 26148 and HL 37090). Accordingly, the United States Government may have certain rights in this invention.

FIELD OF THE INVENTION

The field of this invention is bacterial proteases, more particularly those of *Porphyromonas gingivalis*, most particularly the arginine-specific proteases termed Arg-gingipains herein and the nucleotide sequences encoding same.

BACKGROUND OF THE INVENTION

*Porphyromonas gingivalis* (formerly *Bacteroides gingivalis*) is an obligately anaerobic bacterium which is implicated in periodontal disease. *P. gingivalis* produces proteolytic enzymes in relatively large quantities; these proteinases are recognized as important virulence factors (Smalley et al. (1989) *Oral Microbiol. Immun.* 4, 178–179; Marsh et al. (1989) *FEMS Microbiol, Lett.* 59, 181–186; Grenier and Mayrand (1987) *J. Clin. Microbiol,* 25, 738–740]. A number of physiologically significant proteins, including collagen [Birkedal-Hansen et al. (1988) *J. Periodontal Res.* 23, 258–264; Sundqvist et al. (1987) *J. Periodontal Res.* 22, 300–306]; fibronectin [Wikstrom and Linde (1986) *Infect. Immun.* 51, 707–711; Uitto et al. (1989) *Infect. Immun.* 57, 213–218]; immunoglobulins [Kilian, M. (1981) *Infect. Immun.* 34, 757–765; Sundqvist et al. (1985) *J. Med. Microbiol,* 19, 85–94; Sato et al. (1987) *Arch. Oral Biol.* 32, 235–238]; complement factors C3, C4, C5, and B [Sundqvist, et al. 1985) supra; Schenkein, H. A. (1988) *J. Periodontal Res.* 23, 187–192); lysozyme (Otsuka et al. (1987) *J. Periodontal Res.* 22, 491–498); iron-binding proteins (Carlsson et al. (1984) *J. Med. Microbiol,* 18, 39–46); plasma proteinase inhibitors (Carlsson et al. (1984) *Infect. Immun.* 43, 644–648; Herrmann et al. (1985) *Scand. J. Dent. Res.* 93, 153–157); fibrin and fibrinogen (Wikstrom et al. (1983) *J. Clin. Microbiol.* 17, 759–767; Lantz et al. (1986) *Infect. Immun.* 54, 654–658); and key factors of the plasma coagulation cascade system (Nilsson et al. (1985) *Infect. Immun.* 50, 467–471), are hydrolyzed by proteinases from this microorganism. Such broad proteolytic activity may play a major role in the evasion of host defense mechanisms and the destruction of gingival connective tissue associated with progressive periodontitis (Saglie et al. (1988) *J. Periodontol.* 59, 259–265).

Progressive periodontitis is characterized by acute tissue degradation promoted by collagen digestion and a vigorous inflammatory response characterized by excessive neutrophil infiltration (White and Maynard (1981) *J. Periodontal Res.* 16, 259–265). Gingival crevicular fluid accumulates in periodontitis as gingival tissue erosion progresses at the foci of the infection, and numerous plasma proteins are exposed to proteinases expressed by the bacteria at the injury site. It was speculated that neutrophils may have been recruited to the gingiva, in part, by the humoral chemotactic factor C5a. The complement components C3 and C5 are activated by complex plasma proteases with "trypsin-like" specificities called convertases (Muller-Eberhard (1988) *Ann. Rev. Biochem.* 57, 321–347). The human plasma convertases cleave the α-chains of C3 and C5 at a specific site generating biologically active factors known as anaphylatoxins (i.e. C3a and C5a). The anaphylatoxins are potent proinflammatory factors exhibiting chemotactic and/or spasmogenic activities as well as promoting increased vascular permeability. The larger products from C3 and C5 cleavage (i.e. C3b and C5b) participate in functions including complement cascade activation, opsinization, and lytic complex formation.

There are conflicting data as to the number and types of proteinases produced by *P. gingivalis*. In the past, proteolytic activities of *P. gingivalis* were classified into two groups; those enzymes which specifically degraded collagen and the general "trypsin-like" proteinases which appeared to be responsible for other proteolytic activity. Trypsin (and trypsin-like proteases) cleaves after arginine or lysine in the substrates (See, e.g. Lehninger A. L. (1982), *Principles of Biochemistry,* Worth Publishing, Inc., New York). The Arg-gingipain described herein differ in that they are specific for cleavage after only arginine, with no activity for cleavage after lysine residues.

More recently, Birkedal-Hansen et al. (Birkedal-Hansen et al. (1988) supra.) performed a systematic analysis of the effect of six classes of proteinase inhibitors on Porphyromonas collagenolytic activity which strongly suggested that all proteinases from this organism are dependent on free cysteine groups and metal ions, as indicated by inhibition by thiol-blocking reagents and metal chelators. On the other hand, Grenier et al. (Grenier et al. (1989) *Infect Immun.* 57, 95–99) identified at least eight proteolytic enzymes with molecular masses in the range of 29–110 kDa. Two of these appeared to be serine proteinases with glycyl-prolyl peptidase activity, one of which appears to be about 29 kDa (Grenier and McBride (1987) *Infect. Immun.* 55, 3131–3136).

All other enzymes were shown to be activated by cysteine and hydrolyzed the synthetic substrate Benzoyl-L-Arginyl-p-Nitroanilide (Bz-L-Arg-p-NA). Whether this represent distinct proteolytic enzymes or autocatalytic products of a single proteinase remains to be established. Although many attempts have been made to separate one of these trypsin-like proteinases (Otsuka, et al. (1987) supra.; Ono et al. (1987) *Oral Microbiol. Immunol.* 2, 77–81; Fujimura and Nakamura (1987) *Infect. Immun.* 55, 716–720; Suido et al. (1987) *J. Periodontal Res.* 22, 412–418; Tsutsui et al. (1987) *Infect. Immun.* 55, 420–427; Uitto, V. J. (1987) *J. Periodontal Res.* 22, 58–63; Sorsa et al. (1987) *J. Periodontal Res.* 22, 375–380) until now none has been purified sufficiently for rigorous biochemical and enzymological characterization.

Several communications have reported the cloning of other protease genes from *P. gingivalis*. (Arnott et al. (1990) *Arch. Oral Biol.* 35: 97S–99S; Bourgeau et al. (1992) *Infect. Immun.* 60: 3186–3192; Kato et al. (1992) *J. Bacteriol.* 174: 3889–3895; Otogoto et al. (1993) *Infect. Immun.* 61: 117–123; Park et al. (1992) *FEMS Microbiol. Lett.* 92: 273–278; Pratt et al. (1981) *Nucleic Acids Res.* 9: 4459–4474; Takahashi et al. (1991) *FEMS Microbiol. Lett.* 84: 135–138).

In this application, 50 kDa and a high molecular weight trypsin-like, thiol-activated proteinases of *P. gingivalis*, which have been purified to apparent homogeneity for the first time, is described and termed Arg-gingipain herein, and the nucleotide sequence of the gene encoding it is provided.

There is a need in the art for purified Arg-gingipain, for example, as antigen for preparing antibodies specific to this protein or for vaccines useful in protection against periodontal disease, and for studies to identify inhibitors of this enzyme.

SUMMARY OF THE INVENTION

An object of the present invention is to provide a proteinase preparation comprising a substantially pure low molecular weight Arg-gingipain, termed Arg-gingipain-1 (or gingipain-1), herein, said gingipain-1 having an apparent molecular mass of 50 kDa as estimated by sodium dodecyl sulfate polyacrylamide gel electrophoresis and an apparent molecular mass of 44 kDa as estimated by gel filtration chromatography, said gingipain-1 having amidolytic and proteolytic activity for cleavage after arginine residues and having no amidolytic and/or proteolytic activity for cleavage after lysine residues, wherein the amidolytic and/or proteolytic activity is inhibited by cysteine protease group-specific inhibitors including iodoacetamide, iodoacetic acid, N-ethylmaleimide, leupeptin, antipain,trans-epoxysuccinyl-L-leucylamido-(4-guanidine) butane, TLCK, TPCK, p-aminobenzamidine, N-chlorosuccinamide, and chelating agents including EDTA and EGTA, wherein the amidolytic and/or proteolytic activity of said gingipain-1 is not sensitive to inhibition by human cystatin C, α2-macroglobulin, α1-proteinase inhibitor, antithrombin III, α2-antiplasmin, serine protease group-specific inhibitors including diisopropylfluorophosphate, phenylmethyl sulfonylfluoride and 3,4-diisochlorocoumarin, and wherein the amidolytic and/or proteolytic activities of gingipain-1 are stabilized by $Ca^{2+}$ and wherein the amidolytic and/or proteolytic activities of said gingipain-1 are stimulated by glycine-containing peptides and glycine analogues. In a specifically exemplified gingipain-1 protein, the protein is characterized by an N-terminal amino acid sequence as given in SEQ ID NO:1 Tyr-Thr-Pro-Val-Glu-Glu-Lys-Gln-Asn-Gly-Arg-Met-Ile-Val-Ile-Val-Ala-Lys-Lys-Tyr-Glu-Gly-Asp-Ile-Lys-Asp-Phe-Val-Asp-Trp-Lys-Asn-Gln-Arg-Gly-Leu-Thr-Lys-Xaa-Val-Lys-Xaa-Ala and by a C-terminal amino acid sequence as given in SEQ ID NO:2 (Glu-Leu-Leu-Arg).

A further object of this invention is a high molecular weight form of Arg-gingipain, termed Arg-gingipain-2 herein, and prepared as described in Example 1.

As specifically exemplified, mature high molecular weight Arg-gingipain protein has a protease component having a complete deduced amino acid sequence as given in SEQ ID NO:10 from amino acid 228 through amino acid 719. An alternative protease component amino acid sequence is given in SEQ ID NO:4, amino acids 1–510. Arg-gingipain-2 further comprises a hemagglutinin component with an amino acid sequence as given in SEQ ID NO:18 from amino acid 720–1185.

It is an additional object of the invention to provide a method for the preparation of a substantially pure Arg-gingipain-1 protein. Said substantially pure Arg-gingipain-1 exhibits amidolytic and/or proteolytic activity with specificity for cleavage after arginine, but exhibits no amidolytic and/or proteolytic activity with specificity for cleavage after lysine residues. The purification method exemplified herein comprises the steps of precipitating extracellular protein from cell-free culture supernatant of Porphyromonas gingivalis with ammonium sulfate (90% w/v saturation), fractionating the precipitated proteins by gel filtration, further fractionating by anion exchange chromatography those proteins in the fractions from gel filtration with the highest specific activity for amidolytic activity as measured with Benzoyl-L-arginyl-p-nitroanilide and collecting those proteins which were not bound to the anion exchange column, and fractionating those proteins by FPLC over a cation exchange column (MonoS HR5/5, Pharmacia, Piscataway, N.J.) and finally separating gingipain-1 from lysine-specific proteolytic/amidolytic protein(s) by affinity chromatography over L-arginyl-agarose. Preferably the P. gingivalis used is strain H66, and preferably the culture is grown to early stationary phase. Arg-gingipain-1 can also be purified from cells using appropriate modifications of the foregoing procedures (cells must be disrupted, e.g., by lysis in a French pressure cell). Preferably the gel filtration step is carried out using Sephadex G-150, the anion exchange chromatography step is carried out using diethylaminoethyl (DEAE)-cellulose, the FPLC step is carried out using Mono S, and the affinity chromatography is carried out using L-arginyl-Sepharose 4B.

Another object of the present invention is to provide a nucleotide sequence encoding a low molecular weight Arg-gingipain, termed Arg-gingipain-1 (or gingipain-1), herein, said gingipain-1 having an apparent molecular mass of 50 kDa as estimated by sodium dodecyl sulfate polyacrylamide gel electrophoresis and an apparent molecular mass of 44 kDa as estimated by gel filtration chromatography, said gingipain-1 having amidolytic and proteolytic activity for cleavage after arginine residues and having no amidolytic and/or proteolytic activity for cleavage after lysine residues, wherein the amidolytic and/or proteolytic activity is inhibited by cysteine protease group-specific inhibitors including iodoacetamide, iodoacetic acid, N-ethylmaleimide, leupeptin, antipain, trans-epoxysuccinyl-L-leucylamido-(4-guanidine)butane, TLCK, TPCK, p-aminobenzamidine, N-chlorosuccinamide, and chelating agents including EDTA and EGTA, wherein the amidolytic and/or proteolytic activity of said gingipain-1 is not sensitive to inhibition by human cystatin C, α2-macroglobulin, α1-proteinase inhibitor, antithrombin III, α2-antiplasmin, serine protease group-specific inhibitors including diisopropylfluorophosphate, phenylmethyl sulfonylfluoride and 3,4-diisochlorocoumarin, and wherein the amidolytic and/or proteolytic activities of gingipain-1 are stabilized by $Ca^{2+}$ and wherein the amidolytic and/or proteolytic activities of said gingipain-1 are stimulated by glycine-containing peptides and glycine analogues. In a specifically exemplified gingipain-1 protein, the protein is characterized by an N-terminal amino acid sequence as given in SEQ ID NO:1 Tyr-Thr-Pro-Val-Glu-Glu-Lys-Gln-Asn-Gly-Arg-Met-Ile-Val-Ile-Val-Ala-Lys-Lys-Tyr-Glu-Gly-Asp-Ile-Lys-Asp-Phe-Val-Asp-Trp-Lys-Asn-Gln-Arg-Gly-Leu-Thr-Lys-Xaa-Val-Lys-Xaa-Ala) and by a C-terminal amino acid sequence as given in SEQ ID NO:2 (Glu-Leu-Leu-Arg).

A further object of this invention is a nucleotide sequence encoding a high molecular weight form of Arg-gingipain, termed Arg-gingipain-2 herein, which comprises a proteolytic component essentially as described hereinabove and at least one hemagglutinin component.

As specifically exemplified, the encoded Arg-gingipain-hemagglutinin complex is transcribed as a prepolyprotein, with the amino acid sequence as given in SEQ ID NO:10 from amino acid 1–1704. The encoded mature high molecular weight Arg-gingipain protein has a protease component having a complete deduced amino acid sequence as given in SEQ ID NO:10 from amino acid 228 through amino acid 719. An alternative protease component amino acid sequence is given in SEQ ID NO:4, amino acids 1–510. Arg-gingipain-2 further comprises at least one hemagglutinin component. The hemagglutinin components which are found associated with the 50 kDA Arg-specific proteolytic component are 44 kDa, 27 kDa and 17 kDa, and have amino acid sequences as given in SEQ ID NO:10, from 720 to 1091, from 1092 to 1429 and from 1430 to 1704, respectively.

It is an additional object of the invention to provide nucleic acid molecules for the recombinant production of an Arg-gingipain. Substantially pure recombinant Arg-gingipain-1 protein can be prepared after expression of the nucleotide sequences encoding Arg-gingipain in a heterologous host cell using the methods disclosed herein. Said substantially pure Arg-gingipain-1 exhibits amidolytic and/or proteolytic activity with specificity for cleavage after arginine, but exhibits no amidolytic and/or proteolytic activity with specificity for cleavage after lysine residues. The purification method exemplified herein comprises the steps of precipitating extracellular protein from cell-free culture supernatant of *Porphyromonas gingivalis* with ammonium sulfate (90% w/v saturation), fractionating the precipitated proteins by gel filtration, further fractionating by anion exchange chromatography those proteins in the fractions from gel filtration with the highest specific activity for amidolytic activity as measured with Benzoyl-L-arginyl-p-nitroanilide and collecting those proteins which were not bound to the anion exchange column, and fractionating those proteins by FPLC over a cation exchange column (MonoS HR5/5, Pharmacia, Piscataway, N.J.) and finally separating gingipain-1 from lysine-specific proteolytic/amidolytic protein(s) by affinity chromatography over L-arginyl-agarose. Preferably the *P. gingivalis* used is strain H66, and preferably the culture is grown to early stationary phase. Arg-gingipain-1 can also be purified from cells using appropriate modifications of the foregoing procedures (cells must be disrupted, e.g., by lysis in a French pressure cell). Preferably the gel filtration step is carried out using Sephadex G-150, the anion exchange chromatography step is carried out using diethylaminoethyl (DEAE)-cellulose, the FPLC step is carried out using Mono S, and the affinity chromatography is carried out using L-arginyl-Sepharose 4B.

It is a further object of this invention to provide non-naturally occurring nucleic acid molecules, i.e., recombinant polynucleotides (e.g., a recombinant DNA molecule) comprising a nucleotide sequence encoding an Arg-gingipain protein, preferably having an amino acid sequence as given in SEQ ID NO:10 from amino acid 228 through amino acid 719 or having an amino acid sequence as given in SEQ ID NO:4, amino acids 1 through 510. As specifically exemplified herein, the nucleotide sequence encoding a mature Arg-gingipain protease is given in SEQ ID NO:9, nucleotides 1630 through 3105, or SEQ ID NO:3 from nucleotides 1630 through 3105. The skilled artisan will understand that the amino acid sequence of the exemplified gingipain protein can be used to identify and isolate additional, nonexemplified nucleotide sequences which will encode a functional protein of the same amino acid sequence as given in SEQ ID NO:4 from amino acid 1 through amino acid 510 or an amino acid sequence of greater than 90% identity and having equivalent biological activity. The skilled artisan understands that it may be desirable to express the Arg-gingipain as a secreted protein; if so, he knows how to modify the exemplified coding sequence for the "mature" gingipain-2 by adding a nucleotide sequence encoding a signal peptide appropriate to the host in which the sequence is expressed. When it is desired that the sequence encoding an Arg-gingipain protein be expressed, then the skilled artisan will operably link transcription and translational control regulatory sequences to the coding sequences, with the choice of the regulatory sequences being determined by the host in which the coding sequence is to be expressed. With respect to a recombinant DNA molecule carrying an Arg-gingipain coding sequence, the skilled artisan will choose a vector (such as a plasmid or a viral vector) which can be introduced into and which can replicate in the host cell. The host cell can be a bacterium, preferably *Escherichia coli*, or a yeast or mammalian cell.

Also provided is a specific exemplification of a nucleotide sequence encoding an Arg-gingipain, including low molecular weight Arg-gingipain-1 protease component and the protease component of high molecular weight gingipain and its associated hemagglutinin components. These components are processed from a prepolyprotein. As specifically exemplified, the coding sequence, from nucleotide 949 to nucleotide 6063 in SEQ ID NO:9, including the stop codon, encodes a prepolyprotein having an amino acid sequence as given in SEQ ID NO:10. The prepolyprotein is encoded by a nucleotide sequence as given in SEQ ID NO:9 from nucleotide 949 to 6060. The mature protease molecule is encoded at nucleotides 1630 through 3105 in SEQ ID NO:9. The mature Arg-specific proteolytic component has an amino acid sequence as given in SEQ ID NO:10 from 228–719, and the hemagglutinin component has an amino acid sequence as in SEQ ID NO:10 from 720–1091, from 1092 to 1429 or from 1430 to 1704.

In another embodiment, recombinant polynucleotides which encode an Arg-gingipain, including, e.g., protein fusions or deletions, as well as expression systems are provided. Expression systems are defined as polynucleotides which, when transformed into an appropriate host cell, can express a proteinase. The recombinant polynucleotides possess a nucleotide sequence which is substantially similar to a natural Arg-gingipain-encoding polynucleotide or a fragment thereof.

The polynucleotides include RNA, cDNA, genomic DNA, synthetic forms, and mixed polymers, both sense and antisense strands, and may be chemically or biochemically modified or contain non-natural or derivatized nucleotide bases. DNA is preferred. Recombinant polynucleotides comprising sequences otherwise not naturally occurring are also provided by this invention, as are alterations of a wild type proteinase sequence, including but not limited to deletion, insertion, substitution of one or more nucleotides or by fusion to other polynucleotide sequences.

The present invention also provides for fusion polypeptides comprising an Arg-gingipain. Homologous polypeptides may be fusions between two or more proteinase sequences or between the sequences of a proteinase and a related protein. Likewise, heterologous fusions may be constructed which would exhibit a combination of properties or activities of the proteins from which they are derived. Fusion partners include but are not limited to immunoglobulins, ubiquitin bacterial β-galactosidase, trpE, protein A, β-lactamase, alpha amylase, alcohol dehydrogenase and yeast alpha mating factor, (Godowski et al. (1988) Science, 241, 812–816). Fusion proteins will typically be made by recombinant methods but may be chemically synthesized.

Compositions and immunogenic preparations including but not limited to vaccines, comprising recombinant Arg-gingipain derived from *P. gingivalis* and a suitable carrier therefor are provided. Such vaccines are useful, for example, in immunizing an animal, including humans, against inflammatory response and tissue damage caused by *P. gingivalis* in periodontal disease. The vaccine preparations comprise an immunogenic amount of a proteinase or an immunogenic fragment or subunit thereof. Such vaccines may comprise one or more Arg-gingipain proteinases, or an Arg-gingipain in combination with another protein or other immunogen. By "immunogenic amount" is meant an amount capable of eliciting the production of antibodies directed against one or more Arg-gingipains in an individual to which the vaccine has been administered.

BRIEF DESCRIPTION OF THE FIGURES

FIG. 3 is the model proposed for the cleavage of human C5 by Arg-gingipain-1. The two chains of C5 are represented by bars, and the hexagons labeled CHO represent the attachment sites of the N-linked oligosaccharides. The arrows labeled 1° and 2° denote the primary and secondary sites for cleavage by gingipain-1. The secondary site between residues 74 and 75 is not the only site for cleavage as degradation progresses, but is identified as a known site, based on the release of biologically active C5a.

DETAILED DESCRIPTION OF THE INVENTION

Figure 1:
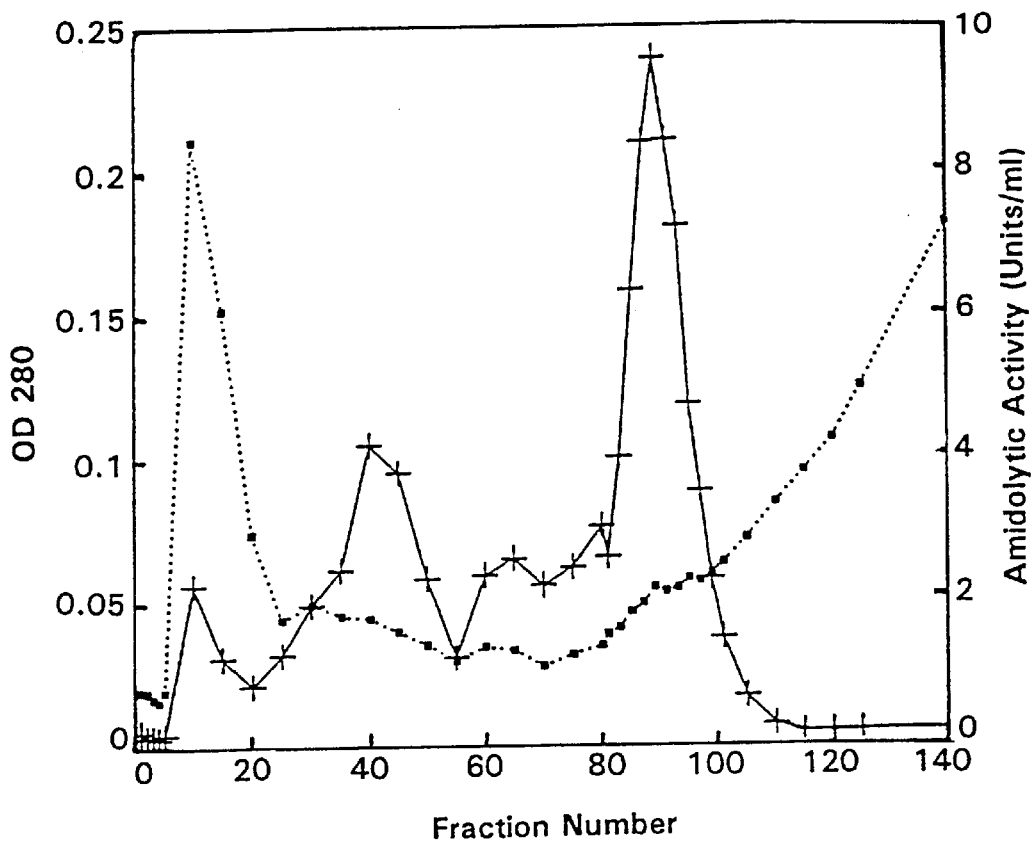
FIG. 1 illustrates the results of gel exclusion chromatography of the 90% $(NH_4)_2SO_4$- precipitated protein fraction (from *P. gingivalis* culture supernatant). Protein content was tracked by monitoring $A_{280}$ (. . . ■ . . . ) and amidolytic activity was measured using Bz-L-Arg-pNA as substrate (-+-).

Abbreviations used herein for amino acids are standard in the art: X or Xaa represents an amino acid residue that has not yet been identified but may be any amino acid residue including but not limited to phosphorylated tyrosine, threonine or serine, as well as cysteine or a glycosylated amino acid residue. The abbreviations for amino acid residues as used herein are as follows: A, Ala, alanine; V, Val, valine; L, Leu, leucine; I, Ile, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine. Other abbreviations used herein include Bz, benzoyl; Cbz, carboxybenzoyl; pNA, p-nitroanilide; MeO, methoxy; Suc, succinyl; OR, ornithyl; Pip, pipecolyl; SDS, sodium dodecyl sulfate; TLCK, tosyl-L-lysine chloromethyl ketone; TPCK, tosyl-L-phenylalanine chloromethyl ketone; S-2238, D-Phe-Pip-Arg-pNA, S-2222, Bz-Ile-Glu-(γ-OR)-Gly-pNA; S-2288, D-Ile-Pro-Arg-pNA; S-2251, D-Val-Leu-Lys-pNA; Bis-Tris, 2-[bis(2-hydroxyethyl)amino]-2-(hydroxymethyl)-propane-1,3-diol; FPLC, fast protein liquid chromatography; HPLC, high performance liquid chromatography; Tricine, N-[2-hydroxy-1,1-bis(hydroxymethyl)ethyl] glycine; EGTA, [ethylene-bis(oxyethylene-nitrile) tetraacetic acid; EDTA, ethylenediamine-tetraacetic acid; Z-L-Lys-pNa, Z-L-Lysine-p-Nitroanilide; HMW, high molecular weight.

Arg-gingipain is the term given to a *P. gingivalis* enzyme with specificity for proteolytic and/or amidolytic activity for cleavage of an amide bond, in which L-arginine contributes the carboxyl group. The Arg-gingipains described herein have identifying characteristics of cysteine dependence, inhibition response as described, $Ca^{2+}$-stabilization and glycine stimulation. Particular forms of Arg-gingipain are distinguished by their apparent molecular masses of the mature proteins (as measured without boiling before SDS-PAGE). Arg-gingipains of the present invention have no amidolytic or proteolytic activity for amide bonds in which L-lysine contributes the —COOH moiety.

Arg-gingipain-1 (or low molecular weight Arg-gingipain) is the name given herein to a protein characterized as having a molecular mass of 50 kDa as measured by SDS-PAGE and 44 kDa as measured by gel filtration over Sephadex G-150, having amidolytic and/or proteolytic activity for substrates having L-Arg in the $P_1$ position, i.e. on the N-terminal side of the peptide bond to be hydrolyzed but having no activity against corresponding lysine-containing substrates being dependent on cysteine (or other thiol groups for full activity), having sensitivity to cysteine protease group-specific inhibitors including iodoacetamide, iodoacetic acid, and N-methylmaleimide, leupeptin, antipain transepoxysuccinyl-L-leucylamido-(4-guanidino)butane, TLCK, TPCK, p-aminobenzamidine, N-chlorosuccinamide, and chelating agents including EDTA and EGTA, but being resistant to inhibition by human cystatin C, α2-macroglobulin, α1-proteinase inhibitor, antithrombin III, α2-antiplasmin, serine protease group-specific inhibitors including diisopropylfluorophosphate, phenylmethyl sulfonylfluoride and 3,4-diisochlorocoumarin, and wherein the amidolytic and/or proteolytic activities of gingipain-1 are stabilized by $Ca^{2+}$ and wherein the amidolytic and/or proteolytic activities of said gingipain-1 are stimulated by glycine-containing peptides and glycine analogues.

An exemplified Arg-gingipain described and termed High Molecular Weight Arg-gingipain herein exists in the native form in a high molecular weight form, having an apparent molecular mass of 95 kDa as determined by SDS-PAGE, without boiling of samples. When boiled, the high molecular weight form appears to dissociate into components of 50 kDa, 43 kDa, 27 kDa and 17 kDa. Arg-gingipain-2 is the name given to the 50 kDa, enzymatically active component of the high molecular weight complex.

The complete amino acid sequence of an exemplified mature Arg-gingipain is given in SEQ ID NO:10, from amino acid 228 through amino acid 719. A second possible exemplary amino acid sequence is given in SEQ ID NO:4, amino acids 1 through 510. In nature these proteins are produced by the archebacterium *Porphyromonas gingivalis;* it can be purified from cells or from culture supernatant or as a recombinant expression product using the methods provided herein. Without wishing to be bound by any theory, it is proposed that these sequences correspond to Arg-gingipain-2.

As used herein with respect to Arg-gingipain-1, a substantially pure Arg-gingipain preparation means that there is only one protein band visible after silver-staining an SDS polyacrylamide gel run with the preparation, and the only amidolytic and/or proteolytic activities are those with specificity for L-arginine in the $P_1$ position relative to the bond cleaved. A substantially pure high molecular weight Arg-gingipain preparation has only one band (95 kDa) on SDS-PAGE (sample not boiled) or four bands (50 kDa, 43 kDa, 27 kDa, 17 kDa; sample boiled). No amidolytic or proteolytic activity for substrates with lysine in the $P_1$ position is evident in a substantially pure high molecular weight or Arg-gingipain-2 preparation. Furthermore, a substantially pure preparation of Arg-gingipain has been separated from components with which it occurs in nature. Substantially pure Arg-gingipain is substantially free of naturally associated components when separated from the native contaminants which accompany them in their natural state. Thus, Arg-gingipain that is chemically synthesized or recombinantly synthesized in a cellular system different from the cell from which it naturally originates will be substantially free from its naturally associated components. Techniques for synthesis of polypeptides are described, for example, in Merrifield (1963) *J. Amer. Chem. Soc.,* 85, 2149–2156.

A chemically synthesized Arg-gingipain protein is considered an "isolated" polypeptide, as is an Arg-gingipain produced as an expression product of an isolated proteinase-encoding polynucleotide which is part of an expression vector (i.e., a "recombinant proteinase"), even if expressed in a homologous cell type.

Recombinant Arg-gingipain-1, Arg-gingipain-2 and HMW Arg-gingipain can be obtained by culturing host cells transformed with the recombinant polynucleotides comprising nucleotide sequences encoding an Arg-gingipain as described herein under conditions suitable to attain expression of the proteinase-encoding sequence.

The purification of Arg-gingipain-1 is described in Example 1 and Chen et al. (1992) *J. Biol. Chem.* 267, 18896–18901. One major problem overcome in the purification of the arginine-specific proteinase of *P. gingivalis* involved the removal of the large quantity of hemin and protohemin found to be present in the spent medium after growth of this bacterium. This was accomplished, in part, by gel filtration after ammonium sulfate precipitation of cell-free proteins (90% ammonium sulfate saturation). Chromatography over Sephadex G-150 yielded four peaks with Bz-L-Arg-pNA-hydrolyzing activity (see FIG. 1). In each of these fractions, the hydrolytic activity was dependent on cysteine and enhanced many-fold by the addition of glycylglycine or glycine amide. Peak 4 was further studied because it exhibited the highest specific activity. However, it has been determined that the antibody specific for gingipain-1 immunoprecipitates proteinase from all four Sephadex G-150 peaks.

Without wishing to be bound by any particular theory, it is postulated that the four-peak Bz-L-Arg-pNA-amidolytic profile is an anomaly resulting from the binding of gingipain-1 to membrane or nucleic acid fragments. Alternatively, those peaks containing higher molecular weight protein may contain partially processed gingipain-1 precursors. Although the purification of gingipain-1 as exemplified is from extracellular protein, it can also be purified from the bacterial cells.

Further analysis (see Example 1) of the high molecular weight fractions containing Arg-specific amidolytic and proteolytic activity revealed that Arg-gingipain-2 occurred non-covalently bound to proteins of 44 kDa, subsequently identified as a hemagglutinin, and 27 kDa and 17 kDa. The N-terminal amino acid sequence of the complexed 44 kDa protein was Ser-Gly-Gln-Ala-Glu-Ile-Val-Leu-Glu-Ala-His-Asp-Val-Xaa-Asn-Asp-Gly- (SEQ ID NO:10). This corresponds to amino acids 720–736 of SEQ ID NO: 10, with the identity of Xaa deduced to be Trp.

Arg-Gingipain-1 was further purified from the Sephadex G-150 Peak 4 protein mixture by further steps of anion exchange chromatography over DEAE-cellulose and two runs over Mono S FPLC see (Table 1).

TABLE 1

Purification of *Porphyromonas gingivalis* gingipain-1

| Step | Protein $A_{280}$ | Activity[a] units | Specific Activity units/ $A_{280}$ | Purification fold | Yield % |
|---|---|---|---|---|---|
| Culture fluid | 26,400 | 7,428 | 0.3 | 1 | 100 |
| $(NH_4)_2SO_4$ precipitate | 1,248 | 5,200 | 4.1 | 70 | 70 |
| Sephadex G-150 | 14 | 1,600 | 112 | 400 | 22 |
| DEAE-cellulose | 6 | 1,216 | 195 | 697 | 16 |
| Mono S FPLC | 2.5 | 852 | 342 | 1,223 | 11 |
| Mono S FPLC | 0.4 | 625 | 1,488 | 5,315 | 8 |

[a]Amidase activity using Bz-L-Arg-pNA; 1 unit = $A_{450}$ of 1.00/min/ml at 25° C.

As discussed in Example 1, Arg-gingipain-1 recovery was markedly reduced if an affinity chromatography step (L-Arginyl-Sepharose 4B) was used to remove trace amounts of a contaminating proteinase with specificity for cleavage after lysine residues.

Purified Arg-gingipain-1 exhibits an apparent molecular mass of about 50 KDa as determined by SDS-polyacrylamide gel electrophoresis. The size estimate obtained by gel filtration on Superose 12 (Pharmacia, Piscataway, N.J.) is 44 KDa. Amino-terminal sequence analysis through 43 residues gave a unique structure which showed no homology with any other proteins, based on a comparison in the protein NBRS data base, release 39.0. The sequence obtained is as follows:

Tyr-Thr-Pro-Val-Glu-Glu-Lys-Gln-Asn-Gly-Arg-Met-Ile-Val-Ile-Val-Ala-Lys-Lys-Tyr-Glu-Gly-Asp-Ile-Lys-Asp-Phe-Val-Asp-Trp-Lys-Asn-Gln-Arg-Gly-Leu-Thr-Lys-Xaa-Val-Lys-Xaa-Ala (SEQ ID NO:1).

The C-terminal amino acid sequence of the gingipain-1 (major form recognized in zymography SDS-PAGE, 0.1% gelatin in gel), was found to be Glu-Leu-Leu-Arg. (SEQ ID NO:2). This corresponds to the amino acids encoded at nucleotides 3094–3105 in SEQ ID NO:3 and nucleotides 3094–3105 in SEQ ID NO:9. This is consistent with the model for autoproteolytic processing of the precursor polyprotein to produce the mature 50 kDa gingipain-1 protein.

Comparison of SEQ ID NO:1 with SEQ ID NOS:4 and 10 shows differences at amino acids 37–38 of the mature Arg-gingipain proteases. Without wishing to be bound by any theory, it is proposed that SEQ ID NO:3 (or SEQ ID NO:9) comprises the coding sequence for Arg-gingipain-2, the enzymatically active component of the high molecular weight form of Arg-gingipain. This is consistent with the observation that there are at least two genes with substantial nucleic acid homology to the Arg-gingipain-specific probe.

Figure 2:
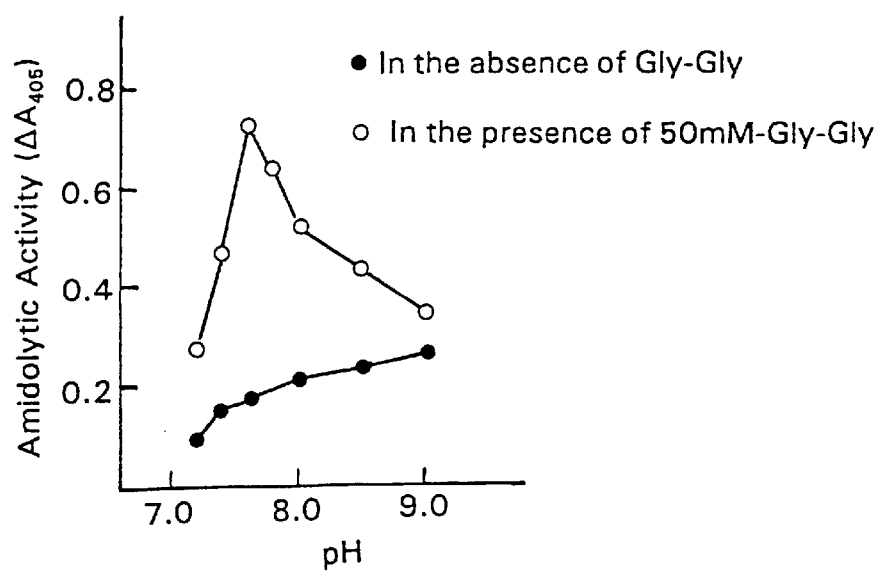
FIG. 2 illustrates the effect of assay pH on amidolytic activity of purified Arg-gingipain-1, as measured by $\Delta A_{405}$, in the presence (-○-) and absence (-●-) of 50 mM glycylglycine.

The enzymatic activity of Arg-gingipain-1 is stimulated by glycine and glycine-containing compounds. In the absence of a glycine-containing compound, the enzyme has essentially the same amidolytic activity in the pH range 7.5–9.0. However, in the presence of glycyl-glycine, e.g., substantial sharpening of the pH range for activity is observed, with the optimum being between pH 7.4 and 8.0 (FIG. 2). Preliminary kinetic data indicate that the effect of glycine and glycine analogues is to raise both $k_{cat}$ and $K_m$ equally so that the $k_{cat}/K_m$ ratio does not change. It is therefore likely that these compounds bind to the enzyme and/or substrate after an enzyme-substrate complex has already formed. The high molecular weight form is stimulated only about half as much by glycine compounds.

Arg-gingipain-1 requires cysteine for full amidolytic activity, and, although it is stimulated by other thiol-containing compounds (Table 2), the effect was less pronounced. Cysteine and cysteamine are most efficient, presumably because they perform the dual roles of reducing agents and glycine analogues.

TABLE 2

Effect of reducing agents on the amidolytic activity of gingipain-1

| Compound added | Activity −Gly-Gly | +Gly-Gly[a] |
|---|---|---|
|  | mM % |  |
| None | 100 | 320 |
| Dithiothreitol |  |  |
| 0.1 | 159 | 636 |
| 1.0 | 432 | 1,814 |
| 10.0 | 685 | 1,905 |

TABLE 2-continued

Effect of reducing agents on the amidolytic activity of gingipain-1

| Compound added | Activity −Gly-Gly | +Gly-Gly[a] |
|---|---|---|
| Mercaptoethanol |  |  |
| 0.1 | 165 | 627 |
| 1.0 | 456 | 1,860 |
| 10.0 | 685 | 2,010 |
| Glutathione |  |  |
| 0.1 | 208 | 853 |
| 1.0 | 593 | 2,550 |
| 10.0 | 770 | 3,100 |
| Cysteine |  |  |
| 0.1 | 685 | 2,740 |
| 1.0 | 1,212 | 4,985 |
| 10.0 | 1,844 | 5,290 |

[a]50 mM.

The amidolytic activity of Arg-gingipain-1 is inhibited by a number of —SH blocking group reagents, oxidants, $Ca^{2+}$ chelating agents, and $Zn^{2+}$ (Table 3). The effect of the chelating agents EDTA and EGTA was reversed completely by the addition of excess $Ca^{2+}$, whereas in the case of $Zn^{2+}$, it was necessary to add o-phenanthroline prior to $Ca^{2+}$.

Typical serine proteinase group-specific inhibitors have no effect on enzyme activity, and it is likely that inhibition by both TLCK and TPCK was caused by reaction with an essential cysteine residue in the enzyme, a known property of chloromethyl ketone derivatives. Significantly, Arg-gingipain-1 was inhibited by such cysteine proteinase inhibitors as trans-epoxysuccinyl-L-leucylamido-(4-guanidino) butane, leupeptin and antipain. Although the reactions were not stoichiometric, the inhibition was concentration-dependent. However, human cystatin C, an inhibitor of mammalian and plant cysteine proteinases, does not inhibit Arg-gingipain-1, nor did any of the trypsin-specific inhibitors from human plasma, including α2-macroglobulin, α1-proteinase inhibitor, antithrombin III, and α2-antiplasmin. Indeed, preliminary investigations actually suggested that the inhibitor in each case was being inactivated by Arg-gingipain-1.

TABLE 3

Effect of inhibitors on the amidolytic activity of Arg-gingipain-1

| Compound | Residual activity |
|---|---|
| Serine proteinase group-specific inhibitors |  |
| Diisopropylfluorophosphate (10.0 mM) | 100.0 |
| Phenylmethylsulfonyl fluoride (10.0 mM) | 100.0 |
| 3,4-Dichloroisocoumarin (10.0 mM) | 100.0 |
| Cysteine proteinase group-specific inhibitors |  |
| Iodoacetamide |  |
| 1.0 mM | 67.6 |
| 10.0 mM | 0.0 |
| Iodoacetic acid |  |
| 1.0 mM | 83.2 |
| 10.0 mM | 4.4 |

TABLE 3-continued

Effect of inhibitors on the amidolytic activity of Arg-gingipain-1

| Compound | Residual activity |
|---|---|
| N-Ethylmaleimide | |
| 1.0 mM | 79.5 |
| 10.0 mM | 3.0 |
| Chelating agents | |
| EDTA | |
| 1.0 mM | 18.6 |
| 10.0 mM | 1.8 |
| EGTA | |
| 1.0 mM | 21.3 |
| 10.0 mM | 2.4 |
| o-Phenanthroline (10.0 mM) | 95.7 |
| Others | |
| $ZnCl_2$ | |
| 1.0 mM | 90.0 |
| 10.0 mM | 0.6 |
| $MgCl_2$ (10.0 mM) | 100.0 |
| TLCK (1.0 mM) | 0.1 |
| TPCK (1.0 mM) | 0.1 |
| p-Aminobenzamidine (10.0 mM) | 13.7 |
| N-Chlorosuccinimide | |
| 1.0 mM | 20.0 |
| 10.0 mM | 1.5 |
| NaCl (0.16 M) | 100.0 |

Calcium ion stabilizes Arg-gingipain-1 without directly affecting activity. With $Ca^{2+}$ present the enzyme is stable in the pH range between 4.5 and 7.5 for several days at 4° C. However, below pH 4.0 or in the absence of $Ca^{2+}$, enzyme activity is quickly lost. At 37° C. $Ca^{2+}$ considerably increases stability, although activity is lost more rapidly than at the lower temperature. At −20° C. Arg-gingipain-1 is stable for several months. During lyophilization, however, it irreversibly loses more than 90% of its catalytic activity.

The amidolytic activity of the purified Arg-gingipain-1 on synthetic peptide substrates was limited to substrates with a $P_1$-Arg residue. Even then Arg-gingipain-1 had significantly different turnover rates on individual substrates, being most effective against S-2238 and S-2222 (Table 4). This narrow specificity was confirmed by examination of the cleavage products after incubation with the insulin B chain or mellitin; it was found that cleavage occurred specifically after only Arg residues, but not after Lys or any other amino acids unless the last affinity chromatography step over L-Arginine-Sepharose 4B was omitted.

TABLE 4

Amidolytic activity of Arg-gingipain-1

| Substrate | Activity nmol/µg/h |
|---|---|
| D-Phe-Pip-Arg-pNA (S-2238) | 756.0 |
| Bz-Ile-Glu-(γ-OR)-Gly Arg-pNA (S-2222) | 614.0 |
| D-Ile-Pro-Arg-pNA (S-2288) | 315.0 |
| Bz-Arg-pNA | 293.0 |
| D-Val-Leu-Lys-pNA (S-2251) | 0.1 |
| Suc-Ala-Ala-Ala-pNA | 0 |
| MeO-Suc-Ala-Ala-Pro-Val-pNA | 0 |

TABLE 4-continued

Amidolytic activity of Arg-gingipain-1

| Substrate | Activity nmol/µg/h |
|---|---|
| Suc-Ala-Ala-Pro-Phe-pNA | 0 |
| Gly-Pro-pNA | 0 |
| Cbz-Phe-Leu-Glu-pNA | 0 |

Preliminary studies indicated that the proteinase activity in each of the four pooled peaks, detected by assay for Bz-L-Arg-pNA hydrolysis after Sephadex G-150 chromatography, could not only digest arginine-specific synthetic substrates but also casein, collagen, the serpins α1-antichymotrypsin and antithrombin III, and the arginine-rich, neutrophil proteinase cathepsin G (but not human neutrophil elastase). In addition, enzymes in peak 1 could also degrade type I collagen and α1-proteinase inhibitor. However, no collagen degradation by purified Arg-gingipain-1 was ever detected.

Figure 3:
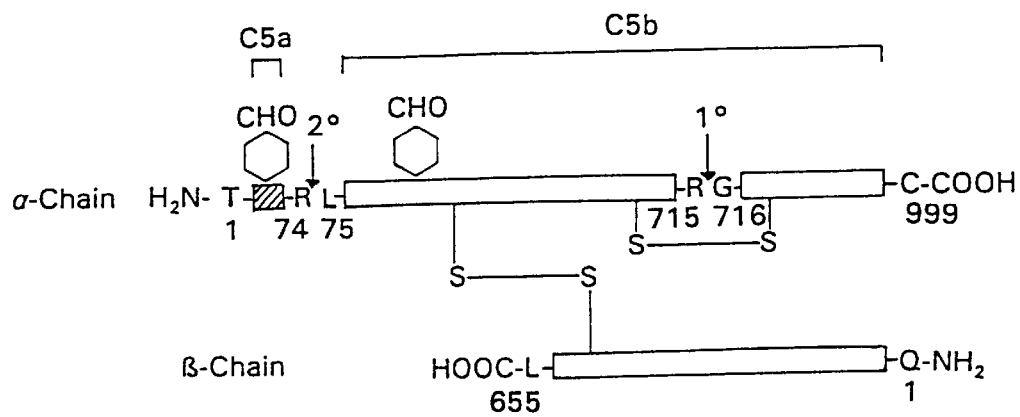
Figure 4:
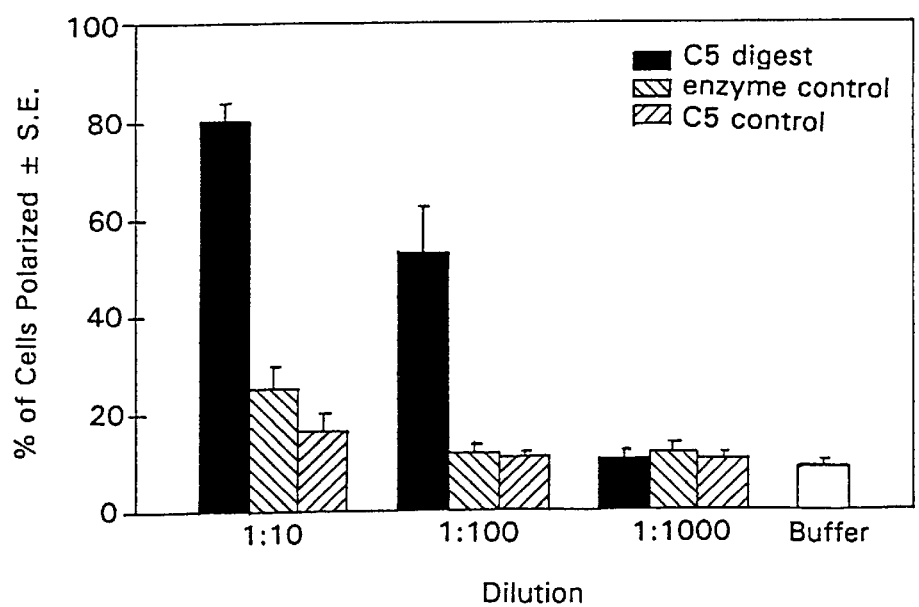
FIG. 4 illustrates the results of neutrophil polarization assays on dilutions of a human C5+Arg-gingipain-1 digestion mixture. 90 µg C5 was digested with Arg-gingipain-1 (specific activity 728 units, molar ratio 25:1) in 0.2 ml digestion buffer, pH 7.0, at 37° C. for 3 hours. Proteolysis was inhibited by adding TLCK to a final concentration of 2 mM. 50 µl EBSS containing 10 mM MOPS, pH 7.3 before dilutions were assayed for biological activity. Controls were the same except for lack of C5 (enzyme control) or Arg-gingipain (C5 control).
Figure 5:
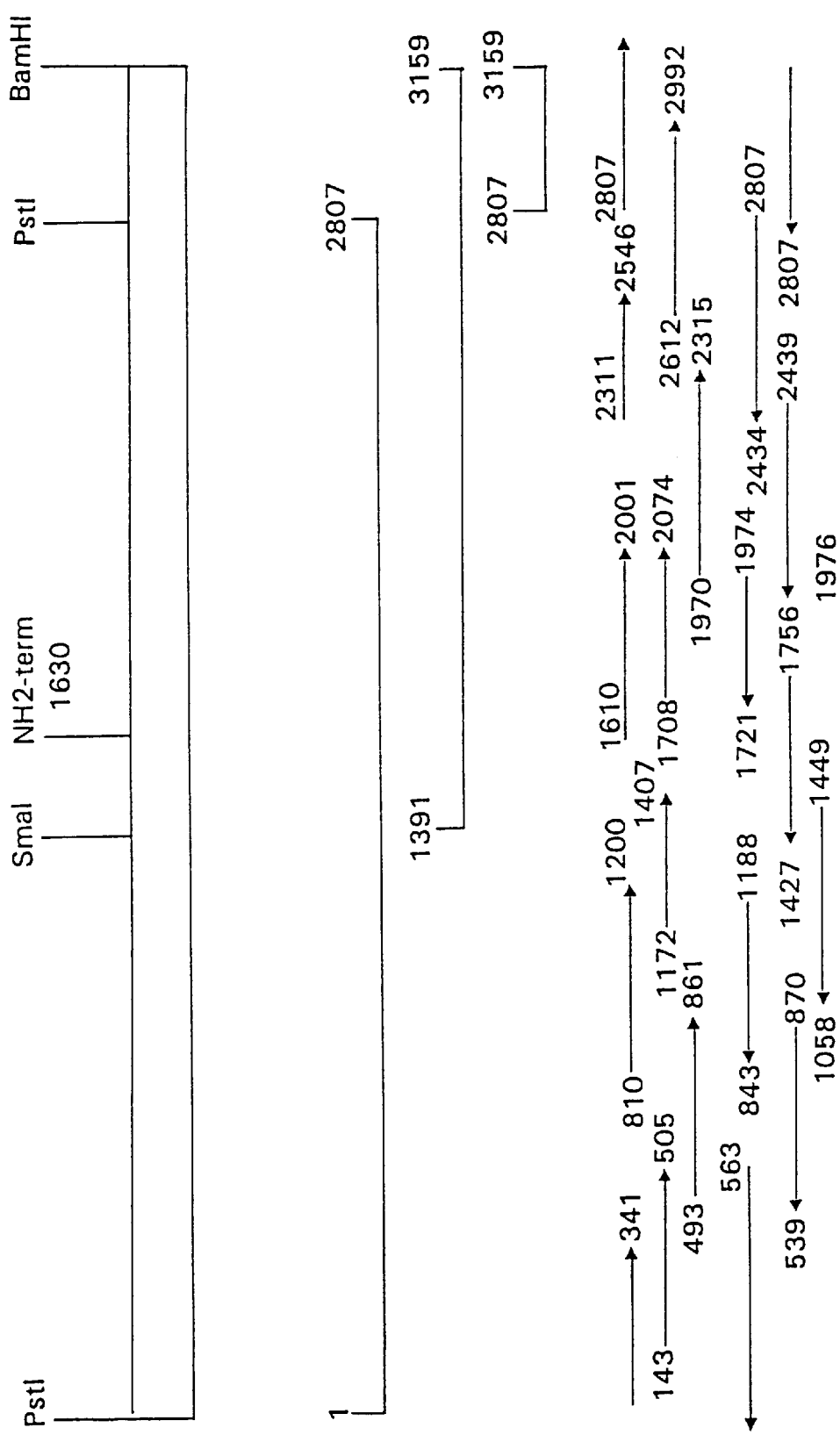
FIG. 5 illustrates the composite physical map of Arg-gingipain-2 DNA clones. The first codon of the mature gingipain is indicated. Clones PstI(1)/PstI(2807), SmaI (1391)/BamHI(3159), and PstI (2807)/BamHI(3159) are represented. The arrows indicate the extent and direction of sequencing. M13 primers and internal primers were used to sequence both strands of the putative gingipain-2 gene, initially as double strand sequencing on clone PstI(1)/PstI (2807) and then as single strand sequencing on PstI(1)/PstI (2807) clone and on PstI(2807)/BamHI(3159) clone in both directions. The junction PstI(2807) was sequenced on double stranded clone SmaI(1391)/BamHI(3159). Only restriction sites employed in cloning are indicated.
Figure 6:
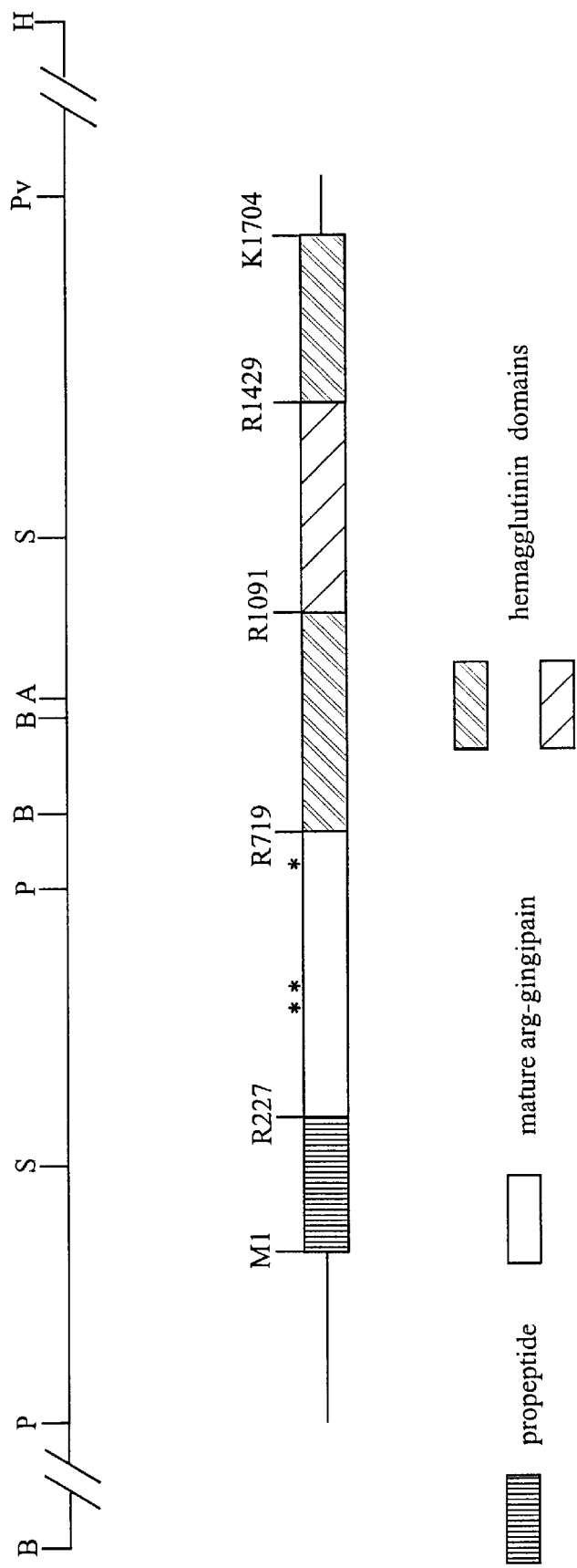
FIG. 6 illustrates the composite physical map of an Arg-gingipain locus. The first codon of the mature Arg-gingipain proteolytic component is indicated. Only major restriction sites employed in cloning are indicated: B, BamHI; P, PstI; S, SmaI; A, Asp 718; Pv, PvuII; H, HindIII. The four arginine cleavage sites (R227, R719, R1091 and R1429) are each indicated with an asterisk (*). The three residues forming the active site (C412, H438 and N669, respectively) are also shown.

Because progressive periodontitis is characterized by tissue degradation, collagen destruction and a strong inflammatory response, and because *P. gingivalis* was known to exhibit complement-hydrolyzing activity, purified Arg-gingipain-1 was tested for proteinase activity using purified human complement C3 and C5 as substrates. (See discussion herein below and Wingrove et al. (1992) *J. Biol. Chem.* 287:18902–18907. Purified human C3 was digested with gingipain-1 at a molar ratio of 25:1 in digestion buffer. Since it has been shown that the enzyme cleaves substrates such as Bz-Arg-pNA more rapidly in the presence of glycyl-glycine (Gly-Gly), time course digests both in the presence and absence of the dipeptide were carried out. The cysteine proteinase selectively cleaved the α-chain, generating what initially appeared to be the α'-chain of C3b. This result indicates that a fragment approximately the size of C3a (i.e. 9 kDa) had been released (FIG. 3). The rate of digestion with Gly-Gly present appears only slightly more rapid than without the dipeptide. The C3 α-chain was nearly all converted to the α'-chain after 1 h of digestion. Further breakdown fragments of the C3 α'-chain were observed and a decreasing intensity of the α'-band suggested that degradation continues. Visual evidence suggested that the C3 β-chain is resistant to this proteinase whether Gly-Gly is present or not.

Attempts to demonstrate C3a biological activity in the C3 digestion mixture were unsuccessful. A digest containing 300 µg of C3 was applied to a guinea pig ileal strip with no response. The sensitivity of the ileum assay would have detected approximately 1% of the C3a potentially generated in the digest. When the C3 digest was resolved by SDS-polyacrylamide gel electrophoresis (13% gel) and developed with silver stain, no material was detected in the C3a region. Thus, the C3a-like fragment released from the α-chain was extensively degraded by gingipain-1.

Human C5 was also digested by Arg-gingipain-1, with initial cleavage specific for the C5 α-chain, as in the case of C3. The α-1 (86 kDa) and the α-2 (30 kDa) fragments were the first polypeptides to be formed from cleavage of C5 by gingipain-1, and they equal the molecular weight of the intact α-chain, a fragment in the size range of C5a was observed. C5a is more resistant to the Arg-gingipain-1 than C3a, and functional C5a may accumulate without further appreciable degradation. C5a biological activity was detected after digestion of human C5 with Arg-gingipain-1. Characteristic morphologic changes in human neutrophils, known as polarization, were scored by counting deformed cells relative to normally rounded cells.

A scheme for the cleavage of C5 by Arg-gingipain-1 is shown in FIG. 3. The enzyme attacks primarily the α-chain of C5. The first peptide bond cleaved is between arginine 715 and glycine 716 of the α-chain. Subsequently, other sites are attacked including the bond between positions 74 and 75, which generates C5a.

Both human C3a and C5a were subjected to proteolysis by Arg-gingipain-1 (specific activity 1,123 units (per $A_{280}$) at 100:1 molar ratios, and degradation was evaluated after electrophoresis on cellulose acetate strips. C3a was extensively degraded after 30-min incubation, both in the presence and absence of Gly-Gly. In the presence of glycylglycine the C3a appeared partially degraded after 10 min and was nearly destroyed after 60 min. Cleavage of C3a by the Arg-gingipain-1 explains why activity could not be demonstrated in the C3 digestion mixtures; presumably the C3a fragment was released and then destroyed as the digestion continued.

C5a is more resistant to the Arg-gingipain-1 than C3a, based on the apparent rate of degradation. The majority of C5a remained intact even after 60 min of digestion, indicating that when C5 is subjected to prolonged digestion by Arg-gingipain-1, functional C5a may accumulate in the digestion mixture without further appreciable degradation.

Figure 7:
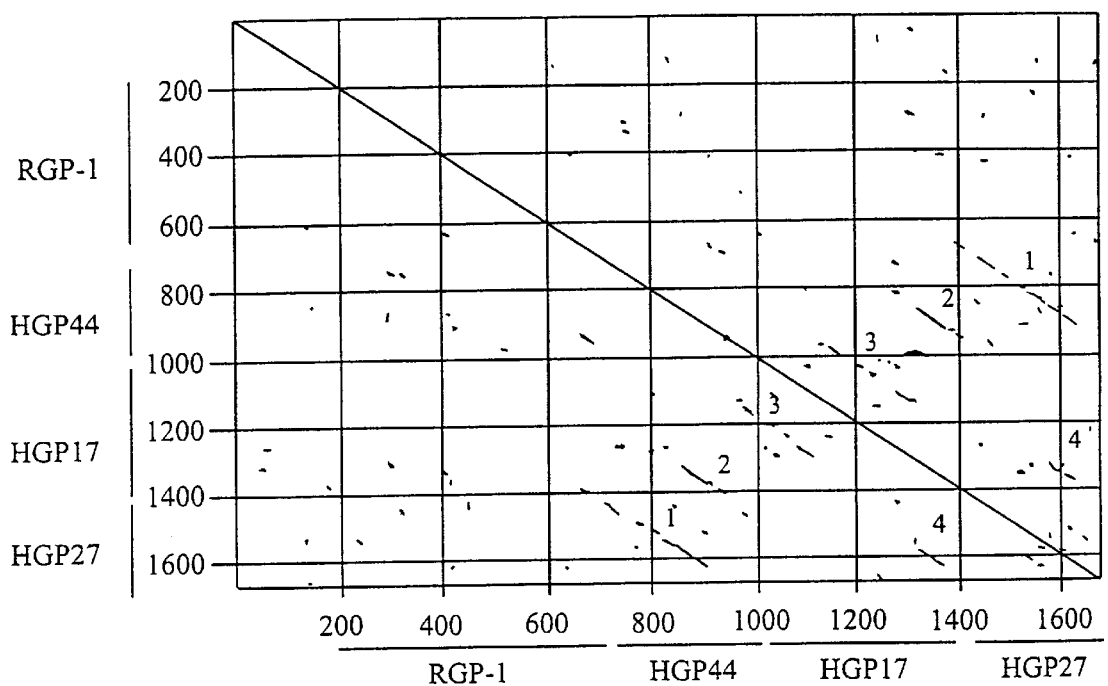
FIG. 7 is a protein matrix plot, which presents analysis of regions of similarity between hemagglutinin domains using Pustell Protein Matrix from MacVector, Release 4.0. The complete prepolyprotein sequence (SEQ ID NO:11) was used as X-axis and Y-axis. The perfect diagonal row is the line of identity, whereas structure in the pattern near that diagonal corresponds to internal repeats. The four different domains are represented (Arg-gingipain protease, 44 kDa hemagglutinin, 17 kDa hemagglutinin and 27 kDa hemagglutinin). Four regions of high homology are identified. The main homologies between hemagglutinin domains is shown in detail in Table 8.

C5a biological activity was detected as follows. Human C5 was digested at a molar ratio of 25:1 (728 U preparation) for three hours. Aliquots of the digestion mixture were diluted and incubated with human neutrophils. Characteristic morphologic changes in the cells, known as polarization, were scored by counting deformed cells relative to normally rounded cells. The neutrophil response to the digestion mixture indicated that a factor with activity like that of C5a was present (FIG. 7). Calculations of the activity expressed by the C5 digest ($ED_{50}$ for a 1:100 dilution) compared with purified C5a (described in Ember et al. (1992) *J. Immunol.* 148, 3165–3173) indicated that approximately 25% of the potential C5a activity had been generated.

A C5 digest was prepared for the neutrophil chemotaxis assay using the Arg-gingipain-1 preparation with a somewhat higher specific activity (1,123 units) than previous preparations and was used at a 100:1 molar ratio. Aliquots of the digestion mixture were diluted, and neutrophil migration was evaluated using a modified Boyden chamber assay. Estimates of the recovery of activity relative to purified C5a indicated a yield of 20%.

To characterize the bioactive products of Arg-gingipain-1 cleavage of C5, a C5 digest containing $^{125}$I-C5a added after digestion was gel size fractimated on a Bio-Gel P-60 column. An early peak of material eluted at the C5 position, and the broad second peak eluted where fragments the size of C5a would elute. Both pooled fractions of the higher molecular weight and the lower molecular weight materials were tested for neutrophil polarization and chemotactic activity. Only the pooled material of lower molecular weight, of sizes similar to C5a, elicited the polarization response and cellular migratory response.

To test for in vivo biological activity, the purified low molecular weight Arg-gingipain enzyme was injected into guinea pig skin. It induced vascular permeability enhancement at concentrations greater than $10^{-8}$ M in dose-dependent and proteolytic activity dependent manners. Vascular permeability enhancement activity was not inhibited by diphenhydramine (an antihistamine), and the activity was enhanced by SQ 20,881 (angiotensin-converting enzyme inhibitor). The vascular permeability enhancement by Arg-gingipain-1 was inhibited by soybean trypsin inhibitor (SBTI) at a concentration of $10^{-5}$ M, a concentration at which SBTI did not inhibit enzymatic activity, as measured with Bz-L-Arg-pNA and azocasein as the substrates.

Human plasma or guinea pig plasma treated with Arg-gingipain-1 ($10^{-8}$ to $10^{-6}$ M) induced vascular permeability enhancement in the guinea pig skin assay. Vascular permeability enhancement by Arg-gingipain-1 treated plasma was increased by addition of 1,10-phenanthroline (kinase inhibitor, chelating agent for Zn ions) to a final concentration of 1 mM. Vascular permeability enhancement by Arg-gingipain-1 treated plasmas was markedly reduced when plasmas deficient in Hageman factor, prekallikrein or high molecular weight kininogen were used. These results indicate that vascular permeabilizing enhancement by Arg-gingipain-1 acts via activation of Hageman factor and the subsequent release of bradykinin from high molecular weight kininogen by kallikrein.

Intradermal injection of Arg-gingipain-1 in the guinea pig also resulted in neutrophil accumulation at the site of injection, an activity which was dependent on proteolytic activity.

The foregoing results demonstrate the ability of Arg-gingipain to elicit inflammatory responses in a guinea pig animal model.

An Arg-gingipain preparation may be used in methods of identifying agents that modulate Arg-gingipain proteinase activity, whether by acting on the proteinase itself or preventing the interaction of a proteinase with a protein in gingival area, such as C3 or C5. One such method comprises the steps of incubating a proteinase with a putative therapeutic, i.e., Arg-gingipain inhibiting agent; determining the activity of the proteinase incubated with the agent; and comparing the activity obtained in step with the activity of a control sample of proteinase that has not been incubated with the agent.

SDS-PAGE analysis of the purified high molecular weight form of Arg-gingipain, without boiling, revealed a single band of apparent molecular mass of 95 kDa. This estimate was confirmed by analytical chromatography over a TSK 3000SW gel filtration column. When the enzyme preparation was boiled before SDS-PAGE, however, bands of apparent molecular masses of 50 kDa, 43 kDa, 27 kDa and 17 kDa were observed. These bands were not generated by treatments at temperatures below boiling, by reducing agents or detergents. It was concluded that the 95 kDa band was the result of strong non-covalent binding between the lower molecular weight proteins.

The 50 kDa component of the high molecular weight Arg-gingipain was characterized with respect to N-terminal amino acid sequence over 22 amino acids. The sequence was identical to the first 22 amino acids of the 50 kDa, low molecular weight Arg-gingipain-1. Characterization of the high molecular weight Arg-gingipain activity showed the same dependence on cysteine (or other thiols) and the same spectrum of response to potential inhibitors. Although the high molecular weight Arg-gingipain was stimulated by glycine compounds, the response was only about half that observed for the low molecular weight form.

Methods of treating or ameliorating the effects of Arg-gingipain-1 on affected gingival crevices of a human or animal with periodontal disease are provided. Such methods include administering to the animal (or human) an effective amount of a physiologically acceptable Arg-gingipain-1 inhibitor. Known proteinase inhibitors are generally not physiologically acceptable, but acceptable inhibitors will include agents that inhibit Arg-gingipain-1 but do not affect, or affect only marginally, the activity of endogenous proteinases. Such inhibitors can be obtained from a variety of sources including but not limited to inhibitory antibodies and small molecules. The inhibitors can be administered by a variety of methods including but not limited to topically, via aerosol to the nasal passages or lungs, subdermally and intravenously. The inhibitors can be administered as needed, particularly when applied topically. These methods of administration are known in the art and will not be described in detail herein.

Recombinant Arg-gingipain is useful in methods of identifying agents that modulate Arg-gingipain proteinase activity, whether by acting on the proteinase itself or preventing the interaction of a proteinase with a protein in gingival area, such as C3 or C5. One such method comprises the steps of incubating a proteinase with a putative therapeutic, i.e., Arg-gingipain-inhibiting, agent; determining the activity of the proteinase incubated with the agent; and comparing the activity obtained in step with the activity of a control sample of proteinase that has not been incubated with the agent.

SDS-PAGE analysis (without boiling) of the purified high molecular weight form of Arg-gingipain revealed a single band of apparent molecular mass of 95 kDa. This estimate was confirmed by analytical chromatography over a TSK 3000SW gel filtration column. When the enzyme preparation was boiled before SDS-PAGE, however, bands of apparent molecular masses of approximately 50 kDa, 44 kDa, 27 kDa and 17 kDa were observed. These bands were not generated by treatments at temperatures below boiling, by reducing agents or detergents. It was concluded that the 95 kDa band was the result of strong non-covalent binding between the lower molecular weight proteins.

The primary structure of the $NH_2$-terminus of low molecular weight Arg-gingipain determined by direct amino acid sequencing. (SEQ ID NO:1) was used to prepare a mixture of synthetic primer oligonucleotides GIN-1-32 (SEQ ID NO:6) coding for amino acids 2 to 8 of the mature protein and primer GIN-2-30 (SEQ ID NO:7) coding for amino acids 25–32 of the mature protein. These primers were used in PCR on *P. gingivalis* DNA. A single 105-base pair product (P105) resulted. This was cloned into pCR-Script™SK(−) (Stratagene) and sequenced. Sequence analysis of P105 generated 49 nucleotides from an Arg-gingipain coding sequence. On the basis of the sequence of P105, another primer (GIN-8S-48) SEQ ID NO:7 corresponding to the coding strand of the partial Arg-gingipain gene (48-mers) was synthesized in order to screen the λDASH DNA library using a $^{32}$P-labeled GIN-8S-48 probe. A partial sequence of the Arg-gingipain gene (nucleotides 1–3159, SEQ ID NO:3) was determined by screening the *P. gingivalis* DNA library using $^{32}$P-labeled hybridization GIN-8S-48 probe (SEQ ID NO:8). From a total of $2 \times 10^5$ independent plaques screened, seven positive clones were isolated and purified. After extraction and purification, the DNA was analyzed by restriction enzymes: One clone (A1) has a 3.5 kb BamHI fragment and a 3 kb PstI fragment; another clone (B1) has a 9.4 kb BamHI fragment and a 9.4 kb PstI fragment; and 5 clones have a 9.4 kb BamHI fragment and a 10 kb PstI fragment. These results are similar to those obtained by Southern analysis of *P. gingivalis* DNA and are consistent with the existence of at least two Arg-gingipain genes. The A1 clone was chosen for sequencing because the expected DNA size to encode a 50-kDa protein is approximately 1.35 kb. The 3.159 kb PstI/BamHI fragment from clone A1 was subsequently subcloned into pBluescript SK(−) as a PstI fragment and a SmaI/BamHI fragment and into M13mp18 and 19 as a PstI fragment and a PstI/BamHI fragment and sequenced. In order to clone the stop codon of gingipain-1, which was missing in the PstI/BamHI fragment, PstI/HindIII double digested *P. gingivalis* DNA clones were hybridized with $^{32}$P-labeled GIN-14-20 (SEQ ID NO:8) (nucleotides 2911–2930 of SEQ ID NO:3) localized at the 3' end of this clone. A PstI/HindIII fragment of approximately 4.3 kb was identified and cloned into pbluescript SK(−). Smaller fragment (PstI/Asp713 and BamHI/HindIII) was also subcloned into M13mp18 and 19.

SEQ ID NO:3 is the DNA sequence of the 3159 bp PstI/BamHI fragment (see Table 5).

TABLE 5

Nucleotide sequence and deduced amino acid sequence of Gingipain:

Sequence: 1 to 3159

```
            10          20          30          40
            *           *           *           *
   CTG CAG AGG GCT GCT AAA GAC CGC CTC GGG ATC GAG GCC TTT GAG ACG
   GAC GTC TCC CGA CGA TTT CTG GCG GAG CCC TAG CTC CGG AAA CTC TGC 50          60          70          80          90
    *           *           *           *           *
   GGC ACA AGC CGC CGC AGC CTC CTC TTC GAA GGT GTC TCG AAC GTC CAC
   CCG TGT TCG GCG GCG TCG TCG GAG GAG AAG CTT CAG AGC TTG CAG GTG 100         110         120         130         140
    *           *           *           *           *
   ATC GGT GAA TCC GTA GCA GTG CTC ATT GCC ATT GAG CAG CAC CGA GGT
   TAG CCA CTT AGG CAT CGT CAC GAG TAA CGG TAA CTC GTC GTG GCT CCA 150         160         170         180         190
    *           *           *           *           *
   GTG GCG CAT CAG ATA TAT TTT CAT CAG TGG ATT ATT AGG GTA TCG GTC
   CAC CGC GTA GTC TAT ATA AAA GTA GTC ACC TAA TAA TCC CAT AGC CAG 200         210         220         230         240
    *           *           *           *           *
   AGA AAA AGC CTT CCG AAT CCG ACA AAG ATA GTA GAA AGA GAG TGC ATC
   TCT TTT TCG GAA GGC TTA GGC TGT TTC TAT CAT CTT TCT CTC ACG TAG 250         260         270         280
```

TABLE 5-continued

Nucleotide sequence and deduced amino acid sequence of Gingipain:

```
              *              *              *              *
    TGA AAA CAG ATC ATT CGA GGA TTA TCG ATC AAC TGA AAA GGC AGG AGT
    ACT TTT GTC TAG TAA GCT CCT AAT AGC TAG TTG ACT TTT CCG TCC TCA 290           300           310           320           330
     *             *             *             *             *
    TGT TTT GCG TTT TGG TTC GGA AAA TTA CCT GAT CAG CAT TCG TAA AAA
    ACA AAA CGC AAA ACC AAG CCT TTT AAT GGA CTA GTC GTA AGC ATT TTT 340           350           360           370           380
          *             *             *             *             *
    CGT GGC GCG AGA ATT TTT TCG TTT TGG CGC GAG AAT TAA AAA TTT TTG
    GCA CCG CGC TCT TAA AAA AGC AAA ACC GCG CTC TTA ATT TTT AAA AAC 390           400           410           420           430
          *             *             *             *             *
    GAA CCA CAG CGA AAA AAA TCT CGC GCC GTT TTC TCA GGA TTT ACA GAC
    CTT GGT GTC GCT TTT TTT AGA GCG CGG CAA AAG AGT CCT AAA TGT CTG 440           450           460           470           480
               *             *             *             *             *
    CAC AAT CCG AGC ATT TTC GGT TCG TAA TTC ATC GAA GAG ACA GGT TTT
    GTG TTA GGC TCG TAA AAG CCA AGC ATT AAG TAG CTT CTC TGT CCA AAA 490           500           510           520
               *             *             *             *
    ACC GCA TTG AAA TCA GAG AGA GAA TAT CCG TAG TCC AAC GGT TCA TCC
    TGG CGT AAC TTT AGT CTC TCT CTT ATA GGC ATC AGG TTG CCA AGT AGG 530           540           550           560           570
     *             *             *             *             *
    TTA TAT CAG AGG TTA AAA GAT ATG GTA CGC TCA TCG AGG AGC TGA TTG
    AAT ATA GTC TCC AAT TTT CTA TAC CAT GCG AGT AGC TCC TCG ACT AAC 580           590           600           610           620
          *             *             *             *             *
    GCT TAG TAG GTG AGA CTT TCT TAA GAG ACT ATC GGC ACC TAC AGG AAG
    CGA ATC ATC CAC TCT GAA AGA ATT CTC TGA TAG CCG TGG ATG TCC TTC 630           640           650           660           670
               *             *             *             *             *
    TTC ATG GCA CAC AAG GCA AAG GAG GCA ATC TTC GCA GAC CGG ACT CAT
    AAG TAC CGT GTG TTC CGT TTC CTC CGT TAG AAG CGT CTG GCC TGA GTA 680           690           700           710           720
               *             *             *             *             *
    ATC AAA AGG ATG AAA CGA CTT TTC CAT ACG ACA ACC AAA TAG CCG TCT
    TAG TTT TCC TAC TTT GCT GAA AAG GTA TGC TGT TGG TTT ATC GGC AGA 730           740           750           760
               *             *             *             *
    ACG GTA GAC GAA TGC AAA CCC AAT ATG AGG CCA TCA ATC AAT CCG AAT
    TGC CAT CTG CTT ACG TTT GGG TTA TAC TCC GGT AGT TAG TTA GGC TTA 770           780           790           800           810
     *             *             *             *             *
    GAC AGC TTT TGG GCA ATA TAT TAT GCA TAT TTT GAT TCG CGT TTA AAG
    CTG TCG AAA ACC CGT TAT ATA ATA CGT ATA AAA CTA AGC GCA AAT TTC 820           830           840           850           860
     *             *             *             *             *
    GAA AAG TGC ATA TAT TTG CGA TTG TGG TAT TTC TTT CGG TTT CTA TGT
    CTT TTC ACG TAT ATA AAC GCT AAC ACC ATA AAG AAA GCC AAA GAT ACA 870           880           890           900           910
          *             *             *             *             *
    GAA TTT TGT CTC CCA AGA AGA CTT TAT AAT GCA TAA ATA CAG AAG GGG
    CTT AAA ACA GAG GGT TCT TCT GAA ATA TTA CGT ATT TAT GTC TTC CCC 920           930           940           950           960
               *             *             *             *             *
    TAC TAC ACA GTA AAA TCA TAT TCT AAT TTC ATC AAA ATG AAA AAC TTG
    ATG ATG TGT CAT TTT AGT ATA AGA TTA AAG TAG TTT TAC TTT TTG AAC
                                                    M   K   N   L>

970           980           990           1000
               *             *             *             *
```

TABLE 5-continued

Nucleotide sequence and deduced amino acid sequence of Gingipain:

```
AAC AAG TTT GTT TCG ATT GCT CTT TGC TCT TCC TTA TTA GGA GGA ATG
TTG TTC AAA CAA AGC TAA CGA GAA ACG AGA AGG AAT AAT CCT CCT TAC
 N   K   F   V   S   I   A   L   C   S   S   L   L   G   G   M>

1010        1020        1030        1040        1050
  *           *           *           *           *
GCA TTT GCG CAG CAG ACA GAG TTG GGA CGC AAT CCG AAT GTC AGA TTG
CGT AAA CGC GTC GTC TGT CTC AAC CCT GCG TTA GGC TTA CAG TCT AAC
 A   F   A   Q   Q   T   E   L   G   R   N   P   N   V   R   L>

1060        1070        1080        1090        1100
      *           *           *           *           *
CTC GAA TCC ACT CAG CAA TCG GTG ACA AAG GTT CAG TTC CGT ATG GAC
GAG CTT AGG TGA GTC GTT AGC CAC TGT TTC CAA GTC AAG GCA TAC CTG
 L   E   S   T   Q   Q   S   V   T   K   V   Q   F   R   M   D>

1110        1120        1130        1140        1150
        *           *           *           *           *
AAC CTC AAG TTC ACC GAA GTT CAA ACC CCT AAG GGA ATC GGA CAA GTG
TTG GAG TTC AAG TGG CTT CAA GTT TGG GGA TTC CCT TAG CCT GTT CAC
 N   L   K   F   T   E   V   Q   T   P   K   G   I   G   Q   V>

1160        1170        1180        1190        1200
            *           *           *           *           *
CCG ACC TAT ACA GAA GGG GTT AAT CTT TCC GAA AAA GGG ATG CCT ACG
GGC TGG ATA TGT CTT CCC CAA TTA GAA AGG CTT TTT CCC TAC GGA TGC
 P   T   Y   T   E   G   V   N   L   S   E   K   G   M   P   T>

1210        1220        1230        1240
              *           *           *           *
CTT CCC ATT CTA TCA CGC TCT TTG GCG GTT TCA GAC ACT CGT GAG ATG
GAA GGG TAA GAT AGT GCG AGA AAC CGC CAA AGT CTG TGA GCA CTC TAC
 L   P   I   L   S   R   S   L   A   V   S   D   T   R   E   M>

1250        1260        1270        1280        1290
  *           *           *           *           *
AAG GTA GAG GTT GTT TCC TCA AAG TTC ATC GAA AAG AAA AAT GTC CTG
TTC CAT CTC CAA CAA AGG AGT TTC AAG TAG CTT TTC TTT TTA CAG GAC
 K   V   E   V   V   S   S   K   F   I   E   K   K   N   V   L>

1300        1310        1320        1330        1340
      *           *           *           *           *
ATT GCA CCC TCC AAG GGC ATG ATT ATG CGT AAC GAA GAT CCG AAA AAC
TAA CGT GGG AGG TTC CCG TAC TAA TAC GCA TTG CTT CTA GGC TTT TTG
 I   A   P   S   K   G   M   I   M   R   N   E   D   P   K   K>

1350        1360        1370        1380        1390
        *           *           *           *           *
ATC CCT TAC GTT TAT GGA AAG AGC TAC TCG CAA AAC AAA TTC TTC CCG
TAG GGA ATG CAA ATA CCT TTC TCG ATG AGC GTT TTG TTT AAG AAG GGC
 I   P   Y   V   Y   G   K   S   Y   S   Q   N   K   F   F   P>

1400        1410        1420        1430        1440
            *           *           *           *           *
GGA GAG ATC GCC ACG CTT GAT GAT CCT TTT ATC CTT CGT GAT GTG CGT
CCT CTC TAG CGG TGC GAA CTA CTA GGA AAA TAG GAA GCA CTA CAC GCA
 G   E   I   A   T   L   D   D   P   F   I   L   R   D   V   R>

1450        1460        1470        1480
              *           *           *           *
GGA GAG GTT GTA AAC TTT GCG CCT TTG CAG TAT AAC CCT GTG ACA AAG
CCT CTC CAA CAT TTG AAA CGC GGA AAC GTC ATA TTG GGA CAC TGT TTC
 G   Q   V   V   N   F   A   P   L   Q   Y   N   P   V   T   K>

1490        1500        1510        1520        1530
  *           *           *           *           *
ACG TTG CGC ATC TAT ACG GAA ATC ACT GTG GCA GTG AGC GAA ACT TCG
TGC AAC GCG TAG ATA TGC CTT TAG TGA CAC CGT CAC TCG CTT TGA AGC
 T   L   R   I   Y   T   E   I   T   V   A   V   S   E   T   S>

1540        1550        1560        1570        1580
  *           *           *           *           *
GAA CAA GGC AAA AAT ATT CTG AAC AAG AAA GGT ACA TTT GCC GGC TTT
CTT GTT CCG TTT TTA TAA GAC TTG TTC TTT CCA TGT AAA CGG CCG AAA
 E   Q   G   K   N   I   L   N   K   K   G   T   F   A   G   F>

1590        1600        1610        1620        1630
```

TABLE 5-continued

Nucleotide sequence and deduced amino acid sequence of Gingipain:

```
         *              *              *              *              *
GAA GAC ACA TAC AAG CGC ATG TTC ATG AAC TAC GAG CCG GGG CGT TAC
CTT CTG TGT ATG TTC GCG TAC AAG TAC TTG ATG CTC GGC CCC GCA ATG
 E   D   T   Y   K   R   M   F   K   N   Y   E   P   G   R   Y>

1640           1650           1660           1670           1680
         *              *              *              *              *
ACA CCG GTA GAG GAA AAA CAA AAT GGT CGT ATG ATC GTC ATC GTA GCC
TGT GGC CAT CTC CTT TTT GTT TTA CCA GCA TAC TAG CAG TAG CAT CGG
 T   P   V   E   E   K   Q   N   G   R   M   I   V   I   V   A>

1690           1700           1710           1720
              *              *              *              *
AAA AAG TAT GAG GGA GAT ATT AAA GCT TTC GTT GAT TGG AAA AAC CAA
TTT TTC ATA CTC CCT CTA TAA TTT CGA AAG CAA CTA ACC TTT TTG GTT
 K   K   Y   E   G   D   I   K   A   F   V   D   W   K   N   Q>

1730           1740           1750           1760           1770
 *              *              *              *              *
CGC GGT CTC CGT ACC GAG GTG AAA GTG GCA GAA GAT ATT GCT TCT CCC
GCG CCA GAG GCA TGG CTC CAC TTT CAC CGT CTT CTA TAA CGA AGA GGG
 R   G   L   R   T   E   V   K   V   A   E   D   I   A   S   P>

1780           1790           1800           1810           1820
     *              *              *              *              *
GTT ACA GCT AAT GCT ATT CAG CAG TTC GTT AAG CAA GAA TAC GAG AAA
CAA TGT CGA TTA CGA TAA GTC GTC AAG CAA TTC GTT CTT ATG CTC TTT
 V   T   A   N   A   I   Q   Q   F   V   K   Q   E   Y   E   K>

1830           1840           1850           1860           1870
         *              *              *              *              *
GAA GGT AAT GAT TTG ACC TAT GTT CTT TTG GTT GGC GAT CAC AAA GAT
CTT CCA TTA CTA AAC TGG ATA CAA GAA AAC CAA CCG CTA GTG TTT CTA
 E   G   N   D   L   T   Y   V   L   L   V   G   D   H   K   D>

1880           1890           1900           1910           1920
              *              *              *              *              *
ATT CCT GCC AAA ATT ACT CCG GGG ATC AAA TCC GAC CAG GTA TAT GGA
TAA GGA CGG TTT TAA TGA GGC CCC TAG TTT AGG CTG GTC CAT ATA CCT
 I   P   A   K   I   T   P   G   I   K   S   D   Q   V   Y   G>

1930           1940           1950           1960
              *              *              *              *
CAA ATA GTA GGT AAT GAC CAC TAC AAC GAA GTC TTC ATC GGT CGT TTC
GTT TAT CAT CCA TTA CTG GTG ATG TTG CTT CAG AAG TAG CCA GCA AAG
 Q   I   V   G   N   D   H   Y   N   E   V   F   I   G   R   F>

1970           1980           1990           2000           2010
 *              *              *              *              *
TCA TGT GAG AGC AAA GAG GAT CTG AAG ACA CAA ATC GAT CGG ACT ATT
AGT ACA CTC TCG TTT CTC CTA GAC TTC TGT GTT TAG CTA GCC TGA TAA
 S   C   E   S   K   E   D   L   K   T   Q   I   D   R   T   I>

2020           2030           2040           2050           2060
     *              *              *              *              *
CAC TAT GAG CGC AAT ATA ACC ACG GAA GAC AAA TGG CTC GGT CAG GCT
GTG ATA CTC GCG TTA TAT TGG TGC CTT CTG TTT ACC GAG CCA GTC CGA
 H   Y   E   R   N   I   T   T   E   D   K   W   L   G   Q   A>

2070           2080           2090           2100           2110
         *              *              *              *              *
CTT TGT ATT GCT TCG GCT GAA GGA GGC CGA TCC GCA GAC AAT GGT GAA
GAA ACA TAA CGA AGC CGA CTT CCT CCG GCT AGG CGT CTG TTA CCA CTT
 L   C   I   A   S   A   E   G   G   P   S   A   D   N   G   E>

2120           2130           2140           2150           2160
              *              *              *              *              *
AGT GAT ATC GAG CAT GAG AAT GTA ATC GCC AAT CTG CTT ACC CAG TAT
TCA CTA TAG CTC GTA CTC TTA CAT TAG CGG TTA GAC GAA TGG GTC ATA
 S   D   I   Q   H   E   N   V   I   A   N   L   L   T   Q   Y>

2170           2180           2190           2200
              *              *              *              *
GGC TAT ACC AAG ATT ATC AAA TGT TAT GAT CCG GGA GTA ACT CCT AAA
CCG ATA TGG TTC TAA TAG TTT ACA ATA CTA GGC CCT GAT TGA GGA TTT
 G   Y   T   K   I   I   K   C   Y   D   P   G   V   T   P   K>
```

TABLE 5-continued

Nucleotide sequence and deduced amino acid sequence of Gingipain:

```
2210          2220          2230          2240          2250
  *             *             *             *             *
AAC ATT ATT GAT GGT TTC AAC GGA GGA ATC TCG TTG GTC AAC TAT ACG
TTG TAA TAA CTA CGA AAG TTG CCT CCT TAG AGC AAC CAG TTG ATA TGC
 N   I   I   D   A   F   N   G   G   I   S   L   V   N   Y   T>

2260          2270          2280          2290          2300
      *             *             *             *             *
GGC CAC GGT AGC GAA ACA GCT TGG GGT ACG TCT CAC TTC GGC ACC ACT
CCG GTG CCA TCG CTT TGT CGA ACC CCA TGC AGA GTG AAG CCG TGG TGA
 G   H   G   S   E   T   A   W   G   T   S   H   F   G   T   T>

2310          2320          2330          2340          2350
         *             *             *             *             *
CAT GTG AAG CAG CTT ACC AAC AGC AAC CAG CTA CCG TTT ATT TTC GAC
GTA CAC TTC GTC GAA TGG TTG TCG TTG GTC GAT GGC AAA TAA AAG CTG
 H   V   K   Q   L   T   N   S   N   Q   L   P   F   I   F   D>

2360          2370          2380          2390          2400
            *             *             *             *             *
GTA GCT TGT GTG AAT GGC GAT TTC CTA TTC AGC ATG CCT TGC TTC GCA
CAT CGA ACA CAC TTA CCG CTA AAG GAT AAG TCG TAC GGA ACG AAG CGT
 V   A   C   V   N   G   D   F   L   F   S   M   P   C   F   A>

2410          2420          2430          2440
               *             *             *             *
GAA GCC CTG ATG CGT GCA CAA AAA GAT GGT AAG CCG ACA GGT ACT GTT
CTT CGG GAC TAC GCA CGT GTT TTT CTA CCA TTC GGC TGT CCA TGA CAA
 E   A   L   M   R   A   Q   K   D   G   K   P   T   G   T   V>

2450          2460          2470          2480          2490
  *             *             *             *             *
GCT ATC ATA GCG TCT ACG ATC AAC CAG TCT TGG GCT TCT CCT ATG CGC
CGA TAG TAT CGC AGA TGC TAG TTG GTC AGA ACC CGA AGA GGA TAC GCG
 A   I   I   A   S   T   I   N   Q   S   W   A   S   P   M   R>

2500          2510          2520          2530          2540
      *             *             *             *             *
GGG CAG GAT GAG ATG AAC GAA ATT CTG TGC GAA AAA CAC CCG AAC AAC
CCC GTC CTA CTC TAC TTG CTT TAA GAC ACG CTT TTT GTG GGC TTG TTG
 G   Q   D   E   M   N   E   I   L   C   E   K   H   P   N   N>

2550          2560          2570          2580          2590
         *             *             *             *             *
ATC AAG CGT ACT TTC GGT GGT GTC ACC ATG AAC GGT ATG TTT GCT ATG
TAG TTC GCA TGA AAG CCA CCA CAG TGG TAC TTG CCA TAC AAA CGA TAC
 I   K   R   T   F   G   G   V   T   M   N   G   M   F   A   M>

2600          2610          2620          2630          2640
            *             *             *             *             *
GTG GAA AAG TAT AAA AAG GAT GGT GAG AAG ATG CTC GAC ACA TGG ACT
CAC CTT TTC ATA TTT TTC CTA CCA CTC TTC TAC GAG CTG TGT ACC TGA
 V   E   K   Y   K   K   D   G   E   K   M   L   D   T   W   T>

2650          2660          2670          2680
               *             *             *             *
GTT TTC GGC GAC CCC TCG CTG CTC GTT CGT ACA CTT GTC CCG ACC AAA
CAA AAG CCG CTG GGG AGC GAC GAG CAA GCA TGT GAA CAG GGC TGG TTT
 V   F   G   D   P   S   L   L   V   R   T   L   V   P   T   K>

2690          2700          2710          2720          2730
  *             *             *             *             *
ATG CAG GTT ACG GCT CCG GCT CAG ATT AAT TTG ACG GAT GCT TCA GTC
TAC GTC CAA TGC CGA GGC CGA GTC TAA TTA AAC TGC CTA CGA AGT CAG
 M   Q   V   T   A   P   A   Q   I   N   L   T   D   A   S   V>

2740          2750          2760          2770          2780
         *             *             *             *             *
AAC GTA TCT TGC GAT TAT AAT GGT GCT ATT GCT ACC ATT TCA GCC AAT
TTG CAT AGA ACG CTA ATA TTA CCA CGA TAA CGA TGG TAA AGT CGG TTA
 N   V   S   C   D   Y   N   G   A   I   A   T   I   S   A   N>

2790          2800          2810          2820          2830
            *             *             *             *             *
GGA AAG ATG TTC GGT TCT GCA GTT GTC GAA AAT GGA ACA GCT ACA ATC
CCT TTC TAC AAG CCA AGA CGT CAA CAG CTT TTA CCT TGT CGA TGT TAG
 G   K   M   F   G   S   A   V   V   E   N   G   T   A   T   I>
```

TABLE 5-continued

Nucleotide sequence and deduced amino acid sequence of Gingipain:

```
            2840          2850          2860          2870          2880
              *             *             *             *             *
    AAT CTG ACA GGT CTG ACA AAT GAA AGC ACG CTT ACC CTT ACA GTA GTT
    TTA GAC TGT CCA GAC TGT TTA CTT TCG TGC GAA TGG GAA TGT CAT CAA
     N   L   T   G   L   T   N   E   S   T   L   T   L   T   V   V>

2890          2900          2910          2920
                *             *             *             *
    GGT TAC AAC AAA GAG ACG GTT ATT AAG ACC ATC AAC ACT AAT GGT GAG
    CCA ATG TTG TTT CTC TGC CAA TAA TTC TGG TAG TTG TGA TTA CCA CTC
     G   Y   N   K   E   T   V   I   K   T   I   N   T   N   G   E>

2930          2940          2950          2960          2970
    *             *             *             *             *
    CCT AAC CCC TAC CAG CCC GTT TCC AAC TTG ACA GCT ACA ACG CAG GGT
    GGA TTG GGG ATG GTC GGG CAA AGG TTG AAC TGT CGA TGT TGC GTC CCA
     P   N   P   Y   Q   P   V   S   N   L   T   A   T   T   Q   G>

2980          2990          3000          3010          3020
      *             *             *             *             *
    CAG AAA GTA ACG CTC AAG TGG GAT GCA CCG AGC ACG AAA ACC AAT GCA
    GTC TTT CAT TGC GAG TTC ACC CTA CGT GGC TCG TGC TTT TGG TTA CGT
     Q   K   V   T   L   K   W   D   A   P   S   T   K   T   N   A>

3030          3040          3050          3060          3070
          *             *             *             *             *
    ACC ACT AAT ACC GCT CGC AGC GTG GAT GGC ATA CGA GAA TTG GTT CTT
    TGG TGA TTA TGG CGA GCG TCG CAC CTA CCG TAT GCT CTT AAC CAA GAA
     T   T   N   T   A   R   S   V   D   G   I   R   E   L   V   L>

3080          3090          3100          3110          3120
              *             *             *             *             *
    CTG TCA GTC AGC GAT GCC CCC GAA CTT CTT CGC AGC GGT CAG GCC GAG
    GAC AGT CAG TCG CTA CGG GGG CTT GAA GAA GCG TCG CCA GTC CGG CTC
     L   S   V   S   D   A   P   E   L   L   R   S   G   Q   A   E>

3130          3140          3150
                *             *             *
    ATT GTT CTT GAA GCT CAC GAT GTT TGG AAT GAT GGA TCC
    TAA CAA GAA CTT CGA GTG CTA CAA ACC TTA CTA CCT AGG
     I   V   L   E   A   H   D   V   W   N   D   G   S>
```

Exemplified nucleotide sequences encoding a mature Arg-gingipain, termed an Arg-gingipain-2 herein, extends from 1630–3105 in SEQ ID NO:3 and in SEQ ID NO:9. The first ATG appears at nucleotide 949 and is followed by a long open reading frame (ORF), of 5111 bp in Table 6 (SEQ ID NO:9). This ORF was the largest one observed. However, the first ATG is following by 8 others in frame (at nucleotides 1006, 1099, 1192, 1246, 1315, 1321, 1603, and 1609). The most likely candidate to initiate translation is currently unknown. Which of these initiation codons are used in translation of the Arg-gingipain-2 precursor can be determined by expression of the polyprotein in bacteria and subsequent amino-terminal sequence analysis of proprotein intermediates. The sequence derived from 5' noncoding sequences is composed of 948 bp. The primary structure of the mature Arg-gingipain molecule can be inferred from the empirical amino-terminal and carboxy-terminal sequences and molecular mass. Thus, mature Arg-gingipain-2 has an amino terminus starting at nucleotide residue 1630 in SEQ ID NO:3 and at amino acid 1 in SEQ ID NO:4. As expected for an arginine-specific protease, the mature protein is cleaved after an arginine residue. The 50 kDa and the 44 kDa bands from Bz-L-Arg-pNa activity peaks have an identical sequence to that deduced amino acid sequence of gingipain, encoded respectively at nucleotides 1630–1695 and at nucleotides 3106–3156. From these data, the carboxyl terminus is most likely derived from autoproteolytic processing after the arginine residue encoded at 3103–3105 where the amino terminus encoding sequence of a hemagglutinin component starts (nucleotide 3106). The deduced 492 amino acids of gingipain-2 give rise to a protease molecule with a calculated molecular weight of 54 kDa which correlates well with the molecular mass of 50 kDa determined by SDS-PAGE analysis. Tables 5 and 6 (see also SEQ ID NO:9 and 10) presents the coding sequence and deduced amino acid sequence of gingipain-2. The first nucleotide presented in the sequence belongs to the PstI cloning site and is referred as nucleotide 1. Bold face letters indicate the potential sites of initiation ATG and the first codon of the mature gingipain-2. The amino terminal sequence of gingipain-2 and the amino terminal sequence of 44 kDa bands from Bz-L-Arg-pNa activity peaks are underlined.

Table 6 (corresponding to SEQ ID NOS:9–10) presents the nucleotide sequence encoding the complete prepolyprotein sequence, including both the protease component and the hemagglutinin component(s) of HMW Arg-gingipain. The coding sequence extends from an ATG at nucleotide 949 through a TAG stop codon at nucleotide 6063 in SEQ ID NO:9. The deduced amino acid sequence is given in SEQ ID NO:10.

TABLE 6

```
Sequence Range 1 to 7366
     >PstI                          >StuI
     |                              |
     |        *         *         * |       *         *         *
     CTGCAGAGGG CTGGTAAAGA CCGCCTCGGG ATCGAGGCCT TTGAGACGGG CACAAGCCGC CGCAGCCTCC
                                100
         *         *         *         *         *         *         *
     TCTTCGAAGG TGTCTCGAAC GTCCACATCG GTGAATCCGT AGCAGTGCTC ATTGCCATTG AGCAGCACCG
                                                                  200
         *         *         *         *         *         *         *
     AGGTGTGGCG CATCAGATAT ATTTTCATCA GTGGATTATT AGGGTATCGG TCAGAAAAAG CCTTCCGAAT
                                                              >ClaI
                                                              |
         *         *         *         *         *         | *         *
     CCGACAAAGA TAGTAGAAAG AGAGTGCATC TGAAAACAGA TCATTCGAGG ATTATCGATC AACTGAAAAG
                    300
         *         *         *         *         *         *         *
     GCAGGAGTTG TTTTGCGTTT TGGTTCGGAA AATTACCTGA TCAGCATTCG TAAAAACGTG GCGCGAGAAT
                                                400
         *         *         *         *         *         *         *
     TTTTTCGTTT TGGCGCGAGA ATTAAAAATT TTTGGAACCA CAGCGAAAAA AATCTCGCGC CGTTTTCTCA
         *         *         *         *         *         *         *
     GGATTTACAG ACCACAATCC GAGCATTTTC GGTTCGTAAT TCATCGAAGA GACAGGTTTT ACCGCATTGA
         500
         *         *         *         *         *         *         *
     AATCAGAGAG AGAATATCCG TAGTCCAACG GTTCATCCTT ATATCAGAGG TTAAAAGATA TGGTACGCTC
                                                600
         *         *         *         *         *         *         *
     ATCGAGGAGC TGATTGGCTT AGTAGGTGAG ACTTTCTTAA GAGACTATCG GCACCTACAG GAAGTTCATG
                                                                      700
         *         *         *         *         *         *         *
     GCACACAAGG CAAAGGAGGC AATCTTCGCA GACCGGACTC ATATCAAAAG GATGAAACGA CTTTTCCATA
         *         *         *         *         *         *         *
     CGACAACCAA ATAGCCGTCT ACGGTAGACG AATGCAAACC CAATATGAGG CCATCAATCA ATCCGAATGA
                                800
         *         *         *         *         *         *         *
     CAGCTTTTGG GCAATATATT ATGCATATTT TGATTCGCGT TTAAAGGAAA AGTGCATATA TTTGCGATTG
                                                                  900
         *         *         *         *         *         *         *
     TGGTATTTCT TTCGGTTTCT ATGTGAATTT TGTCTCCCAA GAAGACTTTA TAATGCATAA ATACAGAAGG
         *         *         *         *         *         *
     GGTACTACAC AGTAAAATCA TATTCTAATT TCATCAAA ATG AAA AAC TTG AAC AAG TTT GTT TCG
                                               M   K   N   L   N   K   F   V   S>
                             1000
         *         *         *         *         *         *
     ATT GCT CTT TGC TCT TCC TTA TTA GGA GGA ATG GCA TTT GCG CAG CAG ACA GAG TTG
     I   A   L   C   S   S   L   L   G   G   M   A   F   A   Q   Q   T   E   L>

*         *         *         *         *
     GGA CGC AAT CCG AAT GTC AGA TTG CTC GAA TCC ACT CAG CAA TCG GTG ACA AAG GTT
     G   R   N   P   N   V   R   L   L   E   S   T   Q   Q   S   V   T   K   V>

1100
     *         *         *         *         *         *         *
     CAG TTC CGT ATG GAC AAC CTC AAG TTC ACC GAA GTT CAA ACC CCT AAG GGA ATC GGA
     Q   F   R   M   D   N   L   K   F   T   E   V   Q   T   P   K   G   I   G>

1200
         *         *         *         *         *         *         *
     CAA GTG CCG ACT TAT ACA GAA GGG GTT AAT CTT TCC GAA AAA GGG ATG CCT ACG CTT
     Q   V   P   T   Y   T   E   G   V   N   L   S   E   K   G   M   P   T   L>

*         *         *         *         *         *
     CCC ATT CTA TCA CGC TCT TTG GCG GTT TCA GAC ACT CGT GAG ATG AAG GTA GAG GTT
     P   I   L   S   R   S   L   A   V   S   D   T   R   E   M   K   V   E   V>
```

TABLE 6-continued

```
                                1300
        *           *            *            *           *
GTT TCC TCA AAG TTC ATC GAA AAG AAA AAT GTC CTG ATT GCA CCC TCC AAG GGC ATG
 V   S   S   K   F   I   E   K   K   N   V   L   I   A   P   S   K   G   M>

*           *            *            *           *            *
ATT ATG CGT AAC GAA GAT CCG AAA AAG ATC CCT TAC GTT TAT GGA AAG AGC TAC TCG
 I   M   R   N   E   D   P   K   K   I   P   Y   V   Y   G   K   S   Y   S>

1400
    *           *            *            *           *            *
CAA ACC AAA TTC TTC CCG GGA GAG ATC GCC ACG CTT GAT GAT CCT TTT ATC CTT CGT
 Q   N   K   F   F   P   G   E   I   A   T   L   D   D   P   F   I   L   R>

*           *            *            *           *
GAT GTG CGT GGA CAG GTT GTA AAC TTT GCG CCT TTG CAG TAT AAC CCT GTG ACA AAG
 D   V   R   G   Q   V   V   N   F   A   P   L   Q   Y   N   P   V   T   K>

1500
 *           *            *            *            *           *
ACG TTG CGC ATC TAT ACG GAA ATC ACT GTG GCA GTG AGC GAA ACT TCG GAA CAA GGC
 T   L   A   I   Y   T   E   I   T   V   A   V   S   E   T   S   E   Q   G>

1600
        *            *           *            *           *            *
AAA AAT ATT CTG AAC AAG AAA GGT ACA TTT GCC GGC TTT GAA GAC ACA TAC AAG CGC
 K   N   I   L   N   K   K   G   T   F   A   G   F   E   D   T   Y   K   R>

*           *            *            *           *
ATG TTC ATG AAC TAC GAG CCG GGG CGT TAC ACA CCG GTA GAG GAA AAA CAA AAT GGT
 M   F   M   N   Y   E   P   G   R   Y   T   P   V   E   E   K   Q   N   G>

1700
 *           *            *            *            *           *
CGT ATG ATC GTC ATC GTA GCC AAA AAG TAT GAG GGA GAT ATT AAA GAT TTC GTT GAT
 R   M   I   V   I   V   A   K   K   Y   E   G   D   I   K   D   F   V   D>

*           *            *            *           *            *
TGG AAA AAC CAA CGC GGT CTC CGT ACC GAG GTG AAA GTG GCA GAA GAT ATT GCT TCT
 W   K   N   Q   R   G   L   R   T   E   V   K   V   A   E   D   I   A   S>

1800
    *           *            *            *           *            *
CCC GTT ACA GCT AAT GCT ATT CAG CAG TTC GTT AAG CAA GAA TAC GAG AAA GAA GGT
 P   V   T   A   N   A   I   Q   Q   F   V   K   Q   E   Y   E   K   E   G>

*           *            *            *           *
AAT GAT TTG ACC TAT GTT CTT TTG GTT GGC GAT CAC AAA GAT ATT CCT GCC AAA ATT
 N   D   L   T   Y   V   L   L   V   G   D   H   K   D   I   P   A   K   I>

1900
 *           *            *            *            *           *
ACT CCG GGG ATC AAA TCC GAC CAG GTA TAT GGA CAA ATA GTA GGT AAT GAC CAC TAC
 T   P   G   I   K   S   D   Q   V   Y   G   Q   I   V   G   N   D   H   Y>

2000
        *            *           *            *           *            *
AAC GAA GTC TTC ATC GGT CGT TTC TCA TGT GAG AGC AAA GAG GAT CTG AAG ACA CAA
 N   E   V   F   I   G   R   F   S   C   E   S   K   E   D   L   K   T   Q>

>ClaI
 |
 |   *           *            *            *           *
ATC GAT CGG ACT ATT CAC TAT GAG CGC AAT ATA ACC ACG GAA GAC AAA TGG CTC GGT
 I   D   A   T   I   H   Y   E   R   N   I   T   T   E   D   K   W   L   G>

2100
    *           *            *            *           *
CAG GCT CTT TGT ATT GCT TCG GCT GAA GGA GGC CCA TCC GCA GAC AAT GGT GAA AGT
 Q   A   L   C   I   A   S   A   E   G   G   P   A   D   N   G   E   S>

>EcoR5
 |
 |  *           *            *            *           *            *
GAT ATC CAG CAT GAG AAT GTA ATC GCC AAT CTG CTT ACC CAG TAT GGC TAT ACC AAG
 D   I   Q   H   E   N   V   I   A   N   L   L   T   Q   Y   G   Y   T   K>

2200
```

TABLE 6-continued

```
      *           *           *           *           *
ATT ATC AAA TGT TAT GAT CCG GGA GTA ACT CCT AAA AAC ATT ATT GAT GCT TTC AAC
 I   I   K   C   Y   D   P   G   V   T   P   K   N   I   I   D   A   F   N>

*           *           *           *           *           *
GGA GGA ATC TCG TTG GTC AAC TAT ACG GGC CAC GGT AGC GAA ACA GCT TGG GGT ACG
 G   G   I   S   L   V   N   Y   T   G   H   G   S   E   T   A   W   G   T>

2300
      *           *           *           *           *           *
TCT CAC TTC GGC ACC ACT CAT GTG AAG CAG CTT ACC AAC AGC AAC CAG CTA CCG TTT
 S   H   F   G   T   T   H   V   K   Q   L   T   N   S   N   Q   L   P   F>

>SphI
                                                      |
                                                      |           2400
      *           *           *           *           |*          *
ATT TTC GAC GTA GCT TGT GTG AAT GGC GAT TTC CTA TTC AGC ATG CCT TGC TTC GCA
 I   F   D   V   A   C   V   N   G   D   F   L   F   S   M   P   C   F   A>

*           *           *           *           *
GAA GCC CTG ATG CGT GCA CAA AAA GAT GGT AAG CCG ACA GGT ACT GTT GCT ATC ATA
 E   A   L   M   R   A   Q   K   D   G   K   P   T   G   T   V   A   I   I>

2500
  *           *           *           *           *           *
GCG TCT ACG ATC AAC CAG TCT TGG GCT TCT CCT ATG CGC GGG CAG GAT GAT ATG AAC
 A   S   T   I   N   Q   S   W   A   S   P   M   R   G   Q   D   D   M   N>

*           *           *           *           *           *
GAA ATT CTG TGC GAA AAA CAC CCG AAC AAC ATC AAG CGT ACT TTC GGT GGT GTC ACC
 E   I   L   C   E   K   H   P   N   N   I   K   R   T   F   G   G   V   T>

2600
      *           *           *           *           *           *
ATG AAC GGT ATG TTT GCT ATG GTG GAA AAG TCT AAA AAG GAT GGT GAG AAG ATG CTC
 M   N   G   M   F   A   M   V   E   K   Y   K   K   D   G   E   K   M   L>

*           *           *           *           *           *
GAC ACA TGG ACT GTT TTC GGC GAC CCC TCG CTG CTC GTT CGT ACA CTT GTC CCG ACC
 D   T   W   T   V   F   G   D   P   S   L   L   V   R   T   L   V   P   T>

2700
      *           *           *           *           *           *
AAA ATG CAG GTT ACG GCT CCG GCT CAG ATT AAT TTG ACG GAT GCT TCA GTC AAC GTA
 K   M   Q   V   T   A   P   A   Q   I   N   L   T   D   A   S   V   N   V>

*           *           *           *           *           *
TCT TGC GAT TAT AAT GGT GCT ATT GCT ACC ATT TCA GCC AAT GGA AAG ATG TTC GGT
 S   C   D   Y   N   G   A   I   A   T   I   S   A   N   G   K   M   F   G>

>PstI
        |
2800    |
  *     |     *           *           *           *           *
TCT GCA GTT GTC GAA AAT GGA ACA GTC ACA ATC AAT CTG ACA GGT CTG ACA AAT GAA
 S   A   V   V   E   N   G   T   A   T   I   N   L   T   G   L   T   N   E>

*           *           *           *       2900  *           *
AGC ACG CTT ACC CTT ACA GTA GTT GGT TAC AAC AAA GAG ACG GTT ATT AAG ACT ATC
 S   T   L   T   L   T   V   V   G   Y   N   K   E   T   V   I   K   T   I>

*           *           *           *           *           *
AAC ACT AAT GGT GAG CCT AAC CCC TAC CAG CCC GTT TCT AAC TTG ACA GCT ACA ACG
 N   T   N   G   E   P   N   P   Y   Q   P   V   S   N   L   T   A   T   T>

3000
      *           *           *           *           *           *
CAG GGT CAG AAA GTA ACG CTC AAG TGG GAT GCA CCG AGC ACG AAA ACC AAT GCA ACC
 Q   G   Q   K   V   T   L   K   W   D   A   P   S   T   E   T   N   A   T>

*           *           *           *           *           *
ACT AAT ACC GCT CGC AGC GTG GAT GGC ATA CGA GAA TTG GTT CTT CTG TCA GTC AGC
 T   N   T   A   R   S   V   D   G   I   R   E   L   V   L   L   S   V   S>

3100
      *           *           *           *           *           *
GAT GCC CCC GAA CTT CTT CGC AGC GGT CAG GCC GAG ATT GTT CTT GAA GCT CAC GAT
```

TABLE 6-continued

```
  D   A   P   E   L   L   R   S   G   Q   A   E   I   V   L   E   A   E   D>
              >BamH1
              |
      *       |       *               *               *               *
 GTT TGG AAT GAT GGA TCC GGT TAT CAG ATT CTT TTG GAT GCA GAC CAT GAT CAA TAT
  V   W   N   D   G   S   G   Y   Q   I   L   L   D   A   D   H   D   Q   Y>

3200
  *               *               *               *               *
 GGA CAG GTT ATA CCC AGT GAT ACC CAT ACT CTT TGG CCG AAC TGT AGT GTC CCG GCC
  G   Q   V   I   P   S   D   T   H   T   L   W   P   N   C   S   V   P   A>

3300
          *               *               *               *               *
 AAT CTG TTC GCT CCG TTC GAA TAT ACT GTT CCG GAA AAT GCA GAT CCT TCT TGT TCC
  S   L   F   A   P   F   E   Y   T   V   P   E   N   A   D   P   S   C   S>

*               *               *               *               *
 CCT ACC AAT ATG ATA ATG GAT GGT ACT GCA TCC GTT AAT ATA CCG GCC GGA ACT TAT
  P   T   N   M   I   M   D   G   T   A   S   V   N   I   P   A   G   T   Y>

3400
  *               *               *               *               *
 GAC TTT GCA ATT GCT GCT CCT CAA GCA AAT GCA AAG ATT TGG ATT GCC GGA CAA GGA
  D   F   A   I   A   A   P   Q   A   N   A   K   I   W   I   A   G   Q   G>

*               *               *               *               *
 CCG ACG AAA GAA GAT GAT TAT GTA TTT GAA GCC GGT AAA AAA TAC CAT TTC CTT ATG
  P   T   K   E   D   D   Y   V   F   E   A   G   K   K   Y   E   F   L   M>

3500
          *               *               *               *               *
 AAG AAG ATG GGT AGC GGT GAT GGA ACT GAA TTG ACT ATA AGC GAA GGT GGT GGA AGC
  K   K   M   G   S   G   D   G   T   E   L   T   I   S   E   G   G   G   S>

*               *               *               *
 GAT TAC ACC TAT ACT GTC TAT CGT GAC GGC ACG AAG ATC AAG GAA GGT CTG ACG GCT
  D   Y   T   Y   T   V   Y   R   D   G   T   K   I   K   E   G   L   T   A>

3600
  *               *               *               *               *       *
 ACG ACA TTC GAA GAA GAC GGT GTA GCT ACG GGC AAT CAT GAG TAT TGC GTG GAA GTT
  T   T   F   E   E   D   G   V   A   T   G   N   H   E   Y   C   V   E   V>

>BamH1
                                                                  |
                                                  3700            |
          *               *               *               *       |       *
 AAG TAC ACA GCC GGC GTA TCT CCG AAG GTA TGT AAA GAC GGT ACG GTA GAA GGA TCC
  K   Y   T   A   G   V   S   P   K   V   C   K   D   G   T   V   E   G   S>

*               *               *               *
 AAT GAA TTT GCT CCT GTA CAG AAC CTG ACC GGT AGT GCA GTC GGC CAG AAA TGA ACG
  N   E   F   A   P   V   Q   N   L   T   G   S   A   V   G   Q   K   V   T>

>Asp718
                      |
                      |           3800
  *       *           |   *               *               *               *
 CTC AAG TGG GAT GCA CCT AAT GGT ACC CCG AAT CCA AAT CCG AAT CCG AAT CCG AAT
  L   K   W   D   A   P   N   G   T   P   N   P   N   P   N   P   N   P   N>

*               *               *               *               *
 CCC GGA ACA ACA CTT TCC GAA TCA TTC GAA AAT GGT AAT CCT GCC TCA TGG AAG
  P   G   T   T   L   S   E   S   F   E   N   G   I   P   A   S   W   K>

>ClaI
      |
      |           3900
      |   *               *               *               *               *
 ACG ATC GAT GCA GAC GGT GAC GGG CAT GGC TGG AAG CCT GGA AAT GCT CCC GGA ATC
  T   I   D   A   D   G   D   G   H   G   W   K   P   G   N   A   P   G   I>

*               *               *               *               *
 GCT GGC TAC AAT AGC AAT GGT TGT GTA TAT TCA GAG TCA TTC GGT CTT GGT GGT ATA
  A   G   Y   N   S   N   G   C   V   Y   S   E   S   F   G   L   G   G   I>

4000
```

TABLE 6-continued

```
                *                    *                    *                    *                    *                    *
GGA CTT CTT ACC CCT GAC AAC TAT CTG ATA ACA CCG GCA TTG GAT TTG CCT AAC GGA
 G   V   L   T   P   D   N   Y   L   I   T   P   A   L   D   L   P   N   G>

4100
             *                    *                    *                    *                    *                    *
GGT AAG TTG ACT TTC TGG GTA TGC GCA CAG GAT GCT AAT TAT GCA TCC GAG CAC TAT
 G   K   L   T   F   W   V   C   A   Q   D   A   N   Y   A   S   E   H   Y>

*                    *                    *                    *                    *
GCG GTG TAT GCA TCT TCG ACC GGT AAC GAT GCA TCC AAC TTC ACG AAT GCT TTG TTG
 A   V   Y   A   S   T   G   N   D   A   S   N   F   T   N   A   L   L>

4200
             *                    *                    *                    *                    *                    *
GAA GAG ACG ATT ACG GCA AAA GGT GGT CGC TCG CCG GAA GCT ATT CGT GGT CGT ATA
 E   E   T   I   T   A   K   G   V   R   S   P   E   A   I   R   G   A   I>

*                    *                    *                    *                    *                    *
CAG GGT ACT TGG CGC CAG AAG ACG GTA GAC CTT CCC GCA GGT ACG AAA TAT GTT GCT
 Q   G   T   W   R   Q   K   T   V   D   L   P   A   G   T   K   Y   V   A>

4300
                    *                    *                    *                    *                    *                    *
TTC CGT CAC TTC CAA AGC ACG GAT ATG TTC TAC ATC GAC CTT GAT GAG GTT GAG ATC
 F   R   H   F   Q   S   T   D   M   F   Y   I   D   L   D   E   V   E   I>

*                    *                    *                    *                    *                    *
AAG GCC AAC GGC AAG CGC GCA GAC TTC ACG GAA ACG TTC GAG TCT TCT ACT CAT GGA
 K   A   N   G   K   R   A   D   F   T   E   T   F   E   S   S   T   H   G>

>Cla1
                                                |
    4400                                        |
       *                    *                 *|                    *                    *                    *
GAG GCA CCG GCG GAA TGG ACT ACT ATC GAT GCC GAT GGC GAT GGT CAG GGT TGG CTC
 E   A   P   A   E   W   T   T   I   D   A   D   G   D   G   Q   G   W   L>

4500
             *                    *                    *                    *                    *                    *
TGT CTG TCT TCC GGA CAA TTG GAC TGG CTG ACA GCT CAT GGC GGC ACC AAC GTA GTA
 C   L   S   S   G   Q   L   D   W   L   T   A   H   G   G   T   N   V   V>

*                    *                    *                    *                    *                    *
GCC TCT TTT TCA TGG AAT GGA ATG GCT TTG AAT CCT GAT AAC TAT CTC ATC TCA AAG
 A   S   F   S   W   N   G   M   A   L   N   P   D   N   Y   L   I   S   K>

4600
       *                    *                    *                    *                    *                    *
GAT GTT ACA GGC GCA ACG AAG GTA AAG TAC TAC TAT GCA GTC AAC GAC GGT TTT CCC
 D   V   T   G   A   T   K   V   K   Y   Y   Y   A   V   N   D   G   F   P>

*                    *                    *                    *                    *                    *
GGG GAT CAC TAT GCG GTG ATG ATC TCC AAG ACG GGC ACG AAC GCC GGA GAC TTC ACG
 G   D   H   Y   A   V   M   I   S   K   T   G   T   N   A   G   D   F   T>

4700
                    *                    *                    *                    *                    *
GTT GTT TTC GAA GAA ACG CCT AAC GGA ATA AAT AAG GGC GGA GCA AGA TTC GGT CTT
 V   V   F   E   E   T   P   N   G   I   N   K   G   G   A   R   F   G   L>

*                    *                    *                    *                    *                    *
TCC ACG GAA GCC AAT GGC GCC AAA CCT CAA AGT GTA TGG ATC GAG CGT ACG GTA GAT
 S   T   E   A   N   G   A   K   P   Q   S   V   W   I   E   R   T   V   D>

4800
       *                    *                    *                    *                    *                    *
TTG CCT GCG GGC ACG AAG TAT GTT GCT TTC CGT CAC TAC AAT TGC TCG GAT TTG AAC
 D   P   A   G   T   K   Y   V   A   F   R   H   Y   N   C   S   D   L   N>

>Nco1
                                          |
                                          |                    4900
             *                    *       |            *                    *
TAC ATT CTT TTG GAT GAT ATT CAG TTC ACC ATG GGT GGC AGC CCC ACC CCG ACC GAT
 Y   I   L   L   D   D   I   Q   F   T   M   G   G   S   P   T   P   T   D>

*                    *                    *                    *                    *                    *
TAT ACC TAC ACG GTG TAT CGT GAC GGT ACG AAG ATC AAG GAA GGT CTG ACC GAA ACG
```

TABLE 6-continued

```
      Y   T   Y   T   V   Y   R   D   G   T   K   I   K   E   G   L   T   E   T>
                                            5000
              *               *               *               *               *               *
    ACC TTC GAA GAA GAC GGC GTA GCT ACA GGC AAT CAT GAG TAT TGC GTG GAA GTG AAG
      T   F   E   E   D   G   V   A   T   G   N   H   E   Y   C   V   E   V   K>

*               *               *               *               *
    TAC ACA GCC GGC GTA TCT CCG AAA GAG TGC GTA AAC GTA ACT ATT AAT CCG ACT CAG
      Y   T   A   G   V   S   P   K   E   C   V   N   V   T   I   N   P   T   Q>

5100
    *               *               *               *               *               *
    TTC AAT CCT GTA AAG AAC CTG AAG GCA CAA CCG GAT GGC GGC CAC GTG GTT CTC AAG
      F   N   P   V   K   N   L   K   A   Q   P   D   G   G   D   V   V   L   K>

*               *               *               *               *               *
    TGG GAA GCC CCG AGC GCA AAA AAG ACA GAA GGT TCT CGT GAA GTA AAA CGG ATC GGA
      W   E   A   P   S   A   K   K   T   E   G   S   R   E   V   K   R   I   G>

5200
                      *               *               *               *               *               *
    GAC GGT CTT TTC GTT ACG ATC GAA CCT GCA AAC GAT GTA CGT GCC AAC GAA GCC AAG
      D   G   L   F   V   T   I   E   P   A   N   D   V   R   A   N   E   A   K>

5300
              *               *               *               *               *               *
    GTT GTG CTC GCA GCA GAC AAC GTA TGG GGA GAC AAT ACG GGT TAC CAG TTC TTG TTG
      V   V   L   A   A   D   N   V   W   G   D   N   T   G   Y   Q   F   L   L>

*               *               *               *               *               *
    GAT GCC GAT CAC AAT ACA TTC GGA AGT GTC ATT CCG GCA ACC GGT CCT CTC TTT ACC
      D   A   D   H   N   T   F   G   S   V   I   P   A   T   G   P   L   F   T>

5400
              *               *               *               *               *               *
    GGA ACA GCT TCT TCC AAT CTT TAC AGT GCG AAC TTC GAG TAT TTG ATC CCG GCC AAT
      G   T   A   S   S   N   L   T   S   A   N   F   E   Y   L   I   P   A   N>

*               *               *               *               *
    GCC GAT CCT GTT GTT ACT ACA CAG AAT ATT ATC GTT ACA GGA CAG GGT GAA GTT GTA
      A   D   P   V   V   T   T   Q   N   I   I   V   T   G   Q   G   E   V   V>

5500
              *               *               *               *               *               *
    ATC CCC GGT GGT GTT TAC GAC TAT TGC ATT ACG AAC CCG GAA CCT GCA TCC GGA AAG
      I   P   G   G   V   Y   D   Y   C   I   T   N   P   E   P   A   S   G   K>

*               *               *               *               *               *
    ATG TGG ATC GCA GGA GAT GGA GGC AAC CAG CCT GCA CGT TAT GAC GAT TTC ACA TTC
      M   W   I   A   G   D   G   G   N   Q   P   A   R   Y   D   D   F   T   F>

5600
              *               *               *               *               *
    GAA GCA GGC AAG AAG TAC ACC TTC ACG ATG CGT CGC GCC GGA ATG GGA GAT GGA ACT
      E   A   G   K   K   Y   T   F   T   M   R   R   A   G   M   G   D   G   T>

5700
      *               *               *               *               *               *
    GAT ATG GAA GTC GAA GAC GAT TCA CCT GCA AGC TAT ACC TAT ACA GTC TAT CGT GAC
      D   M   E   V   E   D   D   S   P   A   S   Y   T   Y   T   V   Y   R   D>

*               *               *               *               *               *
    GGC ACG AAG ATC AAG GAA GGT CTG ACC GAA ACG ACC TAC CGC CAT GCA GGA ATG AGT
      G   T   K   I   K   E   G   L   T   E   T   T   Y   A   D   A   G   M   S>

5800
              *               *               *               *               *               *
    GCA CAA TCT CAT GAG TAT TGC GTA GAG GTT AAG TAC GCA GCC GGC GTA TCT CCG AAG
      A   Q   S   H   E   Y   C   V   E   V   K   Y   A   A   G   V   S   P   K>

*               *               *               *               *
    GTT TGT GTG GAT TAT ATT CCT GAC GGA GTG GCA GAC GTA ACG GCT CAG AAG CCT TAC
      V   C   V   D   Y   I   P   D   G   V   A   D   V   T   A   Q   K   P   Y>

5900
              *               *               *               *               *               *
    ACG CTG ACA GTT GTT GGA AAG ACG ATC ACG GTA ACT TGC CAA GGC GAA GCT ATG ATC
      T   L   T   V   V   G   K   T   I   T   V   T   C   Q   G   E   A   M   I>
```

TABLE 6-continued

```
           *                *                *                *                *                *
TAC GAC ATG AAC GGT CGT CGT CTG GCA GCC GGT CGC AAC ACA GTT GTT TAC ACG GCT
 Y   D   M   N   G   R   R   L   A   A   G   R   N   T   V   V   Y   T   A>
        6000
           *                *                *                *                *
CAG GGC GGC TAC TAT GCA GTC ATG GTT GTC GTT GAC GGC AAG TCT TAC GTA GAG AAA
 Q   G   G   Y   Y   A   V   M   V   V   V   D   G   K   S   Y   V   E   K>
                                                                  6100
   *                *                *                *                *                *                *
CTC GCT GTA AAG TAA TTCTGTC TTGGACTCGG AGACTTTGTG CAGACACTTT TAATATAGGT
 L   A   V   K   *>

>Cla1
                          |
     *                *   |   *                *                *                *                *
CTGTAATTGT CTCAGAGTAT GAATCGATCG CCCGACCTCC TTTTAAGGAA TGCTGGGCGA CTTCGTTTTT
               6200
     *                *                *                *                *                *                *
ATGCCTATTA TTCTAATATA CTTCTGAAAC AATTTGTTCC AAAAAGTTGC ATGAAAGAT TATCTTACTA
                                                  6300
     *                *                *                *                *                *                *
TCTTTGCACT GCAAAAGGGG AGTTTCCTAA GGTTTTCCCC GGAGTAGTAC GGTAATAACG GTGTGGTAGT

>Pvu2
    |
    | *                *                *                *                *                *                *
TCAGCTGGTT AGAATACCTG CCTGTCACGC AGGGGGTCGC GGGTTCGAGT CCCGTCCATA CCGCTAAATA
        6400
     *                *                *                *                *                *                *
GCTGAAAGAT AGGCTATAGG TCATCTGAAG CAATTTTAGA AACGAATCCA AAAGCGTCTT AATTCCAACG
                                  6500
     *                *                *                *                *                *                *
AATTAAGGCG CTTTTTCTTT GTCGCCACCC CACACGTCGG ATGAGGTTCG GAATAGGCGT ATATTCCGTA
                                                                                             6600
     *                *                *                *                *                *                *
AATATGCCTC CGGTGGTTCC ATTTTGGTTA CAAAAAACAA AGGGGCTGAA AATTGTAACC ACAGACGACG

>Nde1
                                                               |
     *                *                *                *      |   *                *                *
TTAAGACGAT GTTTAGACGA TTGACAAATT ACTCTGTTTC AAAATCATAT GTCGAACTTT GTAGCCGTAT
                                  6700
     *                *                *                *                *                *                *
GGTTACACTA ATTTTGGAGC AAAATGAAGA GTCAATTTCG TTCAGTTTTT TACTTGCGCA GCAATTACAT
                                                                        6800
     *                *                *                *                *                *                *
CAACAAAGAA GGTAAAACTC CTGTCCTTAT TCGTATTTAT CTGAATAAGG AACGCCTGTC GTTGGGTTCG
     *                *                *                *                *                *                *
ACAGGGCTGG CTGTTAATCC CATACAATGG GATTCAGAAA AAGAGAAAGT CAAAGGACAT AGTGCAGAAG
             6900
     *                *                *                *                *                *                *
CACTTGAAGT CAATCGAAAG ATCGAAGAAA TCAGGGCTGA TATTCTGACC ATTTACAAAC GTTTGGAAGT
                                                  7000
     *                *                *                *                *                *                *
AACAGTAGAT GATTTGACGC CGGAGAGGAT CAAATCGGAA TACTGCGGAC AGACGGATAC ATTAAACAGT
     *                *                *                *                *                *                *
ATAGTGGAAC TTTTCGATAA ACATAACGAG GATGTCCGGG CCCAGGTGGG AATCAATAAA ACGGCTGCCA
        7100
     *                *                *                *                *                *                *
CTTTACAAAA ATACGAAAAC AGCAAACGGC ATTTTACCCG ATTCCTCAAA GCGAAGTACA CACGAACGGA
                                  7200
     *                *                *                *                *                *                *
TCTCAAATTC TCAGAGCTTA CCCCGTTGGT CATTCATAAC TTTGAGATAT ATCTGCTGAC TGTAGCCCAT
```

TABLE 6-continued

```
                                  >Hind3
                                      |
         *            *          *   |
   TGTTGCCCGA ATACGGCAAC CAAAATCTTG AAGCTT
```

A comparison of the deduced amino acid sequence of gingipain-2 with sequences of cysteine proteases indicates some homology around the residues making up the active site (Chua et al. 1988, *J. Exp. Med.* 167, 175–182) (Table 7). The homology between gingipain-2 and cysteine proteases is underlined and is encoded at nucleotide residues 2743 to 2781 in Table 5.

39.4 kDa, consistent with that estimated by gel electrophoresis. The 17 kDa hemagglutinin component has an amino acid sequence as given in SEQ ID NO:10 at amino acids 1092–1429, and a calculated molecular weight of 37.1 kDa. The 27 KDa hemagglutinin component has an amino acid sequence extending from amino acids 1430–1704 in SEQ ID NO:10, and a calculated molecular weight of 29.6 kDa.

TABLE 8

Alignment of Hemagglutinin Domain Sequences shown in FIG. 2.

| | | |
|---|---|---|
| RGP[1] | amino acids 670–674 of SEQ ID NO:10 | LtaTT |
| HGP-44kDa[2] | amino acids 865–913 of SEQ ID NO:10 | dYTYTVYRDGKIKEGLTaTTfeedGvatgnHEYCVEVKYtAGVSPKvC |
| HGP-17kDa | amino acids 1320–1368 of SEQ ID NO:10 | dYTYTVYRDGKIKEGLTeTTfeedGvatgnHEYCVEVKYtAGVSPKeC |
| HGP-27kDa | amino acids 1580–1626 of SEQ ID NO:10 | sYTYTVYRDGKIKEGLTeTTyrdaGmsaqsHEYCVEVKYaAGVSPKvC |

[1]RGP means Arg-gingipain proteolytic component
[2]HGP means Hemagglutinin protein component

TABLE 7

Composite alignment of the deduced partial amino acid sequence of gingipain-2 with sequences of known cysteine proteases

| | |
|---|---|
| Gingipain: | SCDYNGAIATI SA (SEQ ID NO:11) |
| Der p 1: | SCWAFSGVAATFSA (SEQ ID NO:12) |
| Rat cathepsin H: | SCWIFSTIGALFSA (SEQ ID NO.13) |
| Chinese gooseberry actinidin: | GCWAFSAIATVEGI (SEQ ID NO:14) |
| Papaya papain: | SCWAFSAVVTIFGI (SEQ ID NO:15) |
| Human cathepsin B: | SCWAFGAVEAISDR (SEQ ID NO:16) |

The first serine residue of the proteolytic component of High Molecular Weight Arg-gingipain shown in this table is encoded at nucleotides 2743–2745 of SEQ ID NO:4. SEQ ID NO:4 comprises the exemplified coding sequence for the Arg-gingipain-2 mature protein from *P. gingivalis* strain H66 (see also Tables 5 and 6). The skilled artisan recognizes that other *P. gingivalis* strains can have coding sequences for a protein with the distinguishing characteristics of an Arg-gingipain; those coding sequences may be identical to or synonymous with the exemplified coding sequence, or there may be some variation(s) in the encoded amino acid sequence. An Arg-gingipain coding sequence from a *P. gingivalis* strain other than H66 can be identified by, e.g. hybridization to a polynucleotide or an oligonucleotide having the whole or a portion of the exemplified coding sequence for mature gingipain, under stringency conditions appropriate to detect a sequence of at least 70% homology.

Cleavage of the precursor protein after the Arg residue at amino acid 227 removes the N-terminal precursor portion and after the Arg residue at amino acid 719, 1091 and 1429 releases a low molecular weight Arg-gingipain and three hemagglutinin components. The 44 kDa hemagglutin component has an amino acid sequence as given in SEQ ID NO:10 from 720–1091, with calculated molecular weight of Table 8 is the result of sequence comparison of the 44 kDa, 27 kDa and 17 kDa hemagglutinin domains of Arg-gingipain complexes, alignment of regions of amino acid identity, which without wishing to be the domains responsible for hemagglutinin activity. Identical amino acids among all hemagglutinin domains are in capital letters, and amino acids which are not conserved are shown in lower case letters. In the case of the proteolytic component, only a limited region with significant match is shown.

A genomic DNA library was also prepared from virulent *P. gingivalis* W50. Two clones were identified as containing Arg-gingipain coding sequence. 0.5 and 3.5 kb BamHI fragments were sequenced; it exhibited 99% nucleotide sequence identity with about 3160 plus 557 bp of *P. gingivalis* H66 DNA containing Arg-gingipain coding sequence. A comparison of the deduced amino acid sequences of the encoded Arg-gingipain sequences revealed 99% identity.

Tables 5 and 6 both represent sequences from *P. gingivalis*. However, it is understood that there will be some variations in the amino acid sequences and encoding nucleic acid sequences for Arg-gingipain from different *P. gingivalis* strains. The ordinary skilled artisan can readily identify and isolate Arg-gingipain-encoding sequences from other strains where there is at least 70% homology to the specifically exemplified sequences herein using the sequences provided herein taken with what is well known to the art. Also within the scope of the present invention are Arg-gingipain where the protease or proteolytic component has at least about 85% amino acid sequence identity with an amino acid sequence exemplified herein.

It is also understood by the skilled artisan that there can be limited numbers of amino acid substitutions in a protein without significantly affecting function, and that nonexemplified gingipain-1 proteins can have some amino acid sequence diversion from the exemplified amino acid sequence. Such naturally occurring variants can be identified, e.g., by hybridization to the exemplified (mature) Arg-gingipain-2 coding sequence (or a portion thereof capable of specific hybridization to Arg-gingipain sequences) under conditions appropriate to detect at least about 70% nucleotide sequence homology, preferably about 80%, more preferably about 90% and most preferably 95–100% sequence homology. Preferably the encoded Arg-gingipain protease or proteolytic component has at least about 85% amino acid sequence identity to an exemplified Arg-gingipain amino acid sequence.

It is well known in the biological arts that certain amino acid substitutions can be made in protein sequences without affecting the function of the protein. Generally, conservative amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure,* Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

The skilled artisan recognizes that other *P. gingivalis* strains can have coding sequences for a protein with the distinguishing characteristics of an Arg-gingipain; those coding sequences may be identical to or synonymous with the exemplified coding sequence, or there may be some variation(s) in the encoded amino acid sequence. An Arg-gingipain coding sequence from a *P. gingivalis* strain other than H66 can be identified by, e.g. hybridization to a polynucleotide or an oligonucleotide having the whole or a portion of the exemplified coding sequence for mature gingipain, under stringency conditions appropriate to detect a sequence of at least 70% homology.

A polynucleotide or fragment thereof is "substantially homologous" (or "substantially similar") to another polynucleotide if, when optimally aligned (with appropriate nucleotide insertions or deletions) with another polynucleotide, there is nucleotide sequence identity for approximately 60% of the nucleotide bases, usually approximately 70%, more usually about 80%, preferably about 90%, and more preferably about 95% to 100% of the nucleotide bases.

Alternatively, substantial homology (or similarity) exists when a polynucleotide or fragment thereof will hybridize to another under polynucleotide under selective hybridization conditions. Selectivity of hybridization exists under hybridization conditions which allow one to distinguish the target polynucleotide of interest from other polynucleotides. Typically, selective hybridization will occur when there is approximately 55% similarity over a stretch of about 14 nucleotides, preferably approximately 65%, more preferably approximately 75%, and most preferably approximately 90%. See Kanehisa (1984) *Nuc. Acids Res.,* 12:203–213. The length of homology comparison, as described, may be over longer stretches, and in certain embodiments will often be over a stretch of about 17 to 20 nucleotides, and preferably about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1 M, typically less than 500 mM, and preferably less than 200 mM. However, the combination of parameters is much more important than the measure of any single parameter (Wetmur and Davidson (1968) *J. Mol. Biol.* 31, 349–370).

An "isolated" or "substantially pure" polynucleotide is a polynucleotide which is substantially separated from other polynucleotide sequences which naturally accompany a native gingipain-1 sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to "encode" a polypeptide if, in its native state or when manipulated by methods known to those skilled in the art, it can be transcribed and/or translated to produce the polypeptide of a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term "recombinant" polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other Arg-gingipain coding sequences. Probes comprising synthetic oligonucleotides or other polynucleotides may be derived from naturally occurring or recombinant single or double stranded nucleic acids or be chemically synthesized. Polynucleotide probes may be labelled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a proteinase or a fragment thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli,* although other prokaryotes, such as *Bacillus subtilis* or Pseudomonas may also be used. Mammalian or other eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.,* 22: 1859–1862 or the triester method according to Matteuci et al. (1981) *J. Am. Chem. Soc.,* 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1987) *Current Protocols in Molecular Biology,* Greene Publishing and Wiley Interscience, New York; and Metzger et al. (1988) *Nature,* 334: 31–36. Many useful vectors for expression in bacteria, yeast, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The recombinant vectors containing the Arg-gingipain coding sequences of interest can be introduced (transformed, transfected) into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with gingipain-1-encoding polynucleotides of the present invention in compatible vectors or other expression vehicles and culturing such transformed host cells under conditions suitable to attain expression of the Arg-gingipain-encoding gene. The Arg-gingipain may then be recovered from the host cell and purified.

The coding sequence for the "mature" form of Arg-gingipain-2 is expressed after PCR site-directed mutagenesis and cloning into an expression vector suitable for use in *E. coli,* for example. Exemplary expression vectors for *E. coli* and other host cells are given, for example in Sambrook et al. (1989), vide infra, and in Pouwels et al. (Eds.) (1986) *Cloning Vectors,* Elsevier Science Publishers, Amsterdam, the Netherlands.

In order to eliminate leader sequences and precursor sequences at the 5' side of the coding sequence, a combination of restriction endonuclease cutting and site-directed mutagenesis via PCR using an oligonucleotide containing a desired restriction site for cloning (one not present in coding sequence), a ribosome binding site, an translation initiation codon (ATG) and the codons for the first amino acids of the mature Arg-gingipain-2. The oligonucleotide for site-directed mutagenesis at the 3' end of the coding sequence for mature gingipain-1 includes nucleotides encoding the carboxyterminal amino acids of mature gingipain-1, a translation termination codon (TAA, TGA or TAG), and a second suitable restriction endonuclease recognition site not present in the remainder of the DNA sequence to be inserted into the expression vector. The site-directed mutagenesis strategy is similar to that of Boone et al. (1990) *Proc. Natl. Acad. Sci. USA* 87: 2800–2804, as modified for use with PCR.

In another embodiment, polyclonal and/or monoclonal antibodies capable of specifically binding to a proteinase or fragments thereof are provided. The term antibody is used to refer both to a homogenous molecular entity, or a mixture such as a serum product made up of a plurality of different molecular entities. Monoclonal or polyclonal antibodies specifically reacting with the Arg-gingipains may be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2d ed., Academic Press, New York; and Ausubel et al. (1987) supra. Also, recombinant immunoglobulins may be produced by methods known in the art, including but not limited to the methods described in U.S. Pat. No. 4,816,567. Monoclonal antibodies with affinities of $10^8$ $M^{-1}$, preferably $10^9$ to $10^{10}$ or more are preferred.

Antibodies specific for Arg-gingipains may be useful, for example, as probes for screening DNA expression libraries or for detecting the presence of Arg-gingipains in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include but are not limited to U.S. Pat. Nos. 3,817,837; 3,850,752; 3,939,350; 3,996,345; 4,277,437; 4,275,149; and 4,366,241.

Antibodies specific for Arg-gingipain(s) and capable of inhibiting its proteinase activity may be useful in treating animals, including man, suffering from periodontal disease. Such antibodies can be obtained by the methods described above and subsequently screening the Arg-gingipain-specific antibodies for their ability to inhibit proteinase activity.

Compositions and immunogenic preparations including vaccine compositions comprising substantially purified recombinant Arg-gingipain(s) and a suitable carrier therefor are provided. Alternatively, hydrophilic regions of the proteolytic component or hemagglutinin component(s) of Arg-gingipain can be identified by the skilled artisan, and peptide antigens can be synthesized and conjugated to a suitable carrier protein (e.g., bovine serum albumin or keyhole limpet hemocyanin) for use in vaccines or in raising antibody specific for Arg-gingipains. Immunogenic compositions are those which result in specific antibody production when injected into a human or an animal. Such immunogenic compositions are useful, for example, in immunizing an animal, including humans, against inflammatory response and tissue damage caused by *P. gingivalis* in periodontal disease. The immunogenic preparations comprise an immunogenic amount of one or more Arg-gingipains or an immunogenic fragment(s) or subunit(s) thereof. Such immunogenic compositions may comprise one or more Arg-gingipain proteinases, or in combination with another protein or other immunogen. By "immunogenic amount" is meant an amount capable of eliciting the production of antibodies directed against Arg-gingipain(s) in an individual to which the vaccine has been administered.

Immunogenic carriers may be used to enhance the immunogenicity of the proteinases. Such carriers include but are not limited to proteins and polysaccharides, liposomes, and bacterial cells and membranes. Protein carriers may be joined to the proteinases to form fusion proteins by recombinant or synthetic means or by chemical coupling. Useful carriers and means of coupling such carriers to polypeptide antigens are known in the art.

The immunogenic compositions may be formulated by any of the means known in the art. Such vaccines are typically prepared as injectables, either as liquid solutions or suspensions. Solid forms suitable for solution in, or suspension in, liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

A 50 kDa Arg-gingipain or high molecular weight Arg-gingipain and fragments thereof may be formulated into immunogenic compositions as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The immunogenic Arg-gingipain compositions are administered in a manner compatible with the dosage formulation, and in such amount as will be prophylactically and/or therapeutically effective. The quantity to be administered, which is generally in the range of about 100 to 1,000 $\mu$g of protein per dose, more generally in the range of about 5 to 500 $\mu$g of protein per dose, depends on the subject to be treated, the capacity of the individual's immune system to synthesize antibodies, and the degree of protection desired. Precise amounts of the active ingredient required to be administered may depend on the judgment of the physician or doctor of dental medicine and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

Recombinant Arg-gingipains are useful in methods of identifying agents that modulate proteinase activity, e.g., by acting on the proteinase itself. One such method comprises the steps of incubating Arg-gingipain-1 (or high molecular weight Arg-proteinase) with a putative therapeutic agent; determining the activity of the proteinase incubated with the agent; and comparing the activity obtained in step with the activity of a control sample of proteinase that has not been incubated with the agent.

All references cited herein are hereby incorporated by reference in their entirety.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) Meth.

Enzymol. 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, N.Y., Old Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

The foregoing discussion and the following examples illustrate but are not intended to limit the invention. The skilled artisan will understand that alternative methods maybe used to implement the invention.

EXAMPLES

Example 1

Purification of Gingipain Enzymes

*P. gingivalis* strains H66 (ATCC 33277) and W50 (ATCC 53978) (virulent) were used in these studies (American Type Culture Collection, 12301 Parklawn Drive, Rockville, Md. 20852–1776). Cells were grown in 500 ml of broth containing 15.0 g Trypticase Soy Broth (Difco, Detroit, Mich.), 2.5 g yeast extract, 2.5 mg hemin, 0.25 g cysteine, 0.05 g dithiothreitol, 0.5 mg menadione (all from Sigma Chemical Company, St. Louis, Mo.) anaerobically at 37° C. for 48 hr in an atmosphere of 85% $N_2$, 10% $CO_2$, 5% $H_2$. The entire 500 ml culture was used to inoculate 20 liters of the same medium, and the latter was incubated in a fermentation tank at 37° C. for 48 hr (to a final optical density of 1.8 at 650 nm).

Purification of Low Molecular Weight Arg-gingipain 1200 ml cell-free supernatant was obtained from the 48 hr culture by centrifugation at 18,000×g for 30 min. at 4° C. Proteins in the supernatant were precipitated out by 90% saturation with ammonium sulfate. After 2 hr at 4° C., the suspension was centrifuged at 18,000×g for 30 min. The resulting pellet was dissolved in 0.05 M sodium acetate buffer, pH 4.5, 0.15 NaCl, 5 mM $CaCl_2$; the solution was dialyzed against the same buffer overnight at 4° C., with three changes with a buffer:protein solution larger than 150:1. The dialysate was then centrifuged at 25,000×g for 30 min., and the dark brown supernatant (26 ml) was then chromatographed over an agarose gel filtration column (5.0×150 cm; Sephadex G-150, Pharmacia, Piscataway, N.J.) which had been pre-equilibrated with the same buffer. The column was developed with said buffer at a flow rate of 36 ml/hr. 6 ml fractions were collected and assayed for both amidolytic and proteolytic activities, using Bz-L-Arg-pNA and azocasein as substrates. Four peaks containing amidolytic activity were identified (FIG. 1). The fractions corresponding to peak 4 were combined, concentrated by ultrafiltration (Amicon PM-10 membrane; Amicon, Beverly, Mass.) and then dialyzed overnight against 0.05 Bis-Tris, 5 mM $CaCl_2$, pH 6.0. The volume of the dialysate was 14 ml.

The 14 ml dialysate from the previous step was then applied to a DEAE-cellulose (Whatman, Maidstone, England) column (1×10 cm) equilibrated with 0.05 mM Bis-Tris, 5 mM $CaCl_2$, pH 6.0. The column was then washed with an additional 100 ml of the same buffer. About 75% of the amidolytic activity, but only about 50% of the protein, passed through the column. The column wash fluid was dialyzed against 0.05 M sodium acetate buffer containing 5 mM $CaCl_2$ (pH 4.5). This 19 ml dialysate was applied to a Mono S FPLC column (Pharmacia LKB Biotechnology Inc., Piscataway, N.J.) equilibrated with the same buffer. The column was washed with the starting buffer at a flow rate of 1.0 ml/min for 20 min. Bound proteins were eluted first with a linear NaCl gradient (0 to 0.1 M) followed by a second linear NaCl gradient (0.1 to 0.25 M), each gradient applied over a 25 min time period. Fractions were assayed for amidolytic activity using Bz-L-Arg-pNA. Fractions with activity were pooled and re-chromatographed using the same conditions. Although not detectable by gel electrophoresis, trace contamination by a proteinase capable of cleaving after lysyl residues was sometimes observed. This contaminating activity was readily removed by applying the sample to an arginyl-agarose column (L-Arginyl-SEPHAROSE 4B) equilibrated with 0.025 M Tris-HCl, 5 mM $CaCl_2$, 0.15 M NaCl, pH 7.5. After washing with the same buffer, purified enzyme was eluted with 0.05 M sodium acetate buffer, 5 mM $CaCl_2$, pH 4.5. Yields of gingipain-1 were markedly reduced by this step (about 60%).

High Molecular Weight Arg-gingipain Purification

The culture supernatant (2,900 ml) was obtained by centrifugation of the whole culture (6,000×g, 30 min, 4° C.). Chilled acetone (4,350 ml) was added to this fraction over a period of 15 min, with the temperature of the solution maintained below 0° C. at all times, using an ice/salt bath and this mixture was centrifuged (6,000×g, 30 min, −15° C.). The precipitate was dissolved in 290 ml of 20 mM Bis-Tris-HCl, 150 mM NaCl, 5 mM $CaCl_2$, 0.02% (w/v) $NaN_3$, pH 6.8 (Buffer A), and dialyzed against Buffer A containing 1.5 mM 4,4'-Dithiodipyridine disulfide for 4h, followed by 2 changes of buffer A overnight. The dialyzed fraction was centrifuged (27,000×g, 30 min, 4° C.), following which it was concentrated to 40 ml by ultrafiltration using an Amicon PM-10 membrane. This concentrated fraction was applied to a Sephadex G-150 column (5×115 cm=2260 ml; Pharmacia, Piscataway, N.J.) which had previously been equilibrated with Buffer A, and the fractionation was carried out at 30 ml/h (1.5 cm/h). Fractions (9 ml) were assayed for activity against Bz-L-Arg-pNa and Z-L-Lys-pNa (Novabiochem; 0.5 mM). Amidolytic activities for Bz-L-Arg-pNa (0.5 mM) or Z-L-Lys-pNa were measured in 0.2 M Tris.Hcl, 1 mM $CaCl_2$, 0.02% (w/v) $NaN_3$, 10 mM L-cysteine, pH 7.6. General proteolytic activity was measured with azocasein (2% w/v) as described by Barrett and Kirschke (1981) *Meth. Enzymol.* 80, 535–561 for cathepsin L. Three peaks with activity against the two substrates were found. The first (highest molecular weight) peak of activity was pooled, concentrated to 60 ml using ultrafiltration and dialyzed overnight against two changes of 50 mM Tris-HCl, 1 mM $CaCl_2$, 0.02% $NaN_3$, pH 7.4 (Buffer B).

This high MW fraction was applied to an L-Arginine-Sepharose column (1.5×30 cm=50 ml), which had previously been equilibrated with Buffer B at a flow rate of 20 ml/hr (11.3 cm/h), following which the column was washed with two column volumes of Buffer B. Following this, a step gradient of 500 mM NaCl was applied in Buffer B and the column was washed with this concentration of NaCl until the $A_{280}$ baseline fell to zero. After re-equilibration of the column in Buffer B, a gradient from 0–750 mM L-Lysine was applied in a total volume of 300 ml, followed by 100 ml of 750 mM L-Lysine. The column was once again re-equilibrated with Buffer B and a further gradient to 100 mM L-arginine in 300 ml was applied in the same way. Fractions (6 ml) from the Arg wash were assayed for activity against the two substrates as described previously. The arginine gradient eluted a major peak for an enzyme degrading Bz-L-Arg-pNa. The active fractions were pooled and dialyzed against two changes of 20 mM Bis-Tris-HCl, 1 mM $CaCl_2$, 0.02% (v/w) $NaN_3$, pH 6.4 (Buffer C) and concentrated down to 10 ml using an Amicon PM-10 membrane.

The concentrate with activity for cleaving Bz-L-Arg-pNa was applied to a Mono Q FPLC column (Pharmacia LKB Biotechnology Inc, Piscataway, N.J.) equilibrated in Buffer C, the column was washed with 5 column volumes of Buffer C at 1.0 ml/min, following which bound protein was eluted with a 3 step gradient [0–200 mM NaCl (10 min), followed by 200–250 mM NaCl (15 min) and 250–500 mM NaCl (5 min)]. The active fractions from Mono Q were pooled and used for further analyses.

Example 2

Molecular Weight Determination

The molecular weight of the purified Arg-gingipain-1 was estimated by gel filtration on a Superose 12 column (Pharmacia, Piscataway, N.J.) and by Tricine-SDS polyacrylamide gel electrophoresis. In the latter case, 1 mM TLCK was used to inactivate the protease prior to boiling, thus preventing autoproteolytic digestion.

Example 3

Enzyme Assays

Amidolytic activities of *P. gingivalis* proteinases were measured with the substrates MeO-Suc-Ala-Ala-Pro-Val-pNA at a concentration of 0.5 mM, Suc-Ala-Ala-Ala-pNA (0.5 mM), Suc-Ala-Ala-Pro-Phe-pNA (0.5 mM), Bz-Arg-pNA (1.0 mM), Cbz-Phe-Leu-Glu-pNA) (0.2 mM); S-2238, S-2222, S-2288 and S-2251 each at a concentration of 0.05 mM; in 1.0 ml of 0.2 M Tris-HCl, 5mM $CaCl_2$, pH 7.5. In some cases either 5 mM cysteine and/or 50 mM glycylglycine (Gly-Gly) was also added to the reaction mixture.

For routine assays, pH optimum determination and measurement of the effect of stimulating agents and inhibitors on trypsin-like enzymes, only Bz-L-Arg-pNA was used as substrate. Potential inhibitory or stimulatory compounds were preincubated with enzyme for up to 20 min at room temperature at pH 7.5, in the presence of 5 mM $CaCl_2$ (except when testing the effects of chelating agents) prior to the assay for enzyme activity.

General proteolytic activity was assayed using the same buffer system as described for detecting amidolytic activity, but using azocoll or azocasein (1% w/v) as substrate.

A unit of Arg-gingipain-1 enzymatic activity is based on the spectroscopic assay using benzoyl-Arg-p-nitroanilide as substrate and recording Δ absorbance units at 405 nm/min/ absorbance unit at 280 nm according to the method of Chen et al. (1992) supra.

Example 4

Enzyme Specificity

Purified Arg-gingipain-1 (0.8 μg) in 50 mM ammonium bicarbonate buffer, pH 7.7, 5 mM $CaCl_2$, was preincubated with 2 mM cysteine for 10 min, followed by the addition of either oxidized insulin B chain (225 μg) or melittin (225 μg) at 25° C. Samples were removed after various time intervals, and the reaction mixtures were subjected to HPLC (reverse phase column, MicroPak SP C-18 column) using linear gradients (0.08% trifluoroacetic acid to 0.08% trifluoroacetic acid plus 80% acetonitrile, over a 45 min period (flow rate 1.0 ml/min). Peptides were detected by monitoring $A_{220}$. Product peaks were collected and subjected to amino acid analysis and/or amino-terminal sequence analysis.

Example 5

Amino Acid Sequence Analysis

Amino-terminal amino acid sequence analysis of either Arg-gingipain-1 or degradation products from proteolytic reactions was carried out using an Applied Biosystems 4760A gas-phase sequenator, using the program designed by the manufacturer.

The amino acid sequence of the COOH terminus of SDS-denatured Arg-gingipain-1 and of Arg-gingipain-2 was determined. 10 nmol aliquots of gingipain-1 were digested in 0.2 M N-ethylmorpholine acetate buffer, pH 8.0, with carboxypeptidase A and B at room temperature, using 1:100 and 1:50 molar ratios, respectively. Samples were removed at intervals spanning 0 to 12 hours, boiled to inactivate the carboxypeptidase, and protein was precipitated with 20% trichloracetic acid. Amino acid analysis was performed on the supernatants.

Example 6

Materials

MeO-Suc-Ala-Ala-Pro-Val-pNA, Suc-Ala-Ala-Pro-Phe-pNA, Gly-Pro-pNA, Suc-Ala-Ala-Ala-pNA, Bz-Arg-pNA, diisopropylfluorophosphate, phenylmethylsulfonyl fluoride, tosyl-L-lysine chloromethyl ketone (TLCK), tosyl-L-phenylalanine chloromethyl ketone (TPCK), trans-epoxysuccinyl-L-leucylamide-(4-guanidino)butane), an inhibitor of cysteine proteinases, leupeptin, antipain and azocasein were obtained from Sigma Chemical Co., St. Louis, Mo. 3,4-Dichloroisocoumarin was obtained from Boehringer, Indianapolis, Ind. and CBz-Phe-Leu-Glu-pNA and azocoll were obtained from Calbiochem, La Jolla, Calif. S-2238 (D-Phe-Pip-Arg-pNA), S-2222 (Bz-Ile-Glu-(γ-OR)-Gly-Arg-pNA), S-2288 (D-Ile-Pro-Arg-pNA), and S-2251 (D-Val-Leu-Lys-pNA) were from Kabi-Vitrum, (Beaumont, Tex.).

Example 7

Electrophoresis

SDS-PAGE of Arg-gingipain preparation was performed as in Laemmli (1970) *Nature* 227: 680–685. Prior to electrophoresis the samples were boiled in a buffer containing 20% glycerol, 4% SDS, and 0.1% bromphenol blue. The samples were run under reducing conditions by adding 2% β-mercaptoethanol unless otherwise noted. Samples were heated for 5 min at 100° C. prior to loading onto gels. A 5–15% gradient gel was used for the initial digests of C3 and C5, and the gels were subsequently stained with Coomassie Brilliant Blue R. The C5 digest used to visualize breakdown products before and after reduction of the disulfide bonds were electrophoresed in a 8% gel. Attempts to visualize C5a in the C5 digest were carried out using 13% gels that were developed with silver stain according to the method of Merril et al. (1979) *Proc. Natl. Acad. Sci USA* 76, 4335–4340.

In some experiments (high molecular weight forms) SDS-PAGE using Tris-HCl/Tricine buffer was carried out per Shagger and Van Jagow (1987) *Analyt. Biochem.* 166, 368–379.

Electrophoresis on cellulose acetate strips were performed in 0.075 barbital buffer at pH 8.5 and 4° C. for 30 min. at 200 V. The Beckman Microzone apparatus (model R101) used for the electrophoresis of the protein, and the strips were stained using Amido Black.

Example 8

Complement Activation by Arg-Gingipain-1.

Human complement protein C3 was isolated according to the procedures described by Tack and Prahl (1976) *Biochemistry* 15, 4513–4521, and C5 was isolated by the method of DeScipio, R. G. (1981) *Biochem J.* 199, 485–496 as modified by Parkes et al. (1981) *Biochem J.* 193, 963–970. Outdated human plasma treated with barium citrate, and C3 and C5 were precipitated with 4–12% polyethylene glycol. The preparation was then fractionated over DEAE-Sephadex and by gel filtration through Sephacryl S-300. The C3, C3u, and C5 were separated using sulfated Sepharose. Contaminating C3u was removed from C5 by passage through a column of rabbit anti-C3 IgG-Sepharose. The C3 and C5 were further purified to apparent homogeneity, as visualized by SDS-PAGE, by 15 FPLC using a Mono Q (5×55 mm) anion-exchange column (Pharmacia LKB Biotechnology Inc.).

Human C5a and C3a were prepared according to the methods described by Hugli and co-workers [Hugli et al. (1975) *J. Biol. Chem.* 250, 1472–1478; Fernandez and Hugli (1976) *J. Immunol.* 117, 1688–1694; Hugli et al. (1981) *Mol. Cell. Biochem.* 41, 59–66].

Human C3 or C5 was incubated with purified Arg-gingipain-1 (purification included affinity chromatography over L-Arginyl-Sepharose 4B as described in Example 1) with a molar ratio of substrate to enzyme of 25:1 for an Arg-gingipain-1 preparation having a specific activity of 728 units or with a molar ratio of 100:1 for a gingipain-1 preparation having a specific activity of 1123 units. Incubations were carried out in 10 mM Tris HCl, 1 mM cysteine, 5 mM $CaCl_2$, and with or without 50 mM glycyl-glycine at pH 7.0 and 37° C. This incubation mixture, exclusive of the glycyl-glycine, will be referred to as the digestion buffer. At designated time points aliquots were removed, and proteolysis was inhibited by adding TLCK to a final concentration of 2 mM.

Amino acid sequence analyses of the α-chain fragments of C5 cleaved by Arg-gingipain-I were obtained after SDS-PAGE separation. The fragments were blotted onto Immobilon transfer membranes (Millipore Corp., Bedford, Mass.). Eight to 10 cycles of automated Edman degradation [Edman and Begg (1967) *Eur. J. Biochem.* 1, 80–91] were performed using an Applied Biosystems 470A Protein Sequencer. The amino termini of C5 fragments were assigned based on the known primary structure of C5 [Haviland, et al. (1991) *J. Immunol* 146, 362–3683].

Neutrophils (polymorphonuclear leukocytes, PMNs) were isolated from peripheral blood of healthy human donors according to the method described by Fehr and Dahinden (1979) *J. Clin. Invest.* 64, 8–16. Blood was drawn into syringes containing a final concentration of 10 mM EDTA. Blood was mixed in a 50-ml conical tube containing an equal volume of sterile, nonpyrogenic 6% dextran and 0.9% saline (Baxter). Cells were allowed to sediment for 60 min. at room temperature. The leukocyte-rich upper layer was collected, and 30 ml was carefully layered over 15 ml of Ficoll-Paque (Pharmacia) and centrifuged for 25 min. at 300×g in a Sorvall RT6000B centrifuge. The pellet containing PMNs was depleted of red blood cells by hypotonic lysis. The PMNs were then washed twice in Earle's balanced salt solution (EBSS, Gibco, Grand Island, N.Y.) containing 10 mM MOPS/HCl at pH 7.3. The PMNs to be used in the polarization assay were in EBSS and MOPS/HCl, and cells used for the chemotaxis assay were resuspended in EBSS containing 1% bovine serum albumin (Sigma).

The effect of products in the C5 digest on the morphology of PMNs was measured according to the assay described by Haston and Shields (1985) *J. Immunol. Methods* 81, 229–237. The C5 (90 µg) was incubated with Arg-gingipain-1 (25:1; molar ratio of C5 to enzyme) in 200 µl of digestion buffer for 180 min. at 37° C. Controls devoid of either enzyme or C5 were incubated under identical conditions. PMNs ($4 \times 10^6$/ml) were incubated with aliquots of the C5 digest for 30 min. at 37° C., then fixed with 2.5% ice-cold glutaraldehyde (2.5% glutaraldehyde in 0.9% saline, Fisher) for 2 h at 4° C. Cells were examined microscopically, and cells that deviated from the typical spherical shape were scored as polarized. The results are expressed as a percent of cells polarized (200 cells were counted per sample).

Chemotaxis of PMNs was measured as described by Dahinden et al. (1983) *J. Immunol.* 130, 857–862, in modified Boyden chambers (Adaps, Inc., Dedham, Mass., models P1 and 1/2SC). The C5 was incubated with gingipain-1 at a 100:1 molar ratio in digestion buffer for 90 min at 37° C. Controls were run as above.

Cells that migrated through the entire thickness of an 8-µm micropore filter (Sartorius, Gottingen, Federal Germany of Germany) were counted after 90 min. in an incubator (5% $CO_2$) at 37° C. The upper chamber contained the purified PMNs ($3 \times 10^6$/ml), and the lower chamber contained the chemoattractant in EBSS/albumin buffer. Zymosan-activated serum was used at 1:5 dilution as the reference chemoattractant. Results were expressed as a percentage of the 1:5 diluted zymosan-activated serum control. The buffer control typically gave 2% of the zymosan-activated serum cell response. The number of cells migrating to the lower chamber was determined by a Sysmex F-300 hematology analyzer (TOA Medical Electronics, Kobe, Japan).

C5 (400 µg) was incubated with Arg-gingipain-1 (100:1 molar ratio) in digestion buffer under the conditions described above. Approximately $2 \times 10^5$ cpm of $^{125}$I-labeled C5 was included in the digestion mixture. C5a labeled with $^{125}$I ($5 \times 10^5$ cpm) was added to the digest immediately before it was applied to a P-60 column (1.5×55 cm, Bio-Rad) equilibrated with 20 mM imidazole-HCl, containing 0.3 M NaCl, at pH 7.0. The gel filtration was performed at 4° C. using a flow rate of 10 ml/h. Fractions containing radiolabeled C5a were pooled and dialyzed extensively against distilled water at 4° C. This sample was lyophilized to dryness and resuspended in a 4-µl volume of water for analysis.

Example 9

Oligonucleotide Synthesis

Oligonucleotide primers for PCR probes and sequencing were synthesized by the phosphoramidite method with an Applied Biosystems model 394 automated DNA synthesizer (Applied Biosystems, Foster City, Calif.) and purified by PAGE and desalted on Sep-Pak (Millipore Corp., Beverly, Mass.) using standard protocols. Primer GIN-1-32 was designed to bind to the noncoding strand of Arg-gingipain DNA corresponding to the $NH_2$-terminal portion of the mature protein, i.e., to the sequence encoding amino acids 2–8 within SEQ ID NO:1. The sequence of the 32-base primer consists of 20 bases specific for Arg-gingipain and six additional bases at the 5' end (underlined), as follows: 5'-GGCTTTACNCCNGTNGARGARYTNGA-3' (SEQ ID NO:5), where N is A or G or C or T. Primer GIN-2-30 was designed to bind to the coding strand of Arg-gingipain DNA corresponding to the amino acids 25–32 of the mature protein, i.e., residues 25–32 of SEQ ID NO:1. The sequence of the 30-base primer consists of 24 bases specific for gingipain-1 (and gingipain-2) DNA and six additional bases at the 5' end (underlined), as follows: 5'-GGCTTTRTTYTTCCARTC NACRAARTCYTT-3', where R is A or G, Y is C or T and N is A or G or C or T (SEQ ID NO:6). Primer GIN-8S-48: 5'-CCTGGAGAATTCTCG TATGATCGTCATCGTAGCCAAAAAGTATGAGGG-3' (SEQ ID NO:7) was designed to bind to the noncoding strand of Arg-gingipain DNA corresponding to the amino acids 11–22 of the mature protein, i.e., amino acids 11–22 of SEQ ID NO:1, and was designed on the basis of partial DNA sequence information for the Arg-gingipain coding sequence (nucleotides 1659–1694 of SEQ ID NO:3) and included a 6-base EcoRI restriction site plus six additional bases at the 5' end (underlined). This primer was used as a probe to screen a λDASH *P. gingivalis* genomic DNA library (see below). One additional oligonucleotide GIN-14-20 (20-mers), initially designed to sequence Arg-gingipain DNA, was used as a probe to identify and then clone the 3' end of the gingipain-1 coding sequence, as a PstI-HindIII sequence. Primer GIN-14-20 was designed to bind to the noncoding strand of gingipain-1 DNA corresponding to 20 bases specific for 3' end of Arg-gingipain (nucleotides 2911–2930 within SEQ ID NO:3): 5'-ATCAACACTAATGGTGAGCC-3' (SEQ ID NO:8). A total of 71 20-mers internal primers were designed using empirically determined sequence to sequence the Arg-gingipain locus.

Example 10

Polymerase Chain Reaction

The DNA templates used in PCR was *P. gingivalis* strain H66 total cellular DNA. The PCR was run using primer GIN-1-32 (SEQ ID NO:5) along with primer GIN-2-30 (SEQ ID NO:6); PCR consistently yielded a single 105-base pair product (P105) detected on a 7% acrylamide gel representing a partial gingipain DNA. After treatment with the Klenow enzyme, P105 was cloned in pCR-Script™SK(+) (Stratagene, La Jolla, Calif.). After sequence analysis of P105, specific primer GIN-8S-48 (SEQ ID NO:7) was designed to use as a probe. The $^{32}$P-labeled GIN-8S-48 probe, was generated by kinase reaction for use in subsequent hybridization screening of the λDASH library. Incorporated nucleotides were separated from unincorporated nucleotides on a Sephadex G-25 column (Boehringer Mannheim Corporation, Indianapolis, Ind.).

Example 11

Construction and Screening of the Genomic DNA Library

λDASH and λZAP DNA libraries were constructed according to the protocols of Stratagene, using the lambda DASH™ II/BamHI cloning kit and DNA preparations from *P. gingivalis* strains H66 and W50. Libraries of $3\times10^5$ independent recombinant clones was obtained using *P. gingivalis* H66 DNA, and $1.5\times10^5$ independent recombinant clones were obtained from *P. gingivalis* W50 DNA.

Approximately $3\times10^5$ phages were grown on $5\times150$ mm agar plates, lifted in duplicate onto supported nitrocellulose transfer membrane (BAS-NC, Schleicher & Schuell, Keene, N.H.), hybridized to the $^{32}$P-labeled GIN-8S-48 probe described above. Hybridizations were performed overnight at 42° C. in 2×Denhardt's solution (Denhardt, D. T. (1966), *Biochem. Biophys. Res. Comm.* 23, 641–646), 6×SSC (SSC is 15 mM sodium citrate, 150 mM NaCl), 0.4% SDS (w/v), 500 µg/ml fish sperm DNA. The filters were washed in 2×SSC containing 0.05% SDS (w/v) at 48° C. Seven positively hybridizing plaques were purified. After extraction and purification, the DNA was analyzed by restriction enzyme digestion and agarose gel electrophoresis. The 3 kb-PstI fragment from clone A1 (*P. gingivalis* H66) was subsequently cloned into pBluescript SK(−) (Stratagene, La Jolla, Calif.) and M13mp18 and 19 and sequenced. After restriction analysis of the A1 clone, a SmaI/BamHI fragment was then cloned into pBluescript SK(−). A PstI/BamHI smaller fragment was subcloned into M13mp18 and 19 for sequencing purposes. 3.5 and 0.5 kb-BamHI fragments from the λZAP *P. gingivalis* W50 DNA library were cloned into pBluescript SK(−) and M13mp18 and 19 and sequenced. Standard protocols for cDNA library screening, lambda phage purification, agarose gel electrophoresis and plasmid cloning were employed (Maniatis et al. (1982), supra). Standard protocols for cDNA library screening, lambda phage purification, agarose gel electrophoresis and plasmid cloning were employed (Maniatis et al., 1982 supra).

Example 12

Southern Blot Analysis

The membranes were washed as described above. BamHI, HindIII- or PstI-digested *P. gingivalis* H66 DNA samples were hybridized with $^{32}$P-labeled GIN-8S-48. Two BamHI fragments of approximately 9.4 and 3.5 kb, and two PstI fragments of approximately 9.4 and 3 kb were found. No HindIII fragment was seen. BamHI- and PstI-digested λDASH DNA after screening and purification of positive recombinant clones from the library revealed one clone (A1) with a 3.5 kb BamHI fragment and a 3 kb PstI fragment; one clone (B1) with a 9.4 kb BamHI fragment and a 9.4 kb PstI fragment; and 5 clones with a 9.4 kb BamHI fragment and a 10 kb PstI fragment. The A1 clone was sequenced because the DNA predicted to encode a 50-kDa protein is approximately 1.35 kb. In order to clone the stop codon of Arg-gingipain-2, double PstI/HindIII-digested *P. gingivalis* DNA were hybridized with $^{32}$P-labeled GIN-14–20. One PstI/HindIII fragment of approximately 4.3 kb was found. This fragment was gel purified and cloned into pBluescript SK(−) for sequencing. Smaller fragments (PstI/SmaI and BamHI/HindIII) were also subcloned into M13mp18 and 19 and sequenced, and was found to include the stop codon. Table 6 hereinabove (see also SEQ ID NO:9) which presents about 7 kb of sequence extending from a PstI site upstream of the start codon through a HindIII site downstream of the end of the prepolyprotein's stop codon.

Example 13

DNA Sequencing

Double-stranded DNA cloned into pBluescript SK(−) and single-stranded DNA cloned into M13mp18 and 19 were sequenced by the dideoxy terminator method [Sanger et al. (1977) *Proc. Natl. Acad. Sci. USA* 74, 5463–5467] using sequencing kits purchased from United States Biochemicals (Cleveland, Ohio; Sequenase version 2.0). The DNA was sequenced using M13 universal primer, reverse sequencing primer and internal primers as well understood in the art.

We claim:

1. A recombinant DNA molecule comprising a nucleotide sequence encoding an Arg-gingipain protein containing an enzymatically active protease component having an amino acid sequence as given in one of SEQ ID NO:4 from amino acid 1 to amino acid 510 or SEQ ID NO:10 from amino acid 228 to amino acid 719, and a hemagglutinin component.

2. The recombinant DNA molecule of claim 1 wherein said enzymatically active protease component has an amino acid sequence as given in SEQ ID NO:10 from amino acid 228 to amino acid 719 and a hemaglutinin component having an amino acid sequence selected from the group consisting of from amino acid 720 to amino acid 1091, from amino acid 1092 to amino acid 1429 and from amino acid 1430 to amino acid 1704, each as given in SEQ ID NO:10.

3. The recombinant DNA molecule of claim 1 wherein said Arg-gingipain is encoded within a nucleotide sequence as given in SEQ ID NO:9 from nucleotide 949–6063.

4. The recombinant DNA molecule of claim 3 encoding a prepolyprotein having an amino acid sequence as given in SEQ ID NO:10.

* * * * *